United States Patent
Wang et al.

(10) Patent No.: US 8,829,003 B2
(45) Date of Patent: Sep. 9, 2014

(54) COMPOUNDS FOR TREATING PROLIFERATIVE DISORDERS

(75) Inventors: Shudong Wang, Nottinghamshire (GB); Osama Chahrour, Nottinghamshire (GB); Tiangong Lu, Nottinghamshire (GB); Anran Hu, Nottinghamshire (GB)

(73) Assignee: Changzhou Le Sun Pharmaceuticals Limited (CN)

( * ) Notice: Subject to any disclaimer, the term of this patent is extended or adjusted under 35 U.S.C. 154(b) by 0 days.

(21) Appl. No.: 13/806,602

(22) PCT Filed: Jun. 21, 2011

(86) PCT No.: PCT/GB2011/051162
§ 371 (c)(1),
(2), (4) Date: Mar. 25, 2013

(87) PCT Pub. No.: WO2011/161446
PCT Pub. Date: Dec. 29, 2011

(65) Prior Publication Data
US 2013/0190325 A1    Jul. 25, 2013

(30) Foreign Application Priority Data
Jun. 21, 2010    (GB) .................... 1010359.6

(51) Int. Cl.
A61K 31/497    (2006.01)
C07D 213/62    (2006.01)

(52) U.S. Cl.
USPC ....... 514/253.12; 514/357; 546/294; 546/194

(58) Field of Classification Search
USPC .............. 514/253.12, 347, 357; 546/294, 194
See application file for complete search history.

(56) References Cited

U.S. PATENT DOCUMENTS 5,612,340 A * 3/1997 Zimmermann .................. 514/85
7,799,782 B2 * 9/2010 Munson et al. ............ 514/234.5

FOREIGN PATENT DOCUMENTS

WO    WO 03/072062 A2    9/2003
WO    WO 2005/046599 A2    5/2005
WO    WO 2008/088803 A2    7/2008

OTHER PUBLICATIONS

Maniar et al. CAS: 149: 315788, 2008.*
Makosza et al. CAS: 128: 48012, 1997.*
International Search Report prepared by the European Patent Office on Sep. 28, 2011, for International Application No. PCT/GB2011/051162.
Written Opinion prepared by the European Patent Office on Sep. 28, 2011, for International Application No. PCT/GB2011/051162.
Official Action (English translation) for Chinese Patent Application No. 201180030413.9 dated Sep. 11, 2013, 5 pages.
Official Action (English translation) for Chinese Patent Application No. 201180030413.9 dated Jan. 28, 2014, 3 pages.
Official Action (English translation) for Chinese Patent Application No. 201180030413.9 dated Apr. 21, 2014, 3 pages.
Official Action for European Patent Application No. 11736135.2 dated Apr. 16, 2014, 4 pages.

* cited by examiner

*Primary Examiner* — Rei-tsang Shiao
(74) *Attorney, Agent, or Firm* — Sheridan Ross, P.C.

(57) ABSTRACT

A compound of formula (I) or a pharmaceutically acceptable salt or solvate or physiologically hydrolysable, solubilizing or immobilizable derivative thereof; wherein: any one or two of $X_1$, $X_2$ and $X_3$ is a N atom and the remaining two or one of $X_1$, $X_2$ and $X_3$ are independently $CR^{13}$; Y is selected from $SO_2$ and SO; $R^1$, $R^2$, $R^3$, and $R^7$ and the one or two $R^{13}$ groups are each independently selected from H and $R^{10}$, $R^{10}$ is selected from $R^8$, alkyl, aryl, heteroaryl and combinations of two or more thereof and combinations with one or more $R^9$, or $R^{10}$ is one or more moieties $R^{11}$ Sinking one or more alkyl, alkoxy, aryl, heteroaryl or $R^8$ or $R^9$ groups or combinations thereof, directly or via a moiety selected from alkylene, arylene, heteroarylene or combinations thereof, wherein alkyl, aryl, heteroaryl groups or moieties thereof may be substituted with one or more groups $R^{12}$, or $R^{10}$ is selected from a group $R^{12}$; $R^{11}$ is selected from 0-, N—, NH—, N=C, CO—, C00-, CON—, CONH—, $SO_2$-, $SO_2N$—, $SO_2NH$—; $R^{12}$ is selected from halogen, $NH_2$, $NO_2$, CN, OH, COOH, $CONH_2$, C(=NH)$NH_2$, $SO_3H$, $SO_2NH_2$, $SO_2CH_3$, $OCH_3$, $OCH_2CH_3$, $CF_3$; $R^8$ and $R^9$ comprise one or more solubilizing moieties independently chosen from i) neutral hydrophilic groups, ii) ionisable organic acids, iii) ionisable organic bases, iv} chemical functions or moieties providing covalent or non-covalent attachment or binding to a solid phase or an immobile receptor and combinations thereof; $R^4$, $R^5$ and $R^6$ are each independently selected from H and $R^{10}$, or two of $R^4$ to $R^6$ are linked to form a cyclic ether or amine containing one or more additional oxygen or nitrogen atoms. The compound may be used for treating a condition mediated by one or more enzymes selected from AKT, Aurora kinase, BCR-ABL, CDK, FLT, GSK3, IKK, JAK, MAPK, PDGF, PI3K, PKA, PKB, PKC, PLK, Src and VEGF family enzymes, or for treating cancer or other proliferative disorder, or for inhibiting growth of cancer cells, or for inducing apoptosis of cancer cells, in a human or animal subject.

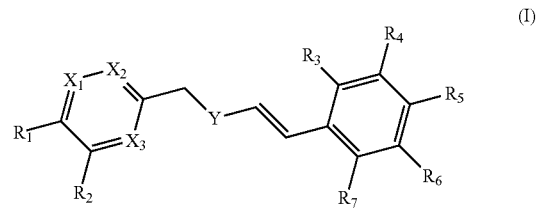

(I)

21 Claims, 6 Drawing Sheets

FIGURE 4

| Compound | Structure | MW | 48h-MTT Cytotoxicity, GI$_{50}$ μM | |
|---|---|---|---|---|
| | | | HCT-116 | MCF-7 |
| A.10 | 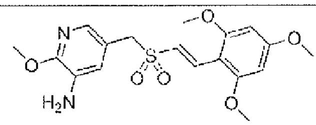 | 394.1 | 0.02 | 0.11 |
| A.12 | 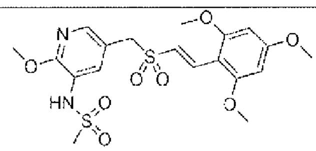 | 472.1 | 0.66 | 0.62 |
| A.13 | 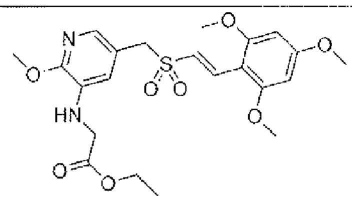 | 480.2 | 0.94 | 0.67 |
| A.17 | 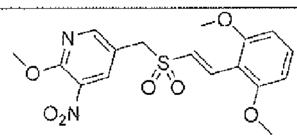 | 394.1 | 0.91 | 0.97 |
| A.29 | 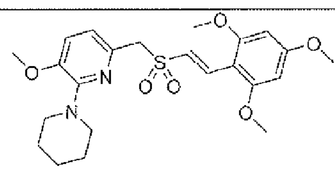 | 462.2 | 0.88 | 4.60 |

FIGURE 7

| Parameter (unit) | | 2mg/kg by IV | | 10mg/kg by PO | |
|---|---|---|---|---|---|
| | | A.12 | ON01910.Na | A.12 | ON01910.Na |
| Exposure | $C_{max}$ (ng/mL) | 4225 | 5554 | 2971.8 | 182.4 |
| | $AUC_{0-t}$ (ng.hr/mL) | 1209.3 | 975.5 | 3388.6 | 434.7 |
| Elimination | $t_{1/2}$ (hrs) | 3.2 | 2.5 | 3.0 | 2.6 |
| Clearance | Cl (mL/min/kg) | 27.6 | 33.9 | - | - |
| Volume of Distribution | $V_d$ (mL/kg) | 7698.9 | 7482 | - | - |
| Oral Bioavailability | F (%) | | | 56 | 9 |

COMPOUNDS FOR TREATING PROLIFERATIVE DISORDERS

CROSS REFERENCE TO RELATED APPLICATIONS

This application is a national stage application under 35 U.S.C. 371 and claims the benefit of PCT Application No. PCT/GB2011/051162 having an international filing date of Jun. 21, 2011, which designated the United States, which PCT application claimed the benefit of Great Britain Application No. 1010359.6 filed Jun. 21, 2010, the disclosures of each of which are incorporated herein by reference.

The present invention relates to the use of substituted (E)-3-(styrylsulfonylmethyl)heteroaryl and (E)-3-(styrylsulfinylmethyl)heteroaryl compounds that have broad therapeutic applications as anti-proliferative agents. The invention also provides processes for preparing compounds, pharmaceutically acceptable compositions comprising the compounds, and the use of the compounds and methods of using the compounds and compositions in the treatment of proliferative disorders.

BACKGROUND

The search for novel therapeutic agents has been advanced in recent years by a better understanding of the structure of enzymes associated with diseases. One important class of enzymes that has been the subject of extensive study is protein kinases. Protein kinases constitute a large family of structurally related enzymes that are responsible for the control of a wide variety of signal transduction processes within the cell. Many diseases are associated with abnormal cellular responses triggered by protein-kinase mediated events. These diseases include but are not limited to neurodegenerative diseases, autoimmune diseases, cancer, inflammatory diseases and metabolic diseases. Therefore a substantial effort has been made in medicinal chemistry to discover protein kinase inhibitors as effective therapeutics.

The demonstration of clinical activity of a number of kinase inhibitors including cancer drugs such as Glivec and Iressa has generated considerable interest in the search for kinase inhibitors with novel pharmacophores. Non-ATP competitive inhibitors for cancer therapy are of interest in order to overcome the problems associated with ATP-analogues having poor selectivity and drug resistance. Compound ON01910 (which is described in Bioorg. Med. Chem. Lett. 2011 May 15; 21(10), 3066-9, WO 03/072062 and WO 2008/088803) has recently demonstrated excellent anti-tumor activity and safety profiles in clinical trials.

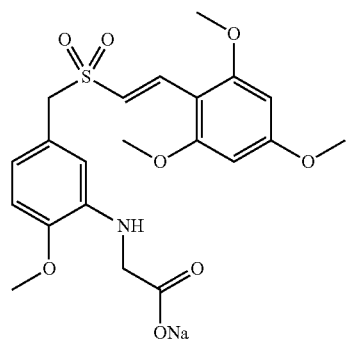

ON01910.Na

The present invention provides compounds with similar biological profiles but improved pharmaceutical properties.

The object of the present invention is to provide compositions of substituted 3-(styrylsulfonylmethyl)heteroaryl and 3-(styrylsulfinylmethyl)heteroaryl compounds, and methods for the treatment of cancer and other proliferative diseases.

BRIEF SUMMARY OF THE DISCLOSURE

A first aspect of the present invention relates to a compound of formula I and its pharmaceutically acceptable salts or solvates and physiologically hydrolysable, solubilising or immobilisable derivatives:

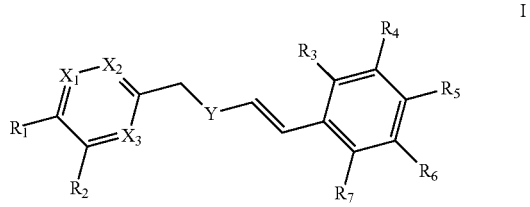

wherein:
any one or two of $X_1$, $X_2$ and $X_3$ is a N atom and the remaining two or one of $X_1$, $X_2$ and $X_3$ are independently $CR^{13}$;

Y is selected from $SO_2$ and SO;

$R^1$, $R^2$, $R^3$, and $R^7$ and the one or two $R^{13}$ groups are each independently selected from H and $R^{10}$, $R^{10}$ is selected from $R^8$, alkyl, aryl, heteroaryl and combinations of two or more thereof and combinations with one or more $R^9$, or $R^{10}$ is one or more moieties $R^{11}$ linking one or more alkyl, alkoxy, aryl, heteroaryl or $R^8$ or $R^9$ groups or combinations thereof, directly or via a moiety selected from alkylene, arylene, heteroarylene or combinations thereof, wherein alkyl, aryl, heteroaryl groups or moieties thereof may be substituted with one or more groups $R^{12}$, or $R^{10}$ is selected from a group $R^{12}$;

$R^{11}$ is selected from O—, N—, NH—, N=C, CO—, COO—, CON—, CONH—, $SO_2$—, $SO_2N$—, $SO_2NH$—;

$R^{12}$ is selected from halogeno, $NH_2$, $NO_2$, CN, OH, COOH, $CONH_2$, C(=NH)$NH_2$, $SO_3H$, $SO_2NH_2$, $SO_2CH_3$, $OCH_3$, $OCH_2CH_3$, $CF_3$;

$R^8$ and $R^9$ comprise one or more solubilising moieties independently chosen from i) neutral hydrophilic groups, ii) ionisable organic acids, iii) ionisable organic bases, iv) chemical functions or moieties providing covalent or non-covalent attachment or binding to a solid phase or an immobile receptor and combinations thereof;

$R^4$, $R^5$ and $R^6$ are each independently selected from H and $R^{10}$, or two of $R^4$ to $R^6$ are linked to form a cyclic ether or amine containing one or more additional oxygen or nitrogen atoms.

In a preferred embodiment $X_2$ is CH, one of $X_1$ and $X_3$ is a N atom and the remaining one of $X_1$ and $X_3$ is $CR^{13}$. In this embodiment the compound has the formula Ia

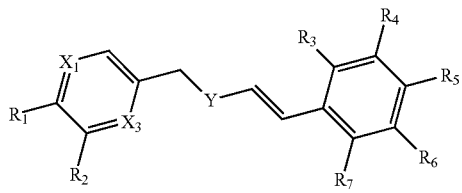

Ia wherein one of $X_1$ and $X_3$ is a nitrogen atom, the remaining one of $X_1$ and $X_3$ is $CR^{13}$, and the other substituent groups are as described above with reference to formula I. The compound Ia may be provided in the form of its pharmaceutically acceptable salts or solvates and physiologically hydrolysable, solubilising or immobilisable derivatives. For example, it may be provided as a pharmaceutically acceptable salt or ester.

Further aspects of the invention relate to a process for the preparation of a compound of formula I as hereinbefore defined, to a process for the preparation of precursors or intermediates, and to novel precursors or intermediates.

In a further aspect the invention relates to a compound of formula I or a pharmaceutically acceptable salt, solvate or physiologically hydrolysable, solubilising or immobilising derivative thereof, for use in treating a condition mediated by an enzyme selected from one or more of AKT, Aurora kinase, BCR-ABL, CDK, FLT, GSK3, IKK, JAK, MARK, PDGF PI3K, PKA, PKB, PKC, PLK Src and VEGF family enzymes, e.g. from one or more of PLK, Aurora kinase, BCR-ABL, CDK, FLT, IKK, JAK, MAPK, PDGF, VEGF and Src family enzymes, particularly from one or more of PLK, aurora kinase, CDK or at least one tyrosine kinase including BCR-ABL, or for treating cancer or other proliferative disorder, or for inhibiting growth of cancer cells, in particular tumor cells or for inducing apoptosis of cancer cells, in particular tumor cells, in a human or animal subject. In one such aspect the compound is of formula Ia or a pharmaceutically acceptable salt, solvate or physiologically hydrolysable, solubilising or immobilising derivative thereof.

In a further aspect the invention relates to the use of a compound of formula I or a pharmaceutically acceptable salt, solvate or physiologically hydrolysable, solubilising or immobilising derivative thereof, in the manufacture of a medicament for treating a condition mediated by an enzyme selected from one or more of AKT, Aurora kinase, BCR-ABL, CDK, FLT, GSK3, IKK, JAK, MARK, PDGF PI3K, PKA, PKB, PKC, PLK Src and VEGF family enzymes, e.g. from one or more PLK, Aurora kinase, BCR-ABL, CDK, FLT, IKK, JAK, MARK, PDGF, VEGF and Src family enzymes, particularly from one or more of PLK, aurora kinase, BCR-ABL, MARK, AKT and PI3K enzymes, or for treating cancer or other proliferative disorder, or for inhibiting growth of cancer cells, in particular tumor cells or for inducing apoptosis of cancer cells, in particular tumor cells, in a human or animal subject. In one such aspect the compound is of formula Ia or a pharmaceutically acceptable salt, solvate or physiologically hydrolysable, solubilising or immobilising derivative thereof.

In a further aspect of the invention, there is provided a method for treating a condition mediated by one or more enzymes selected from AKT, Aurora kinase, BCR-ABL, CDK, FLT, GSK3, IKK, JAK, MAPK, PDGF PI3K, PKA, PKB, PKC, PLK Src and VEGF family enzymes, e.g. selected from one or more of PLK, Aurora kinase, BCR-ABL, CDK, FLT, IKK, JAK, MAPK, PDGF, VEGF and Src family enzymes, particularly from one or more of PLK, aurora kinase, BCR-ABL, MARK, AKT and PI3K enzymes, or for treating cancer or other proliferative disorder, or for inhibiting growth of cancer cells, in particular tumor cells or for inducing apoptosis of cancer cells, in particular tumor cells, in a human or animal subject, the method comprising administering to a human or animal in need thereof a therapeutically effective amount of a compound of formula I or a pharmaceutically acceptable salt, solvate, or physiologically hydrolysable, solubilising or immobilising derivative thereof. In one such aspect the compound is of formula Ia or a pharmaceutically acceptable salt, solvate or physiologically hydrolysable, solubilising or immobilising derivative thereof.

In a further aspect of the invention, there is provided the use of a compound of formula I or a pharmaceutically acceptable salt, solvate, or physiologically hydrolysable, solubilising or immobilising derivative thereof in a method for treating a condition mediated by an enzyme selected from one or more AKT, Aurora kinase, BCR-ABL, CDK, FLT, GSK3, IKK, JAK, MAPK, PDGF MK, PKA, PKB, PKC, PLK Src and VEGF family enzymes, e.g. selected from one or more of PLK, Aurora kinase, BCR-ABL, CDK, FLT, IKK, JAK, MAPK, PDGF, VEGF and Src family enzymes, particularly from one or more of PLK, aurora kinase, BCR MAPK or PI3K, or for treating cancer or other proliferative disorder, or for inhibiting growth of cancer cells, in particular tumor cells or for inducing apoptosis of cancer cells, in particular tumor cells. In one such aspect the compound is of formula Ia or a pharmaceutically acceptable salt, solvate or physiologically hydrolysable, solubilising or immobilising derivative thereof.

A further aspect of the invention relates to the use of a compound of formula I or a pharmaceutically acceptable salt or solvate or physiologically hydrolysable, solubilising or immobilising derivative thereof, in an assay for identifying candidate compounds capable of treating a condition mediated by an enzyme selected from one or more of AKT, Aurora kinase, BCR-ABL, CDK, FLT, GSK3, IKK, JAK, MAPK, PDGF PI3K, PKA, PKB, PKC, PLK Src and VEGF family enzymes, particularly from one or more PLKs, aurora kinase, BCR MAPK or PI3K, e.g. from one or more of PLK, Aurora kinase, BCR-ABL, CDK, FLT, IKK, JAK, MAPK, PDGF, VEGF and Src family enzymes, particularly from one or more of PLK, aurora kinase, BCR MAPK or PI3K, or for treating cancer or other proliferative disorders. In one such aspect the compound is of formula Ia or a pharmaceutically acceptable salt, solvate or physiologically hydrolysable, solubilising or immobilising derivative thereof.

A further aspect of the invention relates to a pharmaceutical composition comprising a compound of formula I or a pharmaceutically acceptable salt or solvate, or physiologically hydrolysable, solubilising or immobilising derivative thereof, in association with one or more diluents, carriers or excipients. In one such aspect the compound is of formula Ia or a pharmaceutically acceptable salt, solvate or physiologically hydrolysable, solubilising or immobilising derivative thereof.

The compounds of the invention are effective at inhibiting growth of cancer cells and inducing apoptosis of cancer cells and can act as cell-cycle inhibitors. Surprisingly, the compounds of the invention may be of comparable or greater effectiveness than the clinical compound ON01910.Na, whilst exhibiting improved oral bioavailability as compared to that compound. In particular, the compounds show excellent oral bioavailability, indicating that they could be used as orally administered medicaments whilst still being effective as anti-proliferative agents, e.g. in cancer therapy.

Therefore a key benefit of the invention is that the compounds of the invention can be used as anti-tumor agents or as agents against other proliferative disorders, in a similar manner to the known clinical compound ON01910.Na, but also have properties that make them suitable for oral administration. It would not have been predicted that the compounds of the invention would have both excellent effects in terms of inhibiting growth of cancer cells, inducing apoptosis of cancer cells and inhibiting cell-cycles whilst also having excellent oral bioavailability.

In preferred embodiments of the aspects of the invention, therefore, the compound may be provided in a form suitable for oral administration, or may be administered orally to the human or animal in need.

In a preferred embodiment of the aspects of the invention $X_1$ is N and $X_2$ and $X_3$ are $CR^{13}$, or $X_2$ is N and $X_1$ and $X_3$ are $CR^{13}$, or $X_3$ is N and $X_1$ and $X_2$ are $CR^{13}$, such that the heteroaryl ring is an optionally substituted-pyridine. In particular, it is preferred that $X_2$ is CH, one of $X_1$ and $X_3$ is a N atom and the remaining one of $X_1$ and $X_3$ is $CR^{13}$.

In a preferred embodiment of the aspects of the invention $R^{10}$ is selected from $R^8$, alkyl, alkyl-$R^8$, alkyl-cycloalkyl which may be part unsaturated, cycloheteroalkyl, alkyl-cycloheteroalkyl, aryl, aryl-$R^8$, aralkyl, aralkyl-$R^8$, heteroaryl, alkyl-heteroaryl, halogeno, $NO_2$, CN, OH, O-alkyl, O-cycloalkyl which may be part unsaturated, O-aryl, O-heteroaryl, O—$R^8$, S-alkyl, $NH_2$, NH-alkyl, part unsaturated NH-cycloalkyl, NH-cycloheteroalkyl, NH-aryl, NH-heteroaryl, N-(alkyl)$_2$, N-(aryl)$_2$, N-(alkyl)(cycloalkyl), N-(alkyl)(cycloheteroalkyl), N-(alkyl)(aryl), N-(alkyl)(heteroaryl), NH—$R^8$, N—($R^8$)($R^9$), N-(alkyl)($R^8$), N-(aryl)($R^8$), NCHalkyl, NC(alkyl)$_2$, NC(alkyl)($R^8$), NC($R^8$)($R^9$), COOK, COO—$R^8$, COO-alkyl, CONH$_2$, CONH-alkyl, CONH-aryl, CONK-heteroaryl, CON-(alkyl)($R^8$), CON(aryl)($R^8$), CON(heteroaryl)($R^8$), CONH—$R^8$, CON—($R^8$)($R^9$), NHCO-alkyl, NHCO-aryl, NHCO-heteroaryl, NHCO—$R^8$, $SO_3H$, $SO_2$-alkyl, $SO_2$-alkyl-$R^8$, $SO_2$-aryl, $SO_2$-aryl-$R^8$, $SO_2$-heteroaryl, $SO_2$-heteroaryl-$R^8$, $SO_2NH_2$, $SO_2NH$—$R^8$, $SO_2N$—($R^8$)($R^9$), $NHSO_2R^8$, $CF_3$, CO—$R^8$, CO-alkyl, CO-alkyl-$R^8$, CO-cycloheteroalkyl, CO-aryl, CO-aryl-$R^8$, CO-heteroaryl, CO-heteroarylalkyl or CO-heteroaryl$R^8$, wherein alkyl, aryl, aralkyl, heteroaryl groups may be further substituted with one or more groups selected from halogeno, $NO_2$, CN, OH, O-methyl, $NH_2$, COOH, $CONH_2$ and $CF_3$. Preferably a cycloheteroalkyl is a morpholino, piperazinyl or piperadinyl.

In a preferred embodiment of the aspects of the invention $R^1$, $R^2$ and $R^{13}$ are independently selected from: H, CN, $CF_3$, halogeno, OH, O-alkyl, O-cycloalkyl which may be part unsaturated, O-heteroaryl, S-alkyl, $C_{1-6}$ alkyl, alkyl-cycloalkyl which may be part unsaturated, aryl, cycloheteroalkyl, alkylcycloheteroalkyl such as $CH_2$-cycloheteroalkyl, heteroaryl, alkyl-heteroaryl such as $CH_2$-heteroaryl, $NO_2$, $NH_2$, NH-alkyl, N(alkyl)$_2$, N-(alkyl)($R^8$), part unsaturated NH-cycloalkyl, NH-cycloheteroalkyl, NH-heteroaryl, NHC(=O)alkyl, NHalkylCOOH, $NHSO_2$alkyl, $NHSO_2R^8$, NCHalkyl, NC(alkyl)$_2$, NC(alkyl)($R^8$), NC($R^8$)($R^9$), $CONH_2$, CONH-(alkyl), CONH-(heteroaryl), CON-(alkyl)($R^8$), $R^8$, $CO_2$alkyl, CO-alkyl, CO-cycloheteroalkyl, CO-heteroaryl, CONH-heteroaryl; wherein alkyl, cycloheteroalkyl, aryl, aralkyl, heteroaryl groups may be further substituted with one or more groups selected from halogeno, $NO_2$, ON OH, O-methyl, $NH_2$, COOH, $CONH_2$ and $CF_3$.

In a preferred embodiment of the aspects of the invention $R^1$ is selected from $CH_3$, $OCH_3$, $OCH_2CH_3$, O-propyl, O-butyl, halogeno, $NH_2$, NH-alkyl, N(alkyl)$_2$, $CO_2$alkyl, C(=O)-alkyl, C(=O)$NH_2$, C(=O)NH-alkyl and heteroaryl. The alkyl groups may, for example, be $C_1$-$C_8$ alkyl such as $C_{1-6}$ alkyl or $C_{1-3}$ alkyl.

In a preferred embodiment of the aspects of the invention $R^2$ is selected from $CH_3$, $OCH_3$, $OCH_2CH_3$, $OCH_2CH_2Oalkyl$, $OCH_2CH_3N(alkyl)_2$, OH, halogeno, $NO_2$, $NH_2$, NH-alkyl, NHC(=O)alkyl, NHalkylCOOH, NHalkylC(=O)$NH_2$, NHalkylC(=O)alkyl, NHalkyl, N(alkyl)$_2$, cycloheteroalkyl, part unsaturated NH-cycloalkyl, NH-heteroaryl, $NHSO_2$alkyl, $NHSO_2$haloalkyl, NH-cycloheteroalkyl, and NH-cycloheteroalkyl substituted with $SO_2$ alkyl or heteroalkyl. The alkyl groups may, for example, be $C_{1-8}$ alkyl such as $C_{1-6}$ alkyl or $C_{1-3}$ alkyl. In one such embodiment, $R^2$ is selected from $NO_2$, $NH_2$, NHMe, NHC(=O)Me, NHEt, $NMe_2$, $NEt_2$, NMeC(=O)Me, NEtC(=O)Me, $NEtCO_2Me$, $NHCH_2O$(=O)Et, $NHCH_2CO_2Et$, $NHCH_2C$(=O)Me, $NHCH_2CO_2H$, $NHCH_2C$(=O)$NH_2$, $NHSO_2Me$, $NHSO_2CF_3$, $NHCH_2CH_2NEt_2$,

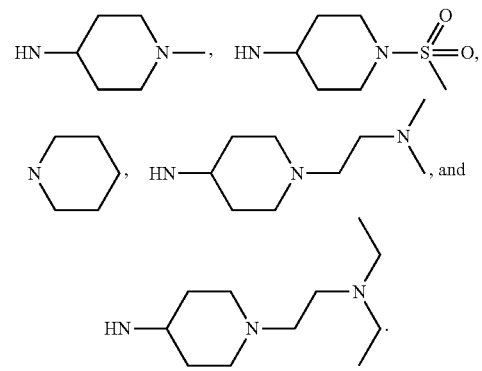

In a preferred embodiment of the aspects of the invention $R^{13}$ is selected from H and $C_{1-3}$ alkyl.

In a preferred embodiment of the aspects of the invention each $R^3$ or $R^7$ is independently selected from H, $C_{1-4}$ alkyl, CN, $CF_3$, halogeno, $NO_2$, O-methyl, O-ethyl, O-propyl, O-butyl, S-alkyl, $NH_2$, NH-alkyl, N(alkyl)$_2$, $CO_2$alkyl, C(=O)-alkyl, C(=O)$NH_2$, C(=O)NH-alkyl and heteroaryl. The alkyl groups may, for example, be $C_{1-8}$ alkyl such as $C_{1-6}$ alkyl or $C_{1-3}$ alkyl.

In a preferred embodiment of the aspects of the invention $R^4$, $R^5$ and $R^6$ are independently selected from H, halogeno, $NO_2$, ON, OH, $NH_2$, O-alkyl, O-cycloalkyl which may be part unsaturated, O-aryl, O-heteroaryl, S-alkyl, N-linked N-(alkyl)(cycloheteroalkyl), $SO_2$-cycloheteroalkyl and CO-cycloheteroalkyl. The alkyl groups may, for example, be $C_{1-8}$ alkyl such as $C_{1-6}$ alkyl or $C_{1-3}$ alkyl. It may be that $R^4$ and $R^6$ are both H.

In a preferred embodiment of the aspects of the invention two or more, such as three or more, of $R^3$ to $R^7$ are independently selected from —$OC_{1-6}$ alkyl. It may be that $R^3$, $R^5$ and $R^7$ are independently selected from —$OC_{1-6}$ alkyl, such as O-methyl, O-ethyl, O-propyl and O-butyl.

BRIEF DESCRIPTION OF THE DRAWINGS

Embodiments of the invention are further described hereinafter with reference to the accompanying Figures:

FIG. 4 is a table illustrating anti-proliferative activity of the selected compounds according to the invention.

FIG. 7 is a table illustrating results for intravenous and orally administered compound A.12 and ON01910.Na in mice.

DETAILED DESCRIPTION

Figure 1:
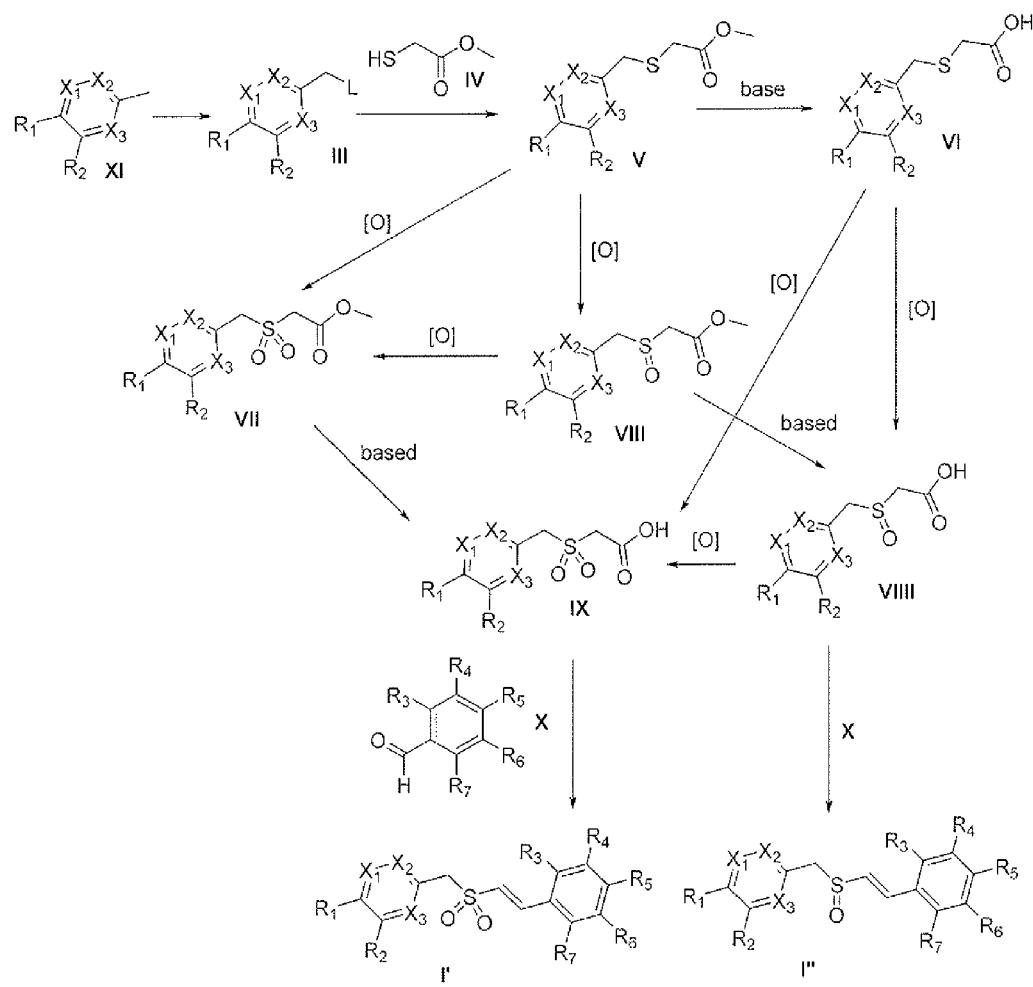
FIG. 1 illustrates processes for preparing compounds of Formula I of the invention.
Figure 2:
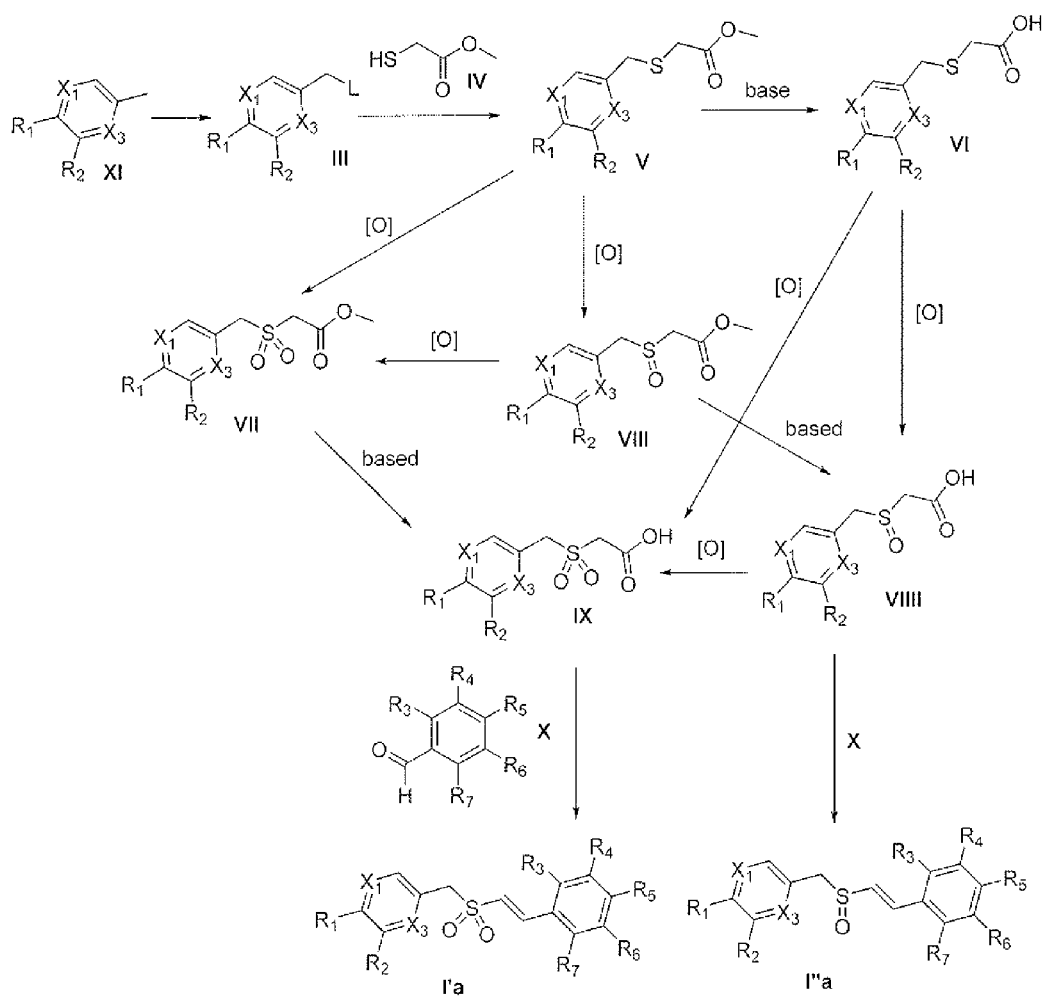
FIG. 2 illustrates processes for preparing compounds of Formula Ia of the invention.

As used herein the term "alkyl" includes both straight chain and branched alkyl groups. The alkyl group may be substituted (either mono- or poly-) or unsubstituted. Suitable substituents include, for example, halo (e.g. F or Cl), $OCH_3$, $CF_3$, OH, CN, $NO_2$, $SO_3H$, $SO_2NH_2$, $SO_2Me$, $NH_2$, COOH, $CONH_2$ and alkoxy. Preferably, the alkyl group is a $C_{1-20}$ alkyl group, more preferably a $C_{1-15}$, more preferably still a $C_{1-12}$ alkyl group, such as a $C_{1-10}$ alkyl group or $C_{1-8}$ alkyl group, more preferably still a $C_{1-6}$ alkyl group, such as a $C_{1-5}$ alkyl group or $C_{1-4}$ alkyl group, more preferably a $C_{1-3}$ alkyl group. Particularly preferred alkyl groups include, for example, methyl, ethyl, n-propyl, iso-propyl, n-butyl, iso-butyl, tert-butyl, pentyl and hexyl.

As used herein, the term "heteroalkyl" includes an alkyl group as defined above which comprises one or more heteroatoms. The heteroatom may suitably be N, O or S. Specifically, one or more carbon atom in the alkyl group may be replaced with a heteroatom independently selected from N, O and S.

As used herein, the term "cycloalkyl" refers to a cyclic alkyl group which may be substituted (either mono- or poly-) or unsubstituted. Suitable substituents include, for example, halo (e.g. F or Cl), $CF_3$, OH, CN, $NO_2$, $SO_3H$, $SO_2NH_2$, $SO_2Me$, $NH_2$, COOH, $CONH_2$ and alkoxy. Preferably, the cycloalkyl group has from 3 to 12 carbon atoms having a single cyclic ring or multiple condensed rings.

As used herein, and as would be well known to a person of skill in the art, the term "group" refers to a monovalent substituent; the term "moiety" refers to a divalent group; the term "alkylene" refers to a divalent alkyl group; the term "arylene" refers to a divalent aryl group; and the term "heteroarylene" refers to a divalent heteroaryl group.

As used herein, and as would be well known to a person of skill in the art, the term "alkyl, aryl, heteroaryl and combinations of two or more thereof" refers to alkyl, aryl, heteroaryl and combinations of one or more of alkylene, arylene and heteroarylene with alkyl, aryl and heteroaryl. For example, such a combination could be alkylenearyl, alkyleneheteroaryl, arylenealkyl, aryleneheteroaryl, heteroarylenealkyl or heteroarylenearyl.

As used herein, and as would be well known to a person of skill in the art, the term "alkyl, aryl, heteroaryl . . . and combinations with one or more $R^9$" includes reference to alkylene-$R^9$, arylene-$R^9$, heteroarylene-$R^9$, alkylene-$R^9$—, arylene-$R^9$— and heteroarylene-$R^9$—, wherein —$R^9$ is a $R^9$ group and —$R^9$— is a $R^9$ moiety.

As used herein, and as would be well known to a person of skill in the art, the term "$R^4$ to $R^6$ are linked to form a cyclic ether or amine containing one or more additional oxygen or nitrogen atoms" refers to any two of $R^4$ to $R^6$ each independently representing hydrocarbon groups (e.g. alkylene groups) which are linked together with one or more additional oxygen or nitrogen atoms to form a cyclic ether or amine ring. The ring may be saturated or unsaturated.

As used herein, and as would be well known to a person of skill in the art, the term "$R^8$ and $R^9$ comprise one or more solubilising moieties" refers to $R^8$ and $R^9$ each comprising one or more solubilising moieties or groups.

The term "cycloheteroalkyl" refers to a cyclic heteroalkyl group which may be substituted (either mono- or poly-) or unsubstituted. A cyclic heteroalkyl group is preferably a monovalent saturated or unsaturated group having a single ring or multiple condensed rings, with from 1 to 15 carbon atoms and from 1 to 4 hetero atoms selected from nitrogen, sulfur or oxygen within the ring. Suitable substituents include, for example, halo (e.g. F or Cl), $CF_3$, OH, CN, $NO_2$, $SO_3H$, $SO_2NH_2$, $SO_2Me$, $NH_2$, COOH, $CONH_2$ and alkoxy. Preferred cycloheteroalkyl groups include morpholino, piperazinyl and piperidinyl groups.

As used herein, the term "aryl" refers to an aromatic, substituted (either mono- or poly-) or unsubstituted group, and includes, for example, phenyl, naphthyl etc. A preferred aromatic group is an unsaturated aromatic carbocyclic group of from 6 to 14 carbon atoms having a single ring (e.g. phenyl) or multiple condensed (fused) rings (e.g. naphthyl or anthryl). Again, suitable substituents include, for example, halo (e.g. F or Cl), $CF_3$, OH, CN, $NO_2$, $SO_3H$, $SO_2NH_2$, $SO_2Me$, $NH_2$, COOH, $CONH_2$ and alkoxy.

As used herein, the term "heteroaryl" refers to an aromatic, substituted (mono- or poly-) or unsubstituted group, which comprises one or more heteroatoms. The heteroatom may preferably be N, O or S. A preferred aromatic group which comprises one or more heteroatoms is an aromatic group of from 1 to 15 carbon atoms and 1 to 4 heteroatoms selected from oxygen, nitrogen and sulfur within at least one ring (if there is more than one ring). Preferred heteroaryl groups include pyrrole, pyrazole, pyrimidine, pyrazine, pyridine, pyridazine, quinoline, triazine, triazole, thiophene, selenazol, thiazole and furan, Again, suitable substituents include, for example, halo, $CF_3$, OH, CN, $NO_2$, $SO_3H$, $SO_2NH_2$, $SO_2Me$, $NH_2$, COOH, $CONH_2$ and alkoxy.

As used herein the term "halo" or "halogeno" refers to F, Cl, Br or I.

Where there are two or more groups $R^8$ and/or $R^9$ these may be the same or different.

Where $R^8$ or $R^9$ comprises a neutral hydrophilic group (i) as hereinbefore defined, this preferably includes groups containing mono-, di- and polyhydroxylated saturated or unsaturated aliphatic, alicyclic or aromatic systems, carbohydrate derivatives, ethers and polyethers optionally containing one or more hydroxyl groups, O- and/or S-containing heterocyclic systems optionally containing one or more hydroxyl groups, aliphatic or aromatic systems containing a carboxamide, sulfoxide, sulfone, or sulfonamide function, and halogenated alkylcarbonyl groups.

Where $R^8$ or $R^9$ comprises an ionisable organic acid (ii) as hereinbefore defined, this preferably includes groups comprising one or more functional groups selected from —COOH, —$SO_3H$, —$OSO_3H$, —$PO_3H_2$, and —$OPO_3H_2$. It may be that $R^8$ or $R^9$ is one of these functional groups, or it may be that $R^8$ or $R^9$ is a group comprising one of these functional groups. For example, they may be alkyl groups, heteroalkyl groups or aryl groups (each of which may be as defined above) substituted with one or more functional groups selected from —COOH, —$SO_3H$, —$OSO_3H$, —$PO_3H_2$, and —$OPO_3H_2$.

Where $R^8$ or $R^9$ comprises an ionisable basic group (iii) as hereinbefore defined, this preferably includes aliphatic, alicyclic, aromatic, or heterocyclic groups comprising one or more of the functions —O—, —NH$_2$, —NH—, =N—, quaternary amine salts, guanidine, and amidine, optionally substituted by one or more substituents selected from halogen (e.g. F or Cl), SO$_2$-alkyl, alkyl optionally substituted by one or more OH or halogen groups, CHO, CO-alkyl, aralkyl, COO-alkyl and an ether group substituted by one or more OH groups.

In one embodiment $R^8$ and $R^9$ may consist of natural or unnatural amino acid residues and peptides, or their derivatives.

In one embodiment $R^8$ or $R^9$ is selected from
v) —OSO$_3$H, —PO$_3$H$_2$, —OPO$_3$H$_2$;
vi) Y' where Y' is selected from aliphatic, alicyclic, aromatic, or heterocyclic groups comprising one or more of the functions —O—, —NH$_2$, —NH—, =N—, amidine, optionally substituted by one or more substituents selected from halogen, SO$_2$alkyl, alkyl optionally substituted by one or more OH or halogen groups, COalkyl, aralkyl, COOalkyl and an ether group substituted by one or more OH groups;
(vii) NHCO(CH$_2$)$_m$[NHCO(CH$_2$)$_m$]$_p$[NHCO(CH$_2$)$_m$]$_q$Y' or NHCO(CH$_2$)$_t$NH(CH$_2$)$_t$Y' where p and q are each 0 or 1, and m, t and t' are each independently an integer from 1 to 10; and
(viii) (CH$_2$)$_n$NR$^{17}$COR$^{15}$, (CH$_2$)$_n$NR$^{18}$SO$_2$R$^{16}$, or SO$_2$R$^{19}$, where R$^{15}$, R$^{16}$ and R$^{19}$ are each alkyl groups optionally comprising one or more heteroatoms, and which are optionally substituted by one or more substituents selected from OH, NH$_2$, halogen and NO$_2$, R$^{17}$ and R$^{18}$ are each independently H or alkyl, and n and n' are each independently 0, 1, 2, or 3;
(ix) an ether or polyether optionally substituted by one or more hydroxyl groups or one or more Y' groups;
(x) (CH$_2$)$_r$NH$_2$; where r is 0, 1, 2, or 3;
(xi) (CH$_2$)$_{r'}$OH; where r' is 0, 1, 2, or 3;
(xii) (CH$_2$)$_{n''}$NR$^{20}$COR$^{21}$ where R$^{20}$ is H or alkyl, n'' is 0, 1, 2 or 3 and R$^{21}$ is an aryl or heteroaryl group, each of which may be optionally substituted by one or more substituents selected from halogeno, NO$_2$, OH, alkoxy, NH$_2$, COOH, CONH$_2$ and CF$_3$;
(xiii) SO$_2$NR$^{22}$R$^{23}$ where R$^{22}$ and R$^{23}$ are each independently H, alkyl, aralkyl, CO-alkyl or aryl, with the proviso that at least one of R$^{22}$ and R$^{23}$ is other than H, or R$^{22}$ and R$^{23}$ are linked to form a cyclic group optionally containing one or more heteroatoms selected from N, O and S, and wherein said alkyl, aryl or cyclic group is optionally substituted by one or more substituents selected from halogeno, NO$_2$, OH, alkoxy, NH$_2$, COOH, CH$_2$CO$_2$-alkyl, CONH$_2$ and CF$_3$;
(xiv) N-piperidinyl, piperidinyl, N-piperazinyl, N-diazepanyl, N-pyridinyl, N-pyrrolidinyl, N-morpholinyl or N-thiomorpholinyl, each of which may be optionally substituted by one or more alkyl, alkoxy, aryl, CHO or CO-alkyl groups.

In one preferred embodiment of the invention, each $R^8$ or $R^9$ is independently selected from a $C_{1-30}$ hydrocarbyl group, optionally comprising up to twelve heteroatoms selected from N, S, and O, and optionally bearing up to six substituents each independently selected from a group $R^{12}$ as hereinbefore defined or comprising a moiety $R^{11}$ as hereinbefore defined, and a group $R^{12}$.

Preferably in a compound of formula I as hereinbefore defined, up to six of the groups $R^1$ to $R^7$ and $R^{13}$ comprise a substituent $R^8$ as hereinbefore defined, each comprising one or more heteroatoms selected from N, S, and O, and alternatively or additionally each comprising one or more moieties $R^{11}$ or groups $R^{12}$ as hereinbefore defined, wherein the combined substituents comprise up to ten heteroatoms (which may suitably be atoms N, S and O).

Preferably $R^{10}$ is selected from $R^8$, alkyl, alkyl-$R^8$, alkylcycloalkyl which may be part unsaturated, cycloheteroalkyl, alkyl-cycloheteroalkyl, aryl, aryl-$R^8$, aralkyl, aralkyl-$R^8$, heteroaryl, alkyl-heteroaryl, halogeno, NO$_2$, CN, OH, O-alkyl, O-cycloalkyl which may be part unsaturated, O-aryl, O-heteroaryl, O—$R^8$, S-alkyl, NH$_2$, NH-alkyl, part unsaturated NH-cycloalkyl, NH-cycloheteroalkyl, NH-aryl, NH-heteroaryl, N-(alkyl)$_2$, N-(aryl)$_2$, N-(alkyl)(cycloalkyl), N-(alkyl)(cycloheteroalkyl), N-(alkyl)(aryl), N-(alkyl)(heteroaryl), NH—$R^8$, N—(R$^8$)(R$^9$), N-(alkyl)(R$^8$), N-(aryl) (R$^8$), NCHalkyl, NC(alkyl)$_2$, NC(alkyl)(R$^8$), NC(R$^8$)(R$^9$), COOH, COO—R$^8$, COO-alkyl, CONH$_2$, CONH-alkyl, CONH-aryl, CONH-heteroaryl, CON-(alkyl)(R$^8$), CON(aryl)(R$^8$), CON(heteroaryl)(R$^8$), CONH—R$^8$, CON—(R$^8$) (R$^9$), NHCO-alkyl, NHCO-aryl, NHCO-heteroaryl, NHCO—R$^8$, SO$_3$H, SO$_2$-alkyl, SO$_2$-alkyl-R$^8$, SO$_2$-aryl, SO$_2$-aryl-R$^8$, SO$_2$-heteroaryl, SO$_2$-heteroaryl-R$^8$, SO$_2$NH$_2$, SO$_2$NH—R$^8$, SO$_2$N—(R$^8$)(R$^9$), NHSO$_2$R$^8$, CF$_3$, CO—R$^8$, CO-alkyl, CO-alkyl-R$^8$, CO-cycloheteroalkyl, CO-aryl, CO-aryl-R$^8$, CO-heteroaryl, CO-heteroarylalkyl or CO-heteroarylR$^8$, wherein alkyl, aryl, aralkyl, heteroaryl groups may be further substituted with one or more groups selected from halogeno, NO$_2$, CN, OH, O-methyl, NH$_2$, COOH, CONH$_2$ and CF$_3$. Preferably a cycloheteroalkyl is a morpholino, piperazinyl or piperadinyl.

In a compound of formula I as hereinbefore defined, preferably
the heteroaryl is optionally substituted-pyridine, whereby:
  $X_1$ is N and $X_2$ and $X_3$ are CR$^{13}$, or
  $X_2$ is N and $X_1$ and $X_3$ are CR$^{13}$, or
  $X_3$ is N and $X_1$ and $X_2$ are CR$^{13}$; or
the heteroaryl is optionally substituted-pyridazine whereby $X_1$ and $X_2$ are N and $X_3$ is CR$^{13}$; or
the heteroaryl is optionally substituted-pyrimidine whereby $X_2$ and $X_3$ are N and $X_1$ is CR$^{13}$; or
the heteroaryl is optionally substituted-pyrazine whereby $X_1$ and $X_3$ are N and $X_2$ is CR$^{13}$.

More preferably the heteroaryl is optionally substituted-pyridine whereby
  $X_1$ is N and $X_2$ and $X_3$ are CR$^{13}$; or
  $X_2$ is N and $X_1$ and $X_3$ are CR$^{13}$; or
  $X_3$ is N and $X_1$ and $X_2$ are CR$^{13}$.

Preferably there is provided a compound of formula I'

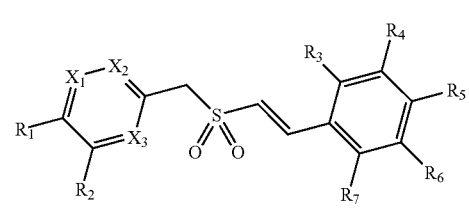

or a compound of formula I''

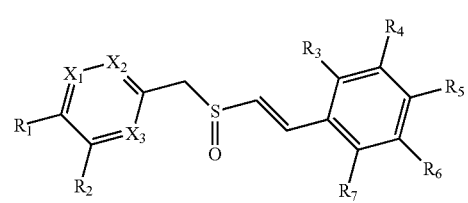

wherein all variables are as hereinbefore defined.

Suitably therefore, a compound of formula I' or I" comprises a substituted heteroaryl including pyridine, pyrimidine, pyridazine or pyrazine attached to a substituted (E)-(2-(ethylsulfonyl)vinyl)benzene or (E)-(2-(ethylsulfinyl)vinyl) benzene.

In one embodiment, there is provided a compound of formula I'a or I"a

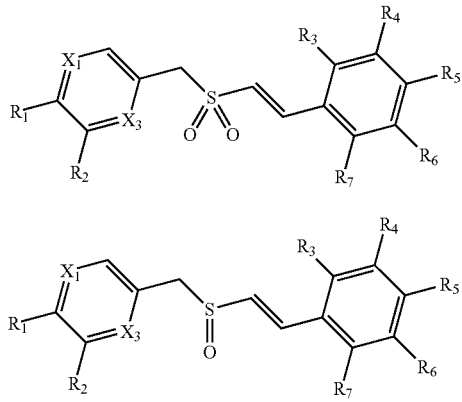

wherein all variables are as hereinbefore defined.

Preferably one of $X_1$ and $X_3$ is a nitrogen atom, the remaining one of $X_1$ and $X_3$ is $CR^{13}$, and the other substituent groups are as described above with reference to formula I. The compound of formula I'a or I"a may be provided in the form of its pharmaceutically acceptable salts or solvates and physiologically hydrolysable, solubilising or immobilisable derivatives. For example, it may be provided as a pharmaceutically acceptable salt or ester.

Preferably in the compounds of the present invention $R^1$, $R^2$ and $R^{13}$ are independently selected from: H, CN, $CF_3$, halogeno, OH, O-alkyl, O-cycloalkyl which may be part unsaturated, O-heteroaryl, S-alkyl, $C_{1-6}$ alkyl, alkyl-cycloalkyl which may be part unsaturated, aryl, cycloheteroalkyl, alkylcycloheteroalkyl such as $CH_2$-cycloheteroalkyl, heteroaryl, alkyl-heteroaryl such as $CH_2$-heteroaryl, $NO_2$, $NH_2$, NH-alkyl, N(alkyl)$_2$, N-(alkyl)($R^8$), part unsaturated NH-cycloalkyl, NH-cycloheteroalkyl, NH-heteroaryl, NHCOalkyl, NHalkylCOOH, $NHSO_2$alkyl, $NHSO_2R^8$, NCHalkyl, NC(alkyl)$_2$, NC(alkyl)($R^8$), NC($R^8$)($R^9$), $CONH_2$, CONH-(alkyl), CONH-(heteroaryl), CON-(alkyl)($R^8$), $R^8$, $CO_2$alkyl, CO-alkyl, CO-cycloheteroalkyl, CO-heteroaryl, CONH-heteroaryl; wherein alkyl, cycloheteroalkyl, aryl, aralkyl, heteroaryl groups may be further substituted with one or more groups selected from halogeno, $NO_2$, CN OH, O-methyl, $NH_2$, COOH, $CONH_2$ and $CF_3$.

More preferably $R^1$, $R^2$ and $R^{13}$ are selected from H, $C_{1-6}$ alkyl, $R^8$, OH, $OC_{1-6}$ alkyl, halogeno, $NO_2$, $NH_2$, $NHCH_3$, NH-alkyl, NHalkylCOOH, N(alkyl)$_2$, N-(alkyl)($R^8$), part unsaturated NH-cycloalkyl, NH-cycloheteroalkyl, NH-heteroaryl, $NHSO_2R^8$, $NHSO_2CH_3$, $CO_2$alkyl, CO-alkyl, $CONH_2$, CONH-alkyl and heteroaryl.

More preferably $R^1$ is selected from $CH_3$, $OCH_3$, $OCH_2CH_3$, O-propyl, O-butyl, halogeno, $NH_2$, NH-alkyl, N(alkyl)$_2$, $CO_2$alkyl, CO-alkyl, $CONH_2$, CONH-alkyl and heteroaryl.

More preferably $R^2$ is selected from $CH_3$, $OCH_3$, $OCH_2CH_3$, OH, halogeno, $NO_2$, $NH_2$, NH-alkyl, NHalkyl-COOH, N(alkyl)$_2$, N-(alkyl)($R^8$), part unsaturated NH-cycloalkyl, NH-cycloheteroalkyl, NH-heteroaryl and $NHSO_2R^8$.

More preferably $R^{13}$ is selected from H and $C_{1-3}$ alkyl.

It may be that $R^1$, $R^2$ and $R^{13}$ are selected from H, $C_{1-6}$ alkyl, OH, $OC_{1-6}$ alkyl, halogeno, $NO_2$, $NH_2$, $NHCH_3$, NH-alkyl, NHalkylCOOH, N(alkyl)$_2$, part unsaturated NH-cycloalkyl, NH-cycloheteroalkyl, NH-heteroaryl, $NHSO_2$alkyl, $NHSO_2$haloalkyl, $CO_2$alkyl, CO-alkyl, $CONH_2$, CONH-alkyl, $OCH_2CH_2$Oalkyl, $OCH_2CH_3$N(alkyl)$_2$, NHC(=O)alkyl NHalkylC(=O)$NH_2$, NHalkylC(=O)alkyl, cycloheteroalkyl, heteroaryl, and NH-cycloheteroalkyl substituted with $SO_2$ alkyl or heteroalkyl.

$R^2$ may be selected from $CH_3$, $OCH_3$, $OCH_2CH_3$, $OCH_2CH_2$Oalkyl, $OCH_2CH_3$N(alkyl)$_2$, OH, halogeno, $NO_2$, $NH_2$, NH-alkyl, NHC(=O)alkyl, NHalkylCOOH, NHalkylC(=O)$NH_2$, NHalkylC(=O)alkyl, NHalkyl, N(alkyl)$_2$, cycloheteroalkyl, part unsaturated NH-cycloalkyl, NH-heteroaryl, $NHSO_2$alkyl, $NHSO_2$haloalkyl, NH-cycloheteroalkyl, and NH-cycloheteroalkyl substituted with $SO_2$ alkyl or heteroalkyl.

Preferably each $R^3$ or $R^7$ is independently selected from $OC_{1-6}$ alkyl, S-alkyl, $C_{1-6}$alkyl, $NH_2$, NH-alkyl, N(alkyl)$_2$, and NHCO-alkyl, $SO_2$-cycloheteroalkyl, $SO_2$-heteroaryl, SO-cycloheteroalkyl, SO-heteroaryl, $CO_2$alkyl, $CONH_2$, CONH-alkyl, CONH-heteroaryl, CO-alkyl, CO-cycloheteroalkyl or CO-heteroaryl; preferably, the cycloheteroalkyl group is a N-alkyl-morpholine, N-alkylpiperazine, N-alkylpiperadine; or $CF_3$, halogeno, CN, $NO_2$ or OH.

More preferably each $R^3$ or $R^7$ is independently selected from $C_{1-4}$ alkyl, CN, $CF_3$, halogeno, $NO_2$, O-methyl, O-ethyl, O-propyl, O-butyl, S-alkyl, $NH_2$, NH-alkyl, N(alkyl)$_2$, $CO_2$alkyl, CO-alkyl, $CONH_2$, CONH-alkyl and heteroaryl.

Preferably $R^4$, $R^5$ and $R^6$ are independently selected from H, $R^8$, $NH_2$, NH-alkyl, N(alkyl)$_2$, halogeno, OH, O-alkyl, S-alkyl, a O-alkyl, S-alkyl, sulphonyl, sulphinyl, carbonyl, amide or sulphonamide, or thioether link to an unsubstituted or substituted 6 membered cyclic or heterocyclic, or aromatic or heteroaromatic ring, wherein substituents are as hereinbefore defined.

More preferably $R^4$, $R^5$ and $R^6$ are independently selected from H, $R^8$, O-alkyl, S-alkyl, $SO_2$-cycloheteroalkyl, $SO_2$-cycloalkyl, $SO_2$-heteroaryl, SO-cycloheteroalkyl, SO-cycloalkyl, SO-heteroaryl, CO-cycloheteroalkyl, CO-cycloalkyl, CO-heteroaryl, CO-heteroarylalkyl, N-(alkyl)(cycloalkyl), N-(alkyl)(cycloheteroalkyl), or N-(alkyl)(heteroaryl) more preferably wherein the cycloheteroalkyl is heteroatom linked and may be unsubstituted or substituted comprising one, two or three heteroatoms selected from N, O, S. More preferably a cycloheteroalkyl is a N-alkyl-morpholino, N-alkyl-piperazine or N-alkyl-piperadine.

It may be that $R^4$, $R^5$ and $R^6$ are independently selected from H, O-alkyl, S-alkyl, $SO_2$-cycloheteroalkyl, $SO_2$-cycloalkyl, $SO_2$-heteroaryl, SO-cycloheteroalkyl, SO-cycloalkyl, SO-heteroaryl, CO-cycloheteroalkyl, CO-cycloalkyl, CO-heteroaryl, CO-heteroarylalkyl, N-(alkyl)(cycloalkyl), N-(alkyl)(cycloheteroalkyl), or N-(alkyl)(heteroaryl); wherein preferably the cycloheteroalkyl is heteroatom linked and may be unsubstituted or substituted comprising one, two or three heteroatoms selected from N, O, S. More preferably a cycloheteroalkyl is a N-alkyl-morpholino, N-alkyl-piperazine or N-alkyl-piperadine.

More preferably $R^4$, $R^5$ and $R^6$ are independently selected from H, $R^8$, O-alkyl, N-linked N-(alkyl)(cycloheteroalkyl), $SO_2$-cycloheteroalkyl and CO-cycloheteroalkyl, most preferably such as N-(alkyl)(morpholino), N-(alkyl)(piperazine), N-(alkyl)(piperadine), $SO_2$-piperazines, $SO_2$-morpholines, CO-piperazines, CO-morpholines, CO-piperadine and the like.

It may be that $R^4$, $R^5$ and $R^6$ are independently selected from H, O-alkyl, N-linked N-(alkyl)(cycloheteroalkyl), $SO_2$-cycloheteroalkyl and CO-cycloheteroalkyl.

Preferably at least two, more preferably at least three of $R^3$ to $R^7$ are independently selected from $OC_{1-6}$ alkyl, more preferably, O-methyl, O-ethyl, O-propyl, O-butyl. More preferably $R^3$, $R^5$ and $R^7$ are independently selected from $OC_{1-6}$ alkyl, more preferably, O-methyl, O-ethyl, O-propyl and O-butyl, most preferably are O-methyl.

It may be that $R^4$ and $R^6$ are independently selected from H, $R^8$, O-alkyl, N-linked N-(alkyl)(cycloheteroalkyl), $SO_2$-cycloheteroalkyl and CO-cycloheteroalkyl, most preferably such as N-(alkyl)(morpholino), N-(alkyl)(piperazine), N-(alkyl)(piperadine), $SO_2$-piperazines, $SO_2$-morpholines, CO-piperazines, CO-morpholines, CO-piperadine and the like. Preferably $R^4$ and $R^6$ are independently selected from H, $R^8$, N-linked N-(alkyl)(cycloheteroalkyl), $SO_2$-cycloheteroalkyl and CO-cycloheteroalkyl, most preferably such as N-(alkyl)(morpholino), N-(alkyl)(piperazine), N-(alkyl)(piperadine), $SO_2$-piperazines, $SO_2$-morpholines, CO-piperazines, CO-morpholines, CO-piperadine and the like. It may be that $R^4$ and $R^6$ are independently selected from H, O-alkyl, N-linked N-(alkyl)(cycloheteroalkyl), $SO_2$-cycloheteroalkyl and CO-cycloheteroalkyl, Preferably $R^4$ and $R^6$ are independently selected from H, N-linked N-(alkyl)(cycloheteroalkyl), $SO_2$-cycloheteroalkyl and CO-cycloheteroalkyl, most preferably such as N-(alkyl)(morpholino), N-(alkyl)(piperazine), N-(alkyl)(piperadine), $SO_2$-piperazines, $SO_2$-morpholines, CO-piperazines, CO-morpholines, CO-piperadine and the like. In one embodiment, $R^4$ and $R^6$ are both H.

Preferably up to six of $R^1$, $R^2$, $R^3$, $R^4$, $R^5$, $R^6$, $R^7$, $R^{10}$ and $R^{14}$, for example one, two, three or four thereof, correspond to or comprise one or more of the group $R^8$ or $R^9$.

Preferably at least one of $R^1$, $R^2$, $R^4$, $R^5$ or $R^6$; $R^1$, $R^2$, $R^3$, or $R^7$; or $R^3$, $R^4$, $R^5$, $R^6$ and $R^7$ comprises or contains a solubilising moiety $R^8$ or $R^9$, More preferably either or both of $R^3$ and $R^7$; or at least one of $R^2$, $R^4$, $R^5$ or $R^6$ comprises or contains a solubilising moiety $R^8$ or $R^9$.

Preferred compounds of formula I'

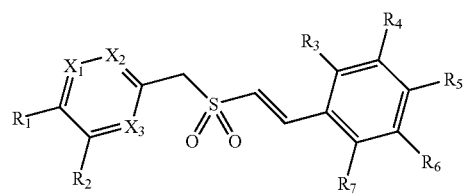

and formula I"

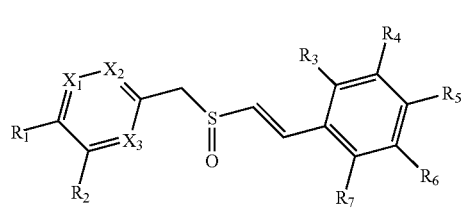

of the invention include, but are not limited to, those detailed in the table below, and pharmaceutically acceptable salts or solvates and physiologically hydrolysable, solubilising or immobilisable derivatives thereof (e.g. pharmaceutically acceptable salts and esters thereof):

| $X^1$ | $X^2$ | $X^3$ | $R_1$ | $R_2$ | $R_3$ | $R_4$ | $R_5$ | $R_6$ | $R_7$ |
|---|---|---|---|---|---|---|---|---|---|
| N | CH | CH | OMe | $NO_2$ | OMe | H | OMe | H | OMe |
| N | CH | CH | OMe | $NH_2$ | OMe | H | OMe | H | OMe |
| N | CH | CH | OMe | NHMe | OMe | H | OMe | H | OMe |
| N | CH | CH | OMe | NHCOMe | OMe | H | OMe | H | OMe |
| N | CH | CH | OMe | NHEt | OMe | H | OMe | H | OMe |
| N | CH | CH | OMe | $NMe_2$ | OMe | H | OMe | H | OMe |
| N | CH | CH | OMe | $NEt_2$ | OMe | H | OMe | H | OMe |
| N | CH | CH | OMe | NMeCOMe | OMe | H | OMe | H | OMe |
| N | CH | CH | OMe | NEtCOMe | OMe | H | OMe | H | OMe |
| N | CH | CH | OMe | $NHCH_2COEt$ | OMe | H | OMe | H | OMe |
| N | CH | CH | OMe | $NHCH_2CO_2Et$ | OMe | H | OMe | H | OMe |
| N | CH | CH | OMe | $NHCH_2COMe$ | OMe | H | OMe | H | OMe |
| N | CH | CH | OMe | $NHCH_2CO_2Me$ | OMe | H | OMe | H | OMe |
| N | CH | CH | OMe | $NHCH(Me)CO_2H$ | OMe | H | OMe | H | OMe |
| N | CH | CH | OMe | $NHCH_2CO_2H$ | OMe | H | OMe | H | OMe |
| N | CH | CH | OMe | $NHCH_2CONH_2$ | OMe | H | OMe | H | OMe |
| N | CH | CH | OMe | $NHSO_2Me$ | OMe | H | OMe | H | OMe |
| N | CH | CH | OMe | $NHSO_2CF_3$ | OMe | H | OMe | H | OMe |
| N | CH | CH | OMe | $NHCH_2CH_2NEt_2$ | OMe | H | OMe | H | OMe |
| N | CH | CH | OMe | $NHCH_2CH_2NEt_2$ | OMe | H | OMe | H | OMe |
| N | CH | CH | OMe | OH | OMe | H | OMe | H | OMe |
| N | CH | CH | OMe | OMe | OMe | H | OMe | H | OMe |
| N | CH | CH | OMe | $OCH_2CH_2OMe$ | OMe | H | OMe | H | OMe |
| N | CH | CH | OMe | $OCH_2CH_2NEt_2$ | OMe | H | OMe | H | OMe |
| N | CH | CH | OMe | HN–⟨piperidine⟩–N— | OMe | H | OMe | H | OMe |

-continued

| X¹ | X² | X³ | R₁ | R₂ | R₃ | R₄ | R₅ | R₆ | R₇ |
|---|---|---|---|---|---|---|---|---|---|
| N | CH | CH | OMe | HN—⟨piperidine⟩—N—S(=O)(=O)Me | OMe | H | OMe | H | OMe |
| N | CH | CH | OMe | ⟨piperidine, N-linked⟩ | OMe | H | OMe | H | OMe |
| N | CH | CH | OMe | ⟨piperazine, NH⟩ | OMe | H | OMe | H | OMe |
| N | CH | CH | OMe | HN—⟨piperidine⟩—N(CH₂CH₂)NMe₂ | OMe | H | OMe | H | OMe |
| N | CH | CH | OMe | HN—⟨piperidine⟩—N(CH₂CH₂)NEt₂ | OMe | H | OMe | H | OMe |
| N | CH | CH | OMe | NO₂ | OMe | H | F | H | H |
| N | CH | CH | OMe | NH₂ | OMe | H | CN | H | H |
| N | CH | CH | OMe | NO₂ | OMe | H | H | H | OMe |
| N | CH | CH | OMe | NH₂ | OMe | H | H | H | OMe |
| N | CH | CH | OMe | NHMe | OMe | H | H | H | OMe |
| N | CH | CH | OMe | NHCOMe | OMe | H | H | H | OMe |
| N | CH | CH | OMe | NHEt | OMe | H | H | H | OMe |
| N | CH | CH | OMe | NMe₂ | OMe | H | H | H | OMe |
| N | CH | CH | OMe | NEt₂ | OMe | H | H | H | OMe |
| N | CH | CH | OMe | NMeCOMe | OMe | H | H | H | OMe |
| N | CH | CH | OMe | NEtCOMe | OMe | H | H | H | OMe |
| N | CH | CH | OMe | NHCH₂COEt | OMe | H | H | H | OMe |
| N | CH | CH | OMe | NHCH₂CO₂Et | OMe | H | H | H | OMe |
| N | CH | CH | OMe | NHCH₂COMe | OMe | H | H | H | OMe |
| N | CH | CH | OMe | NHCH₂CO₂Me | OMe | H | H | H | OMe |
| N | CH | CH | OMe | NHCH(Me)CO₂H | OMe | H | H | H | OMe |
| N | CH | CH | OMe | NHCH₂CO₂H | OMe | H | H | H | OMe |
| N | CH | CH | OMe | NHCH₂CONH₂ | OMe | H | H | H | OMe |
| N | CH | CH | OMe | NHSO₂Me | OMe | H | H | H | OMe |
| N | CH | CH | OMe | NHSO₂CF₃ | OMe | H | H | H | OMe |
| N | CH | CH | OMe | NHCH₂CH₂NEt₂ | OMe | H | H | H | OMe |
| N | CH | CH | OMe | OH | OMe | H | H | H | OMe |
| N | CH | CH | OMe | OMe | OMe | H | H | H | OMe |
| N | CH | CH | OMe | OCH₂CH₂OMe | OMe | H | H | H | OMe |
| N | CH | CH | OMe | OCH₂CH₂NEt₂ | OMe | H | H | H | OMe |
| N | CH | CH | OMe | HN—⟨piperidine⟩—N—Me | OMe | H | H | H | OMe |
| N | CH | CH | OMe | HN—⟨piperidine⟩—N—S(=O)(=O)Me | OMe | H | H | H | OMe |
| N | CH | CH | OMe | ⟨piperidine, N-linked⟩ | OMe | H | H | H | OMe |
| N | CH | CH | OMe | ⟨piperazine, NH⟩ | OMe | H | H | H | OMe |

-continued

| $X^1$ | $X^2$ | $X^3$ | $R_1$ | $R_2$ | $R_3$ | $R_4$ | $R_5$ | $R_6$ | $R_7$ |
|---|---|---|---|---|---|---|---|---|---|
| N | CH | CH | OMe | 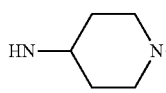 | OMe | H | OMe | H | OMe |
| N | CH | CH | OMe | 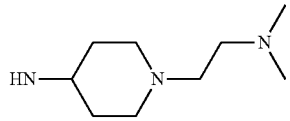 | OMe | H | H | H | OMe |
| N | CH | CH | OMe | 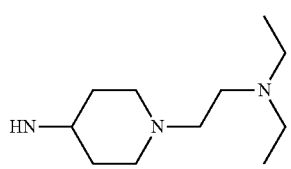 | OMe | H | H | H | OMe |
| CH | CH | N | OMe | $NO_2$ | OMe | H | OMe | H | OMe |
| CH | CH | N | OMe | $NH_2$ | OMe | H | OMe | H | OMe |
| CH | CH | N | OMe | NHMe | OMe | H | OMe | H | OMe |
| CH | CH | N | OMe | NHCOMe | OMe | H | OMe | H | OMe |
| CH | CH | N | OMe | NHEt | OMe | H | OMe | H | OMe |
| CH | CH | N | OMe | $NMe_2$ | OMe | H | OMe | H | OMe |
| CH | CH | N | OMe | $NEt_2$ | OMe | H | OMe | H | OMe |
| CH | CH | N | OMe | NMeCOMe | OMe | H | OMe | H | OMe |
| CH | CH | N | OMe | NEtCOMe | OMe | H | OMe | H | OMe |
| CH | CH | N | OMe | $NHCH_2COEt$ | OMe | H | OMe | H | OMe |
| CH | CH | N | OMe | $NHCH_2CO_2Et$ | OMe | H | OMe | H | OMe |
| CH | CH | N | OMe | $NHCH_2COMe$ | OMe | H | OMe | H | OMe |
| CH | CH | N | OMe | $NHCH_2CO_2Me$ | OMe | H | OMe | H | OMe |
| CH | CH | N | OMe | $NHCH(Me)CO_2H$ | OMe | H | OMe | H | OMe |
| CH | CH | N | OMe | $NHCH_2CO_2H$ | OMe | H | OMe | H | OMe |
| CH | CH | N | OMe | $NHCH_2CONH_2$ | OMe | H | OMe | H | OMe |
| CH | CH | N | OMe | $NHSO_2Me$ | OMe | H | OMe | H | OMe |
| CH | CH | N | OMe | $NHSO_2CF_3$ | OMe | H | OMe | H | OMe |
| CH | CH | N | OMe | $NHCH_2CH_2NEt_2$ | OMe | H | OMe | H | OMe |
| CH | CH | N | OMe | OH | OMe | H | OMe | H | OMe |
| CH | CH | N | OMe | OMe | OMe | H | OMe | H | OMe |
| CH | CH | N | OMe | $OCH_2CH_2OMe$ | OMe | H | OMe | H | OMe |
| CH | CH | N | OMe | $OCH_2CH_2NEt_2$ | OMe | H | OMe | H | OMe |
| CH | CH | N | OMe | 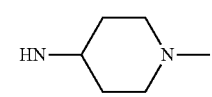 | OMe | H | OMe | H | OMe |
| CH | CH | N | OMe | 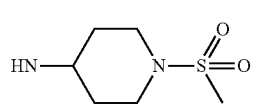 | OMe | H | OMe | H | OMe |
| CH | CH | N | OMe | 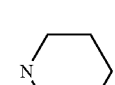 | OMe | H | OMe | H | OMe |
| CH | CH | N | OMe | 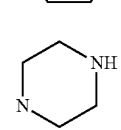 | OMe | H | OMe | H | OMe |
| CH | CH | N | OMe |  | OMe | H | OMe | H | OMe |

-continued

| X¹ | X² | X³ | R₁ | R₂ | R₃ | R₄ | R₅ | R₆ | R₇ |
|---|---|---|---|---|---|---|---|---|---|
| CH | CH | N | OMe | 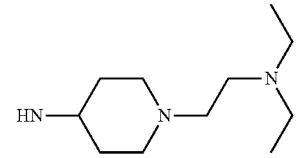 | OMe | H | OMe | H | OMe |
| CH | CH | N | OMe | NO₂ | OMe | H | H | H | OMe |
| CH | CH | N | OMe | NH₂ | OMe | H | H | H | OMe |
| CH | CH | N | OMe | NHMe | OMe | H | H | H | OMe |
| CH | CH | N | OMe | NHCOMe | OMe | H | OMe | H | OMe |
| CH | CH | N | OMe | NHEt | OMe | H | H | H | OMe |
| CH | CH | N | OMe | NMe₂ | OMe | H | H | H | OMe |
| CH | CH | N | OMe | NEt₂ | OMe | H | H | H | OMe |
| CH | CH | N | OMe | NMeCOMe | OMe | H | H | H | OMe |
| CH | CH | N | OMe | NEtCOMe | OMe | H | H | H | OMe |
| CH | CH | N | OMe | NHCH₂COEt | OMe | H | H | H | OMe |
| CH | CH | N | OMe | NHCH₂CO₂Et | OMe | H | H | H | OMe |
| CH | CH | N | OMe | NHCH₂COMe | OMe | H | H | H | OMe |
| CH | CH | N | OMe | NHCH₂CO₂Me | OMe | H | H | H | OMe |
| CH | CH | N | OMe | NHCH(Me)CO₂H | OMe | H | H | H | OMe |
| CH | CH | N | OMe | NHCH₂CO₂H | OMe | H | H | H | OMe |
| CH | CH | N | OMe | NHCH₂CONH₂ | OMe | H | H | H | OMe |
| CH | CH | N | OMe | NHSO₂Me | OMe | H | H | H | OMe |
| CH | CH | N | OMe | NHSO₂CF₃ | OMe | H | H | H | OMe |
| CH | CH | N | OMe | NHCH₂CH₂NEt₂ | OMe | H | H | H | OMe |
| CH | CH | N | OMe | OH | OMe | H | H | H | OMe |
| CH | CH | N | OMe | OMe | OMe | H | H | H | OMe |
| CH | CH | N | OMe | OCH₂CH₂OMe | OMe | H | H | H | OMe |
| CH | CH | N | OMe | OCH₂CH₂NEt₂ | OMe | H | H | H | OMe |
| CH | CH | N | OMe | 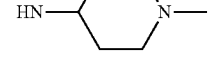 | OMe | H | H | H | OMe |
| CH | CH | N | OMe | 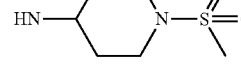 | OMe | H | H | H | OMe |
| CH | CH | N | OMe |  | OMe | H | H | H | OMe |
| CH | CH | N | OMe | 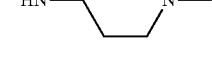 | OMe | H | H | H | OMe |
| CH | CH | N | OMe | 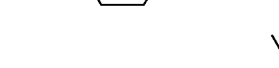 | OMe | H | H | H | OMe |
| CH | CH | N | OMe | 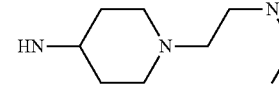 | OMe | H | H | H | OMe |
| CH | CH | N | OMe | NO₂ | H | H | F | H | H |
| CH | CH | N | OMe | NH₂ | H | H | CN | H | H |
| CH | N | N | OMe | NO₂ | OMe | H | OMe | H | OMe |
| CH | N | N | OMe | NH₂ | OMe | H | OMe | H | OMe |
| CH | N | N | OMe | NHMe | OMe | H | OMe | H | OMe |

-continued

| X¹ | X² | X³ | R₁ | R₂ | R₃ | R₄ | R₅ | R₆ | R₇ |
|---|---|---|---|---|---|---|---|---|---|
| CH | N | N | OMe | NHCOMe | OMe | H | OMe | H | OMe |
| CH | N | N | OMe | NHEt | OMe | H | OMe | H | OMe |
| CH | N | N | OMe | NMe₂ | OMe | H | OMe | H | OMe |
| CH | N | N | OMe | NEt₂ | OMe | H | OMe | H | OMe |
| CH | N | N | OMe | NMeCOMe | OMe | H | OMe | H | OMe |
| CH | N | N | OMe | NEtCOMe | OMe | H | OMe | H | OMe |
| CH | N | N | OMe | NHCH₂COEt | OMe | H | OMe | H | OMe |
| CH | N | N | OMe | NHCH₂CO₂Et | OMe | H | OMe | H | OMe |
| CH | N | N | OMe | NHCH₂COMe | OMe | H | OMe | H | OMe |
| CH | N | N | OMe | NHCH₂CO₂Me | OMe | H | OMe | H | OMe |
| CH | N | N | OMe | NHCH(Me)CO₂H | OMe | H | OMe | H | OMe |
| CH | N | N | OMe | NHCH₂CO₂H | OMe | H | OMe | H | OMe |
| CH | N | N | OMe | NHCH₂CONH₂ | OMe | H | OMe | H | OMe |
| CH | N | N | OMe | NHSO₂Me | OMe | H | OMe | H | OMe |
| CH | N | N | OMe | NHSO₂CF₃ | OMe | H | OMe | H | OMe |
| CH | N | N | OMe | NHCH₂CH₂NEt₂ | OMe | H | OMe | H | OMe |
| CH | N | N | OMe | OH | OMe | H | OMe | H | OMe |
| CH | N | N | OMe | OMe | OMe | H | OMe | H | OMe |
| CH | N | N | OMe | OCH₂CH₂OMe | OMe | H | OMe | H | OMe |
| CH | N | N | OMe | OCH₂CH₂NEt₂ | OMe | H | OMe | H | OMe |
| CH | N | N | OMe | 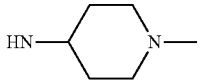 | OMe | H | OMe | H | OMe |
| CH | N | N | OMe | 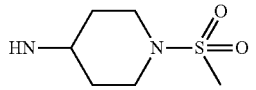 | OMe | H | OMe | H | OMe |
| CH | N | N | OMe | 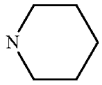 | OMe | H | OMe | H | OMe |
| CH | N | N | OMe | 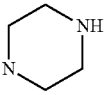 | OMe | H | OMe | H | OMe |
| CH | N | N | OMe | 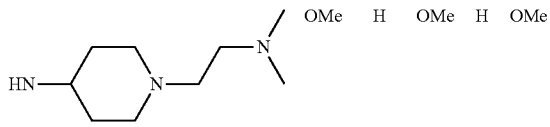 | OMe | H | OMe | H | OMe |
| CH | N | N | OMe | 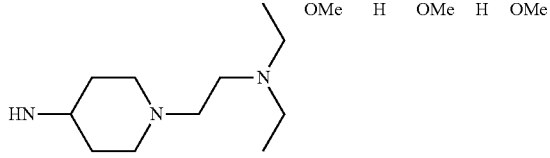 | OMe | H | OMe | H | OMe |
| N | N | CH | OMe | NO₂ | OMe | H | OMe | H | OMe |
| N | N | CH | OMe | NH₂ | OMe | H | OMe | H | OMe |
| N | N | CH | OMe | NHMe | OMe | H | OMe | H | OMe |
| N | N | CH | OMe | NHCOMe | OMe | H | OMe | H | OMe |
| N | N | CH | OMe | NHEt | OMe | H | OMe | H | OMe |
| N | N | CH | OMe | NMe₂ | OMe | H | OMe | H | OMe |
| N | N | CH | OMe | NEt₂ | OMe | H | OMe | H | OMe |
| N | N | CH | OMe | NMeCOMe | OMe | H | OMe | H | OMe |
| N | N | CH | OMe | NEtCOMe | OMe | H | OMe | H | OMe |
| N | N | CH | OMe | NHCH₂COEt | OMe | H | OMe | H | OMe |
| N | N | CH | OMe | NHCH₂CO₂Et | OMe | H | OMe | H | OMe |
| N | N | CH | OMe | NHCH₂COMe | OMe | H | OMe | H | OMe |
| N | N | CH | OMe | NHCH₂CO₂Me | OMe | H | OMe | H | OMe |
| N | N | CH | OMe | NHCH(Me)CO₂H | OMe | H | OMe | H | OMe |
| N | N | CH | OMe | NHCH₂CO₂H | OMe | H | OMe | H | OMe |
| N | N | CH | OMe | NHCH₂CONH₂ | OMe | H | OMe | H | OMe |
| N | N | CH | OMe | NHSO₂Me | OMe | H | OMe | H | OMe |
| N | N | CH | OMe | NHSO₂CF₃ | OMe | H | OMe | H | OMe |
| N | N | CH | OMe | NHCH₂CH₂NEt₂ | OMe | H | OMe | H | OMe |
| N | N | CH | OMe | OH | OMe | H | OMe | H | OMe |
| N | N | CH | OMe | OMe | OMe | H | OMe | H | OMe |

-continued

| X¹ | X² | X³ | R₁ | R₂ | R₃ | R₄ | R₅ | R₆ | R₇ |
|---|---|---|---|---|---|---|---|---|---|
| N | N | CH | OMe | OCH₂CH₂OMe | OMe | H | OMe | H | OMe |
| N | N | CH | OMe | OCH₂CH₂NEt₂ | OMe | H | OMe | H | OMe |
| N | N | CH | OMe | HN-(4-(N-methylpiperidinyl)) | OMe | H | OMe | H | OMe |
| N | N | CH | OMe | HN-(4-(N-methylsulfonylpiperidinyl)) | OMe | H | OMe | H | OMe |
| N | N | CH | OMe | piperidin-1-yl | OMe | H | OMe | H | OMe |
| N | N | CH | OMe | piperazin-1-yl | OMe | H | OMe | H | OMe |
| N | N | CH | OMe | HN-(1-(2-(dimethylamino)ethyl)piperidin-4-yl) | OMe | H | OMe | H | OMe |
| N | N | CH | OMe | HN-(1-(2-(diethylamino)ethyl)piperidin-4-yl) | OMe | H | OMe | H | OMe |
| N | CH | N | OMe | NO₂ | OMe | H | OMe | H | OMe |
| N | CH | N | OMe | NH₂ | OMe | H | OMe | H | OMe |
| N | CH | N | OMe | NHMe | OMe | H | OMe | H | OMe |
| N | CH | N | OMe | NHCOMe | OMe | H | OMe | H | OMe |
| N | CH | N | OMe | NHEt | OMe | H | OMe | H | OMe |
| N | CH | N | OMe | NMe₂ | OMe | H | OMe | H | OMe |
| N | CH | N | OMe | NEt₂ | OMe | H | OMe | H | OMe |
| N | CH | N | OMe | NMeCOMe | OMe | H | OMe | H | OMe |
| N | CH | N | OMe | NEtCOMe | OMe | H | OMe | H | OMe |
| N | CH | N | OMe | NHCH₂COEt | OMe | H | OMe | H | OMe |
| N | CH | N | OMe | NHCH₂CO₂Et | OMe | H | OMe | H | OMe |
| N | CH | N | OMe | NHCH₂COMe | OMe | H | OMe | H | OMe |
| N | CH | N | OMe | NHCH₂CO₂Me | OMe | H | OMe | H | OMe |
| N | CH | N | OMe | NHCH(Me)CO₂H | OMe | H | OMe | H | OMe |
| N | CH | N | OMe | NHCH₂CO₂H | OMe | H | OMe | H | OMe |
| N | CH | N | OMe | NHCH₂CONH₂ | OMe | H | OMe | H | OMe |
| N | CH | N | OMe | NHSO₂Me | OMe | H | OMe | H | OMe |
| N | CH | N | OMe | NHSO₂CF₃ | OMe | H | OMe | H | OMe |
| N | CH | N | OMe | NHCH₂CH₂NEt₂ | OMe | H | OMe | H | OMe |
| N | CH | N | OMe | OH | OMe | H | OMe | H | OMe |
| N | CH | N | OMe | OMe | OMe | H | OMe | H | OMe |
| N | CH | N | OMe | OCH₂CH₂OMe | OMe | H | OMe | H | OMe |
| N | CH | N | OMe | OCH₂CH₂NEt₂ | OMe | H | OMe | H | OMe |
| N | CH | N | OMe | HN-(4-(N-methylpiperidinyl)) | OMe | H | OMe | H | OMe |
| N | CH | N | OMe | HN-(4-(N-methylsulfonylpiperidinyl)) | OMe | H | OMe | H | OMe |
| N | CH | N | OMe | piperidin-1-yl | OMe | H | OMe | H | OMe |

-continued

| X¹ | X² | X³ | R₁ | R₂ | R₃ | R₄ | R₅ | R₆ | R₇ |
|---|---|---|---|---|---|---|---|---|---|
| N | CH | N | OMe | 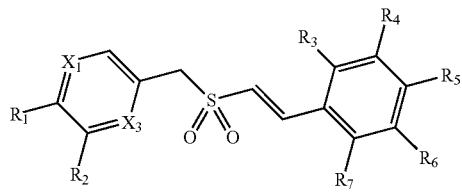 | OMe | H | OMe | H | OMe |
| N | CH | N | OMe | | OMe | H | OMe | H | OMe |
| N | CH | N | OMe | | OMe | H | OMe | H | OMe |

Preferred compounds of formula I'a or I"a

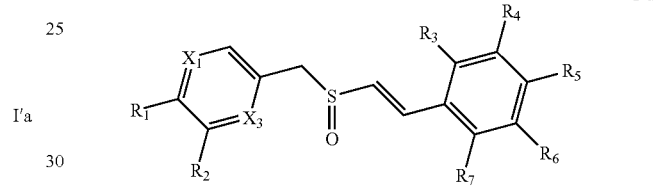

of the invention include, but are not limited to, those detailed in the table below, and pharmaceutically acceptable salts or solvates and physiologically hydrolysable, solubilising or immobilisable derivatives thereof (e.g. pharmaceutically acceptable salts and esters thereof):

| X¹ | X³ | R₁ | R₂ | R₃ | R₄ | R₅ | R₆ | R₇ |
|---|---|---|---|---|---|---|---|---|
| N | CH | OMe | NO₂ | OMe | H | OMe | H | OMe |
| N | CH | OMe | NH₂ | OMe | H | OMe | H | OMe |
| N | CH | OMe | NHMe | OMe | H | OMe | H | OMe |
| N | CH | OMe | NHCOMe | OMe | H | OMe | H | OMe |
| N | CH | OMe | NHEt | OMe | H | OMe | H | OMe |
| N | CH | OMe | NMe₂ | OMe | H | OMe | H | OMe |
| N | CH | OMe | NEt₂ | OMe | H | OMe | H | OMe |
| N | CH | OMe | NMeCOMe | OMe | H | OMe | H | OMe |
| N | CH | OMe | NEtCOMe | OMe | H | OMe | H | OMe |
| N | CH | OMe | NHCH₂COEt | OMe | H | OMe | H | OMe |
| N | CH | OMe | NHCH₂CO₂Et | OMe | H | OMe | H | OMe |
| N | CH | OMe | NHCH₂COMe | OMe | H | OMe | H | OMe |
| N | CH | OMe | NHCH₂CO₂Me | OMe | H | OMe | H | OMe |
| N | CH | OMe | NHCH₂CO₂H | OMe | H | OMe | H | OMe |
| N | CH | OMe | NHCH₂CONH₂ | OMe | H | OMe | H | OMe |
| N | CH | OMe | NHSO₂Me | OMe | H | OMe | H | OMe |
| N | CH | OMe | NHSO₂CF₃ | OMe | H | OMe | H | OMe |
| N | CH | OMe | NHCH₂CH₂NEt₂ | OMe | H | OMe | H | OMe |
| N | CH | OMe | | OMe | H | OMe | H | OMe |
| N | CH | OMe | | OMe | H | OMe | H | OMe |

-continued

| X¹ | X³ | R₁ | R₂ | R₃ | R₄ | R₅ | R₆ | R₇ |
|---|---|---|---|---|---|---|---|---|
| N | CH | OMe |  | OMe | H | OMe | H | OMe |
| N | CH | OMe | 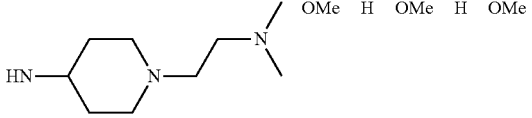 | OMe | H | OMe | H | OMe |
| N | CH | OMe | 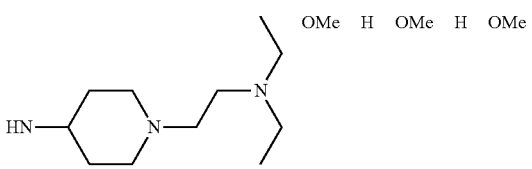 | OMe | H | OMe | H | OMe |
| N | CH | OMe | NO₂ | H | H | F | H | H |
| N | CH | OMe | NH₂ | H | H | CN | H | H |
| N | CH | OMe | NO₂ | OMe | H | H | H | OMe |
| N | CH | OMe | NH₂ | OMe | H | H | H | OMe |
| N | CH | OMe | NHMe | OMe | H | H | H | OMe |
| N | CH | OMe | NHCOMe | OMe | H | H | H | OMe |
| N | CH | OMe | NHEt | OMe | H | H | H | OMe |
| N | CH | OMe | NMe₂ | OMe | H | H | H | OMe |
| N | CH | OMe | NEt₂ | OMe | H | H | H | OMe |
| N | CH | OMe | NMeCOMe | OMe | H | H | H | OMe |
| N | CH | OMe | NEtCOMe | OMe | H | H | H | OMe |
| N | CH | OMe | NHCH₂COEt | OMe | H | H | H | OMe |
| N | CH | OMe | NHCH₂CO₂Et | OMe | H | H | H | OMe |
| N | CH | OMe | NHCH₂COMe | OMe | H | H | H | OMe |
| N | CH | OMe | NHCH₂CO₂Me | OMe | H | H | H | OMe |
| N | CH | OMe | NHCH₂CO₂H | OMe | H | H | H | OMe |
| N | CH | OMe | NHCH₂CONH₂ | OMe | H | H | H | OMe |
| N | CH | OMe | NHSO₂Me | OMe | H | H | H | OMe |
| N | CH | OMe | NHSO₂CF₃ | OMe | H | H | H | OMe |
| N | CH | OMe | NHCH₂CH₂NEt₂ | OMe | H | H | H | OMe |
| N | CH | OMe | 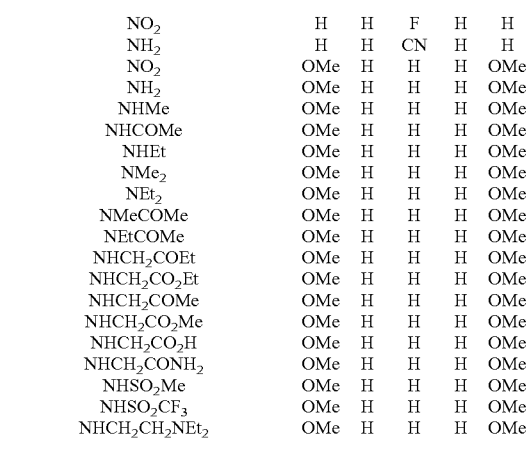 | OMe | H | H | H | OMe |
| N | CH | OMe | 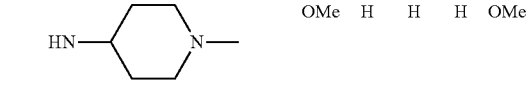 | OMe | H | H | H | OMe |
| N | CH | OMe | 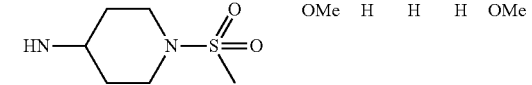 | OMe | H | H | H | OMe |
| N | CH | OMe | 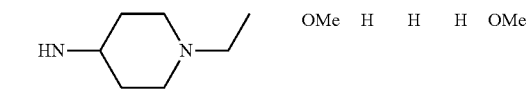 | OMe | H | H | H | OMe |
| N | CH | OMe | 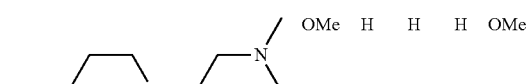 | OMe | H | H | H | OMe |
| CH | N | OMe | NO₂ | OMe | H | OMe | H | OMe |
| CH | N | OMe | NH₂ | OMe | H | OMe | H | OMe |
| CH | N | OMe | NHMe | OMe | H | OMe | H | OMe |
| CH | N | OMe | NHCOMe | OMe | H | OMe | H | OMe |
| CH | N | OMe | NHEt | OMe | H | OMe | H | OMe |
| CH | N | OMe | NMe₂ | OMe | H | OMe | H | OMe |
| CH | N | OMe | NEt₂ | OMe | H | OMe | H | OMe |

-continued

| X¹ | X³ | R₁ | R₂ | R₃ | R₄ | R₅ | R₆ | R₇ |
|---|---|---|---|---|---|---|---|---|
| CH | N | OMe | NMeCOMe | OMe | H | OMe | H | OMe |
| CH | N | OMe | NEtCOMe | OMe | H | OMe | H | OMe |
| CH | N | OMe | NHCH₂COEt | OMe | H | OMe | H | OMe |
| CH | N | OMe | NHCH₂CO₂Et | OMe | H | OMe | H | OMe |
| CH | N | OMe | NHCH₂COMe | OMe | H | OMe | H | OMe |
| CH | N | OMe | NHCH₂CO₂Me | OMe | H | OMe | H | OMe |
| CH | N | OMe | NHCH₂CO₂H | OMe | H | OMe | H | OMe |
| CH | N | OMe | NHCH₂CONH₂ | OMe | H | OMe | H | OMe |
| CH | N | OMe | NHSO₂Me | OMe | H | OMe | H | OMe |
| CH | N | OMe | NHSO₂CF₃ | OMe | H | OMe | H | OMe |
| CH | N | OMe | NHCH₂CH₂NEt₂ | OMe | H | OMe | H | OMe |
| CH | N | OMe | HN-(4-piperidinyl)-N-Me | OMe | H | OMe | H | OMe |
| CH | N | OMe | HN-(4-piperidinyl)-N-SO₂Me | OMe | H | OMe | H | OMe |
| CH | N | OMe | piperidin-1-yl | OMe | H | OMe | H | OMe |
| CH | N | OMe | HN-(4-piperidinyl)-N-CH₂CH₂NMe₂ | OMe | H | OMe | H | OMe |
| CH | N | OMe | HN-(4-piperidinyl)-N-CH₂CH₂NEt₂ | OMe | H | OMe | H | OMe |
| CH | N | OMe | NO₂ | OMe | H | H | H | OMe |
| CH | N | OMe | NH₂ | OMe | H | H | H | OMe |
| CH | N | OMe | NHMe | OMe | H | H | H | OMe |
| CH | N | OMe | NHCOMe | OMe | H | OMe | H | OMe |
| CH | N | OMe | NHEt | OMe | H | H | H | OMe |
| CH | N | OMe | NMe₂ | OMe | H | H | H | OMe |
| CH | N | OMe | NEt₂ | OMe | H | H | H | OMe |
| CH | N | OMe | NMeCOMe | OMe | H | H | H | OMe |
| CH | N | OMe | NEtCOMe | OMe | H | H | H | OMe |
| CH | N | OMe | NHCH₂COEt | OMe | H | H | H | OMe |
| CH | N | OMe | NHCH₂CO₂Et | OMe | H | H | H | OMe |
| CH | N | OMe | NHCH₂COMe | OMe | H | H | H | OMe |
| CH | N | OMe | NHCH₂CO₂Me | OMe | H | H | H | OMe |
| CH | N | OMe | NHCH₂CO₂H | OMe | H | H | H | OMe |
| CH | N | OMe | NHCH₂NH₂ | OMe | H | H | H | OMe |
| CH | N | OMe | NHSO₂Me | OMe | H | H | H | OMe |
| OMe | N | OMe | NHSO₂CF₃ | OMe | H | H | H | OMe |
| CH | N | OMe | NHCH₂CH₂NEt₂ | OMe | H | H | H | OMe |
| CH | N | OMe | HN-(4-piperidinyl)-N-Me | OMe | H | H | H | OMe |
| CH | N | OMe | HN-(4-piperidinyl)-N-SO₂Me | OMe | H | H | H | OMe |
| CH | N | OMe | HN-(4-piperidinyl)-N-Et | OMe | H | H | H | OMe |

-continued

| X¹ | X³ | R₁ | R₂ | R₃ | R₄ | R₅ | R₆ | R₇ |
|---|---|---|---|---|---|---|---|---|
| CH | N | OMe | (HN-piperidine-N-CH₂CH₂-N(Me)-) | OMe | H | H | H | OMe |
| CH | N | OMe | (HN-piperidine-N-CH₂CH₂-N(Et)₂) | OMe | H | H | H | OMe |
| CH | N | OMe | NO₂ | H | H | F | H | H |
| CH | N | OMe | NH₂ | H | H | CN | H | H |

In one preferred embodiment the compound of the invention is of formula I'a or a pharmaceutically acceptable salt or solvate or physiologically hydrolysable, solubilising or immobilisable derivative thereof (e.g. a pharmaceutically acceptable salt or ester thereof), wherein:

| X¹ | X³ | R₁ | R₂ | R₃ | R₄ | R₅ | R₆ | R₇ |
|---|---|---|---|---|---|---|---|---|
| N | CH | OMe | NHSO₂Me | OMe | H | OMe | H | OMe |
| CH | N | OMe | NHSO₂Me | OMe | H | OMe | H | OMe |
| N | CH | OMe | NH₂ | OMe | H | OMe | H | OMe |
| CH | N | OMe | NH₂ | OMe | H | OMe | H | OMe |
| N | CH | OMe | NHCH₂CO₂Et | OMe | H | OMe | H | OMe |
| CH | N | OMe | NHCH₂CO₂Et | OMe | H | OMe | H | OMe |
| N | CH | OMe | NO₂ | OMe | H | H | H | OMe |
| CH | N | OMe | NO₂ | OMe | H | H | H | OMe |
| N | CH | OMe | piperidin-1-yl | OMe | H | OMe | H | OMe |
| CH | N | OMe | piperidin-1-yl | OMe | H | OMe | H | OMe |

In one most preferred embodiment the compound of the invention is of formula I'a or a pharmaceutically acceptable salt or solvate or physiologically hydrolysable, solubilising or immobilisable derivative thereof (e.g. a pharmaceutically acceptable salt or ester thereof), wherein:

| X¹ | X³ | R₁ | R₂ | R₃ | R₄ | R₅ | R₆ | R₇ |
|---|---|---|---|---|---|---|---|---|
| N | CH | OMe | NHSO₂Me | OMe | H | OMe | H | OMe |
| CH | N | OMe | NHSO₂Me | OMe | H | OMe | H | OMe |

In a further aspect of the invention there is provided a compound of formula I as hereinbefore defined wherein one or more R⁸ or R⁹ alternatively or additionally comprise devices for immobilisation thereof. Such devices may be chemical functions that can be used for covalent attachment to solid phases such as functionalised polymers (e.g. agarose, polyacrylamide, polystyrene etc.) as commonly found in matrices (microtitre plate wells, microbeads, membranes, etc.) used for biochemical assays and affinity chromatography. Alternatively, the devices may be small molecules (e.g. biotin) or polypeptides (e.g. antigens), which can be used for non-covalent immobilisation through binding to an immobilised receptor (e.g. avidin or streptavidin in the case of biotin, or a specific antibody in the case of antigens).

In a further aspect of the invention there is provided a precursor to a compound of formula I as hereinbefore defined wherein one or more R⁸ or R⁹ is a solubilising moiety comprising a natural or unnatural amino acid residue, peptide or derivative as hereinbefore defined.

In a further aspect of the invention there is provided a process for the preparation of a compound of formula I as hereinbefore defined. Compounds of formula I may be prepared using any methods known in the art. Suitably compounds are prepared using the method of WO03/072062, WO2005/046599, WO2000/57872, WO2002/069892, WO2006/091870, the contents of which are incorporated herein by reference.

Preferably a process for the preparation of compounds of formula I comprises the condensation of aromatic aldehydes X

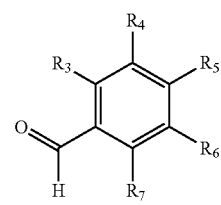

where R³ to R⁷ are as hereinbefore defined, with heteroarylsulfinyl acetic acids IX or heteroarylsulfonyl acetic acids VIII respectively

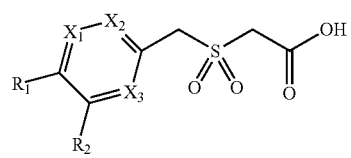

-continued

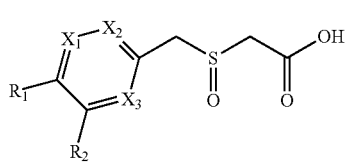

VIII

Preferably condensation is a Knoevenagel condensation.

Hydrolysis of intermediates of formula VII and VIII results in intermediates of formula IX and VIII respectively

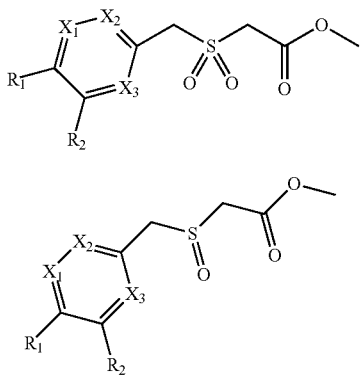

VII

VIII

Oxidation of intermediates V and VI results in intermediates of formula VII and VIII, and formula IX and VIII, respectively

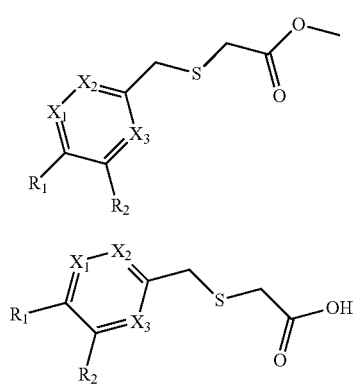

V

VI

Hydrolysis of intermediate of formula V results in intermediate of formula VI.

Reacting heteroaryl intermediates of formula III

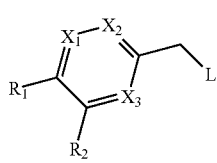

III where the heteroaryl is selected from pyridinyl, pyrimidinyl, pyridazinyl or pyrazinyl, $R^1$ and $R^2$ are hereinbefore defined, and L is any leaving group, preferably halogen group, with a compound of formula IV, gives an intermediate of formula V.

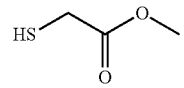

IV

Preferably compounds of the invention are prepared using the method outlined in Scheme 1 shown in FIG. 1 below.

Compounds of formula III, wherein $R^1$, $R^2$, $X^1$, $X^2$ and $X^3$ are as hereinbefore defined, and L is a leaving group, are commercially available or can be prepared using conventional knowledge in the art. Typically, reaction of a compound of formula XI

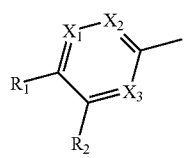

XI wherein $R^1$, $R^2$, $X^1$, $X^2$ and $X^3$ are as hereinbefore defined, is with halosuccinimides in the presence of benzoyl peroxide. Suitable solvents include carbon tetrachloride and chloroform. Examples of compounds of formula XI include 2-alkoxy-5-methyl-3-nitropyridines, 5-alkoxy-2-methyl-4-nitropyridines, 3-alkoxy-6-methyl-2-nitropyridines, 2-alkoxy-5-methyl-3-nitropyrazines, 3-alkoxy-6-methyl-4-nitropyridazines and 5-alkoxy-2-methyl-4-nitropyrimidines.

The oxidation of sulphides of formula V or VI to sulfones of formula VII or IX or sulfoxides of formula VIII or VIII, can be achieved by a wide range of methods known in the art. Examples of suitable oxidant reagents include but are not limited to aqueous hydrogen peroxide, peracetic acid, mCPBA, sodium metaperiodate, nitrogen tetraoxide, and halogens and their derivatives, preferably aqueous 30% hydrogen peroxide because it is inexpensive, environmentally benign, easy to handle, safely stored and produces only water as a by-product. Using transition metal (Ti, Mo, Fe, V, W, Re, Cu and Au) compounds as catalysts with aqueous hydrogen peroxide may efficiently provide the desired sulfoxides of formula VIII or VIII. Further oxidation of sulfoxides of formula VIII or VIII to the corresponding sulfones of formula VII and IX respectively may be conveniently achieved by adjustment of the reaction conditions which include temperature, reaction time, and the relative amounts of oxidant and catalyst.

Condensation reaction between the sulfonyl acetic acids of formula IX or sulfinyl acetic acids of formula VIII and substituted benzaldehydes of formula X may facilitate the formation of compounds of formula I' or I'' respectively under the Knoevenagel reaction conditions known in the art. The catalyst is most often a secondary amine, preferably piperidine. Pyridine or alkoxides are also common catalysts in the art.

Therapeutic Use

In a further aspect of the invention there is provided the use of one or more compounds of formula I (e.g. of formula Ia, I', I'', I'a or I''a) or salts, solvates or derivatives as hereinbefore defined in the manufacture of a medicament for treating a condition mediated by one or more of an aurora kinase, PLK, CDK, BCR-ABL and one of other tyrosine kinases as hereinbefore defined, preferably such medicament is capable of inhibiting such enzymes. The compounds of the invention may inhibit any of the steps or stages in the cell cycle.

Cell division is the only way for life to expend. However when uncontrolled it becomes the way for development of cancer. In eukaryotic cells, the cell cycle can be described as two distinct phases: interphase and mitosis that precedes cell division. The interphase can be further divided into three phases: S-phase standing for DNA synthesis surrounded by two Gap-phases G1 and G2 phases. Mitosis is the most important part of cell cycle. It engages a complex machine aiming to separate its genetic information and subcellular components into two identical sets that are inherited by the two daughter cells. Errors during mitosis lead to turmourgenesis. The coordination of progression through mitosis is mainly orchestrated by protein phosphorylation of several serine/threonine kinases. The main mitotic kinase families include polo-like kinase (PLK), Auorora kinase, cyclin-dependent kinase (CDK), mitogen-activated kinases (MAPK) or other tyrosine kinases PLKs play essential roles in several stages of mitosis and cytokinesis with a dynamic pattern of localization to centrosomes, kinetochores and central spindle structures during the cell cycle. On entry into mitosis, PLKs activate CDK1-cyclin B through phosphorylation of upstream regulators and cyclin B. At the same time, PLKs also promote centrosome maturation, disassembly of the Golgi complex and dissociation of cohesin from the chromosomes. Subsequently, PLKs help initiate anaphase through regulation of the anaphase-promoting complex (APC) and other proteins. Finally, PLKs promote cytokinesis through roles in formation and positioning of the central spindle and yeast septum.

PLKs contain an N-terminal kinase domain (residues 49-310 in the human Plk1 sequence) with a requirement for phosphorylation of a threonine in the activation segment of the kinase (Thr210 in human PLK1) by an upstream kinase. The C-terminal region (residues 345-603) contains the polo box domain (PBD). The PBD has at least two functions. It is an auto-inhibitory domain; inhibition by the PBD can be relieved by phosphorylation of Thr210 or mutation of Thr210 to aspartate. Secondly, the PBD plays a crucial role in subcellular localization. Both polo boxes are required for localization, and over-expression of the PBD induces defective bipolar spindles.

The preferred substrate epitope for PLK phosphorylation has been identified as Glu/Asp-X-Ser/Thr-, where X is any amino acid and is usually hydrophobic, frequently leucine, from the sites phosphorylated with substrates such as Cdc25C, SCC1, BRAC2, Myt1, cyclin B, NudC and MKIp2. Major progress in understanding this process was achieved recently with a proteomic screen that identified an optimal phospho-peptide motif for binding to the PBD with the sequence Met.Gln.Ser.pThr.Pro.Leu (Elia et al., 2003). The phospho-peptide was able to disrupt PLK substrate binding and localization of the PBD to centrosomes. The function of the polo boxes remains incompletely understood but polo box-dependent PLK1 activity is required for proper metaphase/anaphase transition and cytokinesis.

Four PLKs, PLK1, PLK2, PLK3 and PLK4 have been identified in human. They share extensive homologies across their kinase domains, in C-terminal polo boxes. PLK2 (also known as SNK) and PLK3 (also known as PRK and FNK) were originally shown to be immediate early gene products. PLK3 kinase activity appears to peak during late S and G2 phase. It is also activated during DNA damage checkpoint activation and severe oxidative stress. PLK3 also plays an important role in the regulation of microtubule dynamics and centrosome function in the cell and deregulated PLK3 expression results in cell cycle arrest and apoptosis. PLK2 and PLK4 are the least well understood homologue of the four PLKs.

PLK1 is a key mitotic regulator that modulates the transition through the G21M checkpoint by influencing the activation of the phosphatase CDC25C and cyclin [3]. Using neutralizing antibodies, anti-sense oligos, and dominant negative protein, PLK 1 was shown to be essential for mitosis in in vitro cultured cells. Furthermore, down regulation of PLK1 appears to have differential effects in tumour versus "normal" cells in that ablation of PLK1 induces mitotic catastrophe and eventual cell death but causes arrest in normal cells. One plausible explanation is that tumour cells are defective in checkpoint controls and unable to arrest and thus undergo mitotic catastrophe. PLK1 is overexpressed in nonsmall-cell lung cancer, head and neck squamous cell cancer, prostate cancer, ovarian cancer, and pancreatic cancer. In nonsmall-cell lung cancer, head and neck squamous cell cancer, and ovarian cancer, high PLK1 expression was an independent prognostic factor of shorter survival.

Furthermore current cancer therapies using cytotoxic agents, including taxanes which involve the disruption of microtubule formation and degradation, have become successful ways of treating cancer. Some cancer cells are capable of evading the G2/M cell cycle arrest effect of taxanes. Based on their function PLK1 inhibition should represent a novel approach to combat such cancer cells.

Aurora kinases are localised to components of the mitotic apparatus and that regulate the completion of centrosome maturation, bipolar spindle assembly, chromosome segregation, and cytokinesis. Three human Aurora kinases have been identified which are designated as A, B and C. Aurora A localises to the mitotic spindle poles and is required for recruitment of several centrosomal proteins and for mitotic spindle assembly. Aurora B as a chromosomal passenger protein is involved in cytokinesis and chromosome architecture. It localises at the chromosome centromeres from prophase through to metaphase, and then at anaphase relocalises to the spindle midzone at the site of the cytoplasmic ingression where the daughter cells will ultimately separate. It has functions associated with histone phosphorylation and chromatin condensation in prophase, chromosome alignment and segregation, the regulation of a mitotic checkpoint at metaphase, and finally it also has a role in cytokinesis. Much less is known about the function of Aurora C.

Aurora A kinase has been suggested as a potential marker of tumour progression and prognosis, Overexpression of Aurora A kinase contributes to genetic instability and tumourigenesis by disrupting the proper assembly of the mitotic checkpoint complex. In addition, Aurora A kinase is a key regulatory component of the p53 pathway and its overexpression leads to an increase in p53 degradation, which facilities oncogenic transformation. Aurora A has been identified as a colon cancer-associated kinase that is overexpressed in more than 50% of primary colorectal cancers and amplification or overexpression have been detected in breast and ovarian tumours, as well as in multiple tumour cell lines.

CDKs are associated with various cyclin subunits, playing pivotal roles in the regulation of a variety of important regulatory pathways in cells, including cell-cycle control, apoptosis, neuronal physiology, differentiation and transcription. There are now about twelve CDKs which may be classified into two major groups, reflecting their functions. The cell cycle regulator CDKs composed primarily of CDK1, CDK2, CDK3, CDK4 and CDK6 function with their cyclin partners including cyclin A, B, D1, D2, D3, E, and F to regulate promotion of the cell cycle. The transcription regulator CDKs, which include CDK7, CDK8, CDK9 and CDK11 work together with cyclin C, H, K, L1, L2, T1 and T2, tend to play roles in transcriptional regulation. CDK1 (or CDC2) has long been considered as THE cell cycle master kinase, though to be responsible for all cell cycle transitions. This is true in yeast where CDK1 kinase activity is required for the G1/S and the G2/M transition. In mammalian cell however, CDK1 activity is only required for the G2/M transition. CDK1-cyclin B activity appears in late G2 and peaks at metaphase and is inactivated exit from mitosis by cyclin B destruction, degraded first on the spindle at the chromosome level together with cohesions. CDK1 kinase plays important role in early stages that contribute to the G2/M transition. CDK1 phosphorylates motor proteins involved in centrosome separation required for bipolar spindle assembly. CDK1 phosphorylates lamina inducing a destabilization of the nuclear structure and leading to nuclear envelop breaks down. It also phosphorylates condensing contributing to chromosome condensation. While CDK1 activity is maximum, it participates to the activation of the APC/C that insure the ubiquitination of the proteins targeted to be degraded at the metaphase/anaphase transition, including cyclin B and securin.

The CDKs have been implicated in cell proliferation disorders, particularly in cancer. Cell proliferation is a result of the direct or indirect deregulation of the cell division cycle and the CDKs play a critical role in the regulation of the various phases of this cycle. Therefore, inhibitors of CDKs and their associated cyclins are useful targets for cancer therapy.

Mitogen-activated protein kinase (MAPK) pathway is a signal transduction pathway that couples intracellular responses to the binding of growth factors to cell surface receptors. In mammalian cells extracellular signal-regulated kinases (ERKs) are the best studies members of the MAPK family. The MAPK pathway involves extracellular signal-regulated kinases which constitute the Ras/Raf/MEK/ERK kinase cascade. In many cell types, activation of this pathway promotes cell division and oncogenic transformation.

AKT/PKB is a serine/threonine protein kinase that plays a key role in multiple cellular processes such as glucose metabolism, cell proliferation, apoptosis, transcription and cell migration. AKT1 is involved in cellular survival pathways, by inhibiting apoptotic processes. AKT is known to play a role in the cell cycle. Under various circumstances, activation of AKT was shown to overcome cell cycle arrest in G1 and G2 phases. Moreover, activated AKT may enable proliferation and survival of cells that have sustained a potentially mutagenic impact and, therefore, may contribute to acquisition of mutations in other genes. AKT1 is also able to induce protein synthesis pathways, and is therefore a key signaling protein in the cellular pathways that lead to skeletal muscle hypertrophy, and general tissue growth. Since it can block apoptosis, and thereby promote cell survival, AKT1 has been implicated as a major factor in many types of cancer.

PI3Ks are a family of enzymes and have been linked to an extraordinarily diverse group of cellular functions, including cell growth, proliferation, differentiation, motility, survival and intracellular trafficking. involved in cellular functions such as cell growth, proliferation, differentiation, motility, survival and intracellular trafficking, which in turn are involved in cancer. PI3K family is divided into three different classes: Class I, II, and III. The majority of the research on PI3K has focused on the Class I PI3K. Class I PI3K are composed of a catalytic subunit known as p110 and a regulatory subunit related to either p85 or p101. PI3K p110α is mutated in many cancers. Hence, PI3K activity contributes significantly to cellular transformation and the development of cancer. Many of the functions relate to the ability of class I PI3K to activate protein kinase B (PKB, AKA, AKT) as in the PI3K/AKT/mTOR pathway. PI3Ks are also a key component of the insulin signalling pathway. Hence there is great interest in the role of Mks signalling in diabetes mellitus.

In one embodiment such medicament is suitable for inhibition of a proliferative disorder mediated by a AKT, aurora kinase, CDK, BCR-ABL PLK, PI3K and one of other protein kinases. Preferably it is useful in the treatment of a proliferative disorder, such as cancers, leukaemias and other disorders associated with uncontrolled cellular proliferation such as psoriasis and restenosis, a viral disorder, a cardiovascular disease, a CNS disorder, an autoimmune disease, a bond disease, a hormone-related disease, a metabolic disorder, stroke, alopecia, an inflammatory disease or an infectious disease.

Preferably the compound of formula I (e.g. the compound of formula Ia, I', I", I'a, or I"a) is capable of inhibiting one or more of the host cell kinases involved in cell proliferation, viral replication, a cardiovascular disorder, neurodegeneration, autoimmunity, a metabolic disorder, stroke, alopecia, an inflammatory disease or an infectious disease.

A proliferative disorder requires treatment of a susceptible neoplasm and may be selected from the group consisting of chronic lymphocytic leukaemia, lymphoma, leukaemia, breast cancer, lung cancer, prostate cancer, colon cancer, melanoma, pancreatic cancer, ovarian cancer, squamous carcinoma, carcinoma of head and neck, endometrial cancer, and aesophageal carcinoma.

Preferably, the proliferative disorder is a cancer or leukaemia. The term proliferative disorder is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, antiparasitic disorders such as malaria, emphysema and alopecia. In these disorders, the compounds of the present invention may induce apoptosis or maintain stasis within the desired cells as required.

As defined herein an effect against a proliferative disorder mediated by a kinase within the scope of the present invention may be demonstrated by the ability to inhibit cell proliferation in an in vitro whole cell assay, for example using any of the cell lines including, but not limiting to A549, A2780, HT29, PC3, Du-145, Saos-2, HCT-116, HeLa, MCF-7, NCI-H460 in an appropriate assay. These assays including methods for their performance are described in more detail under Biological Activity.

In a preferred embodiment, the invention relates to a method of treating a PLK-dependent disorder, said method comprising administering to a subject in need thereof, a compound of the invention or a pharmaceutically acceptable salt thereof, as defined above in an amount sufficient to inhibit a PLK.

Preferably the compound of the invention is administered in an amount sufficient to inhibit PLK1, PLK2 and/or PLK3.

In another preferred embodiment, the invention relates to a method of treating an aurora kinase-dependent disorder, said method comprising administering to a subject in need thereof, a compound of the invention or a pharmaceutically acceptable salt thereof, as defined above in an amount sufficient to inhibit an aurora kinase.

Preferably the compound of the invention is administered in an amount sufficient to inhibit aurora kinase A, aurora kinase B or aurora kinase C.

In another preferred embodiment, the compound of the invention is administered in an amount sufficient to inhibit a CDK.

In another preferred embodiment, the compound of the invention is administered in an amount sufficient to inhibit AKT/PKB.

In another preferred embodiment, the compound of the invention is administered in an amount sufficient to inhibit PI3K.

In another preferred embodiment, the invention relates to a method of treating a tyrosine kinase-dependent disorder, said method comprising administering to a subject in need thereof, a compound of the invention or a pharmaceutically acceptable salt thereof, as defined above in an amount sufficient to inhibit a protein kinase.

Preferably the compound of the invention is administered in an amount sufficient to inhibit at least one of BCR-ABL, MAPK, FLT, IKK, JAK, PDGF, PKA, PKB, PKC, VEGF or Src.

In another preferred embodiment, the invention relates to a method of selectively treating a protein kinase-dependent disorder, said method comprising administering to a subject in need thereof, a compound of the invention or a pharmaceutically acceptable salt thereof, as defined above in an amount sufficient to inhibit a selected protein kinase. Preferably said method comprising contacting said protein kinase with a compound of the invention.

Preferably the compound of the invention is administered in an amount sufficient to inhibit at least one of a PLK, aurora kinase, CDK, AKT, PI3K, or another protein kinase including, but not limiting to BCR-ABL, MAPK, FLT, IKK, JAK, PDGF, PKA, PKB, PKC, VEGF or Src.

The use of a compound of the invention in the manufacture of a medicament as hereinbefore defined includes the use of the compound directly, or in any stage of the manufacture of such a medicament, or in vitro in a screening programme to identify further agents for the prevention or treatment of the hereinbefore defined diseases or conditions.

A further aspect of the invention relates to the use of a compound of formula I (e.g. of formula Ia, I', I", I'a or I"a) or a pharmaceutically acceptable salt or solvate or physiologically hydrolysable, solubilising or immobilising derivative thereof, in an assay for identifying candidate compounds capable of treating one or more disorders or diseases as hereinbefore defined. Preferably a compound is of use in identifying candidate compounds capable of inhibiting a protein kinase, more preferably one or more of a PLK, aurora kinase, CDK, AKT, PI3K or a tyrosine kinase including, but not limiting to BCR-ABL, MAPK, FLT, IKK, JAK, PDGF, PKA, PKB, PKC, VEGF or Src.

Pharmaceutical Compositions

In a further aspect of the invention there is provided a pharmaceutical composition comprising a therapeutically effective amount of a compound of formula I (e.g. of formula Ia, I', I", I'a or I"a) or its physiologically acceptable salt and physiologically hydrolysable derivative as hereinbefore defined in association with one or more pharmaceutical carriers, excipients or diluents. Suitable carriers, excipients or diluents may be selected having regard to the intended mode of administration and standard practice.

The pharmaceutical compositions may be for human or animal usage in human and veterinary medicine, preferably for treatment of a condition, disease or disorder as hereinbefore defined or in inhibiting one or more protein kinase enzyme, more preferably one or more of a PLK, aurora kinase, CDK, AKT, PI3K, or a tyrosine kinase including, but not limiting to BCR-ABL, MAPK, FLT, IKK, JAK, PDGF, PKA, PKB, PKC, VEGF or Src.

Examples of suitable carriers include lactose, starch, glucose, methyl cellulose, magnesium stearate, mannitol, sorbitol and the like.

A therapeutically effective amount is any amount from 0.1% to 99.9% w/w, e.g. from 0.1 to 50% w/w or from 50 to 99.9% w/w, such as from 1 to 95% w/w or from 5 to 90% w/w or from 10 to 80% w/w.

A composition of the invention is suitably for any desired mode of administration including oral, rectal, vaginal, parenteral, intramuscular, intraperitoneal, intraarterial, intrathecal, intrabronchial, subcutaneous, intradermal, intravenous, nasal, buccal or sublingual and the like.

A composition for oral administration is suitably formulated as a compressed tablet, tablet, capsule, gel capsule, powder, solution, dispersion, suspension, drops or the like. Such forms may be produced according to known methods and may include any suitable binder, lubricant, suspending agent, coating agent or solubilising agent or combinations thereof.

A composition for administration by means of injection is suitably formulated as a sterile solution or emulsion from a suitable solution or powder. Alternatively a composition may be in the form of suppositories, pessaries, suspensions, emulsions, lotions, creams, ointments, skin patches, gels, solgels, sprays, solutions or dusting powders.

An indicated daily dosage is from about 1 mg to about 1000 mg (e.g. from 2 mg to 750 mg or from 3 mg to 650 mg or from 5 mg to 500 mg). Compositions provided in dose form generally contain from about 0.25 mg to about 250 mg (e.g. from 0.5 mg to 200 mg or from 0.75 mg to 150 mg or from 1 mg to 100 mg) of the active ingredient per dose.

A composition may include one or more additional active ingredients or may be administered together with compositions comprising other active ingredients for the treatment of the same or different condition. Coadministration may be simultaneously, consecutively or sequentially.

Any additional active ingredient is suitably selected from other existing anticancer agents. This may be desirable to prevent an overlap of major toxicities, mechanism of action and resistance mechanisms and to enable administration of drugs at their maximum tolerated doses with minimum time intervals between doses. Coadministration is also favoured to promote additive or possible synergistic effects. Selection of other active ingredients and regime of administration may be having regard to a knowledge of agents which are effective in treatment of cell lines derived from the cancer to be treated.

Suitable anti-proliferative agents that may be used in combination with a compound of the invention include DNA damaging agents, anti-metabolites, anti-tumour antibiotics, dihydrofolate reductase inhibitors, pyrimidine analogues, purine analogues, cyclin-dependant kinase inhibitors, thymidylate synthase inhibitors, DNA intercalators, DNA cleavers, topoisomerase inhibitors, anthracyclines, vinca drugs, mitomycins, bleomycins, cytotoxic nucleosides, pteridine drugs, diynenes, podophyllotoxins, platinum containing drugs, differentiation inducers and taxanes. Suitable examples of these drugs are known in the art.

A compound as hereinbefore defined may be in free form, i.e. normally as a base, or in any suitable salt or ester form. Free forms of the compound may be converted into salt or ester form and vice versa, in conventional manner.

Suitable salts include hydrochloride, dihydrochloride, hydroformate, amide, succinate, half succinate, maleate, acetate, trifluoroacetate, fumarate, phthalate, tetraphthalate, benzoate, sulfonate, sulphate, phosphate, oxalate, malonate, hydrogen malonate, ascorbate, glycolate, lactate, malate, tartarate, citrate, aspartate or glutamate and variants thereof. Suitable acids for acid addition salt formation include the corresponding acids, i.e. hydrochloric, formic, amino acid, succinic, maleic, acetic, trifluoroacetic, fumaric, phthalic, tetraphthalic, benzoic, sulfonic, sulphuric, phosphoric, oxalic, malonic, ascorbic, glycolic, lactic, malic, tartaric, citric, aspartic or glutamic acids and the like.

Suitable esters include those obtained with the above acids, with hydroxides such as sodium, potassium, calcium or the like, or with alcohols.

In one preferred embodiment, the compound is provided in the form of a pharmaceutically acceptable salt or ester, for example as a sodium salt or ester.

The compounds of formula I (e.g. of formula Ia, I", I'a or I"a) may be present as one or both enantiomeric or tautomeric forms, or stereo or geometric isomeric forms, where relevant. Such forms may be identified and prepared or isolated by methods known in the art. Reference herein to compounds of formula I (e.g. of formula Ia, I', I", I'a or I"a) also encompasses reference to crystalline forms, polymorphs, hydrous and anhydrous forms and pro-drugs thereof.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

EXAMPLES

A. Synthesis of Compounds

General.
$^1$H-NMR and $^{13}$C-NMR spectra were obtained using a Bruker 400 Ultrashield™ spectrometer at 400 MHz and 100 MHz respectively. These were analysed using the Bruker TOPSPIN 2.1 programme. Chemical shifts are reported in parts per million relative to internal tetramethylsilane standard. Coupling constants (J) are quoted to the nearest 0.1 Hz. The following abbreviations are used: s, singlet; d, doublet; t, triplet; q, quartet; qu, quintuplet; m, multiplet and br, broad. High resolution mass spectra were obtained using a Waters 2795 single quadrupole mass spectrometer/micromass LCT platform. TLC (thin-layer chromatography) was performed using alumina plates coated with silica gel G60. Developed plates were air dried and analysed under a UV lamp (254/365 nm). Silica gel (EM Kieselgel 60, 0.040-0.063 mm, Merck) or ISOLUTE pre-packed columns was used for flash chromatography. Melting points (mp) were determined with an Electrothermal melting point apparatus and are uncorrected.

Preparation of Intermediates

A.1. 2-Chloro-5-methyl-3-nitropyridine

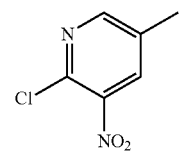

A solution of 5-methyl-3-nitro-1H-pyridone (3.1 g, 20 mmol) in 50 mL chlorobenzene was treated with pyridine (0.47 g, 6.0 mmol) and phosphorus oxychloride (4.7 g, 30.8 mmol). The mixture was refluxed for 1 h. Upon cooling it was treated with sodium carbonate aq. followed by extraction with $CH_2Cl_2$. The organic phase was dried over $Mg_2SO_4$ and filtered. The solvent was evaporated in vacuo to give 2.6 g of the titled compound which was further purified by flash chromatography on silica gel (PE:EtOAc, 8:2, v/v). $^1$H-NMR ($CDCl_3$) δ: 2.45 (s, 3H, $CH_3$), 8.44 (d, 1H, J=2.0 Hz, Py-H), 8.58 (d, 1H, J=2.0 Hz, Py-H); MS (ESI$^+$) m/z 173.0209 [M+H]$^+$, $C_6H_5ClN_2O_2$ requires 172.0040.

A.2. 2-Methoxy-5-methyl-3-nitropyridine

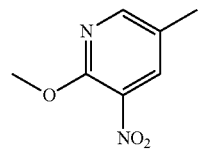

To a solution of sodium (2.31 g, 0.1 mol) dissolved in methanol (100 mL) at room temperature, 2-chloro-5-methyl-3-nitro-pyridine (17.2 g, 0.1 map was added. The reaction mixture was refluxed for 4 h under $N_2$ atmosphere. After evaporated to dryness, the residue was diluted with water (100 mL) and extracted (2×50 mL CH₂Cl₂). The combined extracts were washed with brine, dried on MgSO₄, and filtered. The solvent was evaporated and the residue was crystallized from a mixture of water (300 mL) and ethanol (20 mL) to yield 2-methoxy-5-methyl-3-nitro-pyridine as a light orange solid (15.4 g, 92%). $^1$H-NMR (DMSO-d$_6$): δ 2.31 (s, 3H, CH₃), 3.98 (s, 3H, OCH₃), 8.30 (d, 1H, J=2.0 Hz, Py-H), 8.35 (d, 1H, J=2.0 Hz, Py-H); $^{13}$C-NMR (DMSO-d$_6$): δ 16.80, 54.86, 127.36, 133.7, 135.91, 152.03, 154.27; HR-MS (ESI⁺) m/z 169.0570 [M+H]⁺; C₇H₈N₂O₃ requires 168.0535.

A.3. 5-(Bromomethyl)-2-methoxy-3-nitropyridine

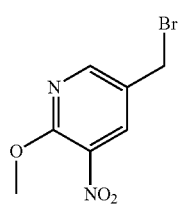

To a well stirred solution of 2-methoxy-5-methyl-3-nitropyridine (8.4 g, 0.05 mol) in carbon tetrachloride (100 mL), benzoyl peroxide (3.5 g, 0.015 mol) and N-bromosuccinimide (17.8 g, 0.1 mol) were added. The reaction mixture was heated at reflux for 48 h under N₂ atmosphere. After cooling, the mixture was evaporated. The residue was diluted with saturated aq. Na₂CO₃ (200 mL) and extracted (3×50 mL CH₂Cl₂). The combined extracts were washed with brine, dried on MgSO₄, and filtered to yield an orange oil-like solid (8.3 g). Purification by chromatography over silica gel eluting with EtOAc/Petroleum ether (0:1 to 1:99 v/v) afforded product as a pale yellow solid. (4.1 g, 43%). $^1$H-NMR (CDCl₃): δ 4.15 (s, 3H, OCH₃), 4.51 (s, 2H, CH₂), 8.34 (d, 1H, J=2.4 Hz, Py-H), 8.43 (d, 1H, J=2.0 Hz, Py-H); $^{13}$C-NMR (CDCl₃): δ 27.72, 55, 17, 127.18, 133.66, 135.67, 151.40, 156.30.

A.4. Methyl 2-((6-methoxy-5-nitropyridin-3-yl)methylthio)acetate

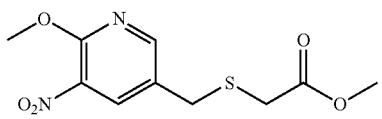

To a solution of 5-bromomethyl-2-methoxy-3-nitropyridine (4.92 g, 0.02 mol) in methanol (50 mL), mercaptomethyl acetate (2.7 mL, 0.03 mol) and sodium carbonate (2.12 g, 0.02 mol) were added at room temperature and stirred for 1 h. After evaporated to dryness, the mixture was dissolved in ethyl acetate (200 mL), filtered and concentrated under reduced pressure. Recrystallisation from EtOH (50 mL) gave the pure product as a pale green solid (3.99 g, 73%). M.p. 57-60° C.; $^1$H-NMR (DMSO-d$_6$): δ 3.32 (s, 2H, CH₂), 3.59 (s, 3H, OCH₃), 3.90 (s, 2H, CH₂), 4.03 (s, 3H, OCH₃), 8.42 (d, 1H, J=2.0 Hz, Py-H), 8.44 (d, 1H, J=2.0 Hz, Py-H); $^{13}$C-NMR (DMSO-d$_6$): δ 31.62, 32.60, 52.54, 55, 17, 128.35, 133.77, 136.05, 152.14, 155.16, 170.74; HR-MS (ESI⁺) m/z: 273.0573 [M+H]⁺; C₇H₆N₂O₃ requires 272.0467.

A.5. 2-((6-Methoxy-5-nitropyridin-3-yl)methylthio)acetic acid

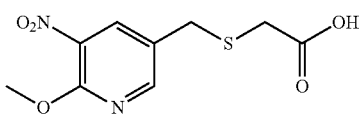 [SMILES: COc1ncc(CSCC(=O)O)cc1[N+](=O)[O-]]

A mixture of methyl 2-((6-methoxy-5-nitropyridin-3-yl)methylthio)acetate (1.0 mmol, 0.27 g) and sodium carbonate (0.3 g) in 150 mL of distilled water was heated at 75° C. for 6 hrs. The mixture was evaporated in vacuo to give 2-((6-methoxy-5-nitropyridin-3-yl)methylthio)acetic acid. Yield 90%; m.p. 249-251° C. (dec.) $^1$H-NMR (D₂O) δ: 3.04 (s, 2H, CH₂), 3.74 (s, 2H, CH₂), 4.01 (s, 3H, OCH₃), 8.28 (d, J=1.0 Hz, 1H, Ar—H), 8.43 (d, J=1.0 Hz, 1H, Ar—H); $^{13}$C-NMR (D₂O) δ: 31.50, 35.93, 55.02, 128.19, 133.18, 136.76, 151.83, 155.53, 177.29; DEPT-135 (O₂O): δ 31.50 (CH₂), 35.93 (CH₂), 55.02 (CH₃) 136.76 (CH), 151.83 (CH); HR-MS (ESI⁺) m/z 257.0206 [M+H]⁺, C₉H₁₀N₂O₆S requires 258.0310.

A.6. Methyl 2-((6-methoxy-5-nitropyridin-3-yl)methylsulfonyl)acetate

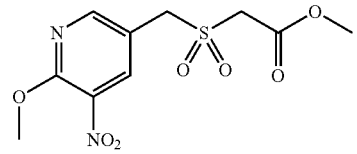 [SMILES: COC(=O)CS(=O)(=O)Cc1cnc(OC)c([N+](=O)[O-])c1]

A solution of methyl 2-((6-methoxy-5-nitropyridin-3-yl)methylthio)acetate (1.64 g, 6 mmol) and hydrogen peroxide 30% (2.6 mL, 0.04 mol) in acetic acid (40 mL) was stirred at 60° C. for 6 hours. The mixture was evaporated to dryness and precipitated by adding ethanol (50 mL) to yield a pale green solid (1.8 g, 98.6%). M.p. 137-140° C.; $^1$H-NMR (DMSO-d$_6$): δ 3.73 (s, 3H, OCH₃), 4.07 (s, 3H, OCH₃), 4.47 (s, 2H, CH₂), 4.80 (s, 2H, CH₂), 8.48 (s, 1H, Py-H), 8.51 (s, 1H, Py-H); $^{13}$C-NMR (DMSO-d$_6$): δ 53.37, 55.23, 55.44, 56.69, 118.25, 133.66, 137.97, 154.27, 156.27, 163.91; HR-MS (ESI⁺) m/z: 305.0519 [M+H]; C₁₀H₆N₂O₉S requires 304.0365.

A.7. 2-((6-Methoxy-5-nitropyridin-3-yl)methylsulfonyl)acetic acid

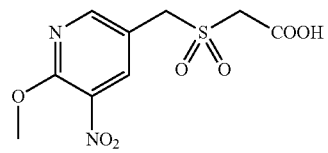 [SMILES: COc1ncc(CS(=O)(=O)CC(=O)O)cc1[N+](=O)[O-]]

A solution of 2-((6-methoxy-5-nitropyridin-3-yl)methylsulfonyl)acetate (1.83 g, 6 mmol) and sodium carbonate (1.8 g, 15 mmol) in a mixture of water (10 mL) and methanol (10 mL) was stirred at room temperature for 4 hours. After evaporated to dryness, the residue was acidized by dropwise addition of 1N aq. HCl. White solid was precipitated gradually as pH was brought to 2 and filtrated to give the pure product (1.72 g, 98.7%). M.p. 183-186° C.; $^1$H-NMR (DMSO-d$_6$): δ 4.06 (s, 3H, OCH$_3$), 4.13 (s, 2H, CH$_2$), 4.79 (s, 2H, CH$_2$), 8.48 (d, 1H J=2.0 Hz, Py-H), 8.50 (d, 1H, J=2.0 Hz, Py-H); $^{13}$C-NMR (DMSO-d$_6$): δ 55.07, 55.41, 57.15, 118.45, 133.64, 137.96, 154.26, 156.23, 164.88; HR-MS (ESI$^+$) m/z: 289.0064 [M+H]$^+$; C$_9$H$_{10}$N$_2$O$_7$S requires 290.0209

A.8. 2-((6-Methoxy-5-nitropyridin-3-yl)methylsulfinyl)acetic acid

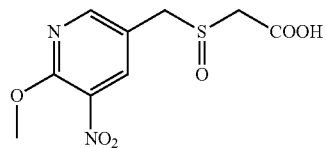 [SMILES: COc1ncc(CS(=O)CC(=O)O)cc1[N+](=O)[O-]]

Treatment of 2-((6-methoxy-5-nitropyridin-3-yl)methylthio)acetic acid (1.0 mmol, 0.26 g) in acetic acid (30 mL) with hydrogen peroxide 35% (1.0 mmol, 0.05 mL) and the mixture was stirred at room temperature for 1.5 hr followed by 60° C. for 30 minutes. The mixture was evaporated in vacuo to yield the title compound. $^1$H-NMR (D$_2$O) δ: 1.97 (s, 2H, CH$_2$), 4.23 (d, 1H, J=14.0 Hz, CH), 4.44 (d, 1H, J=14.0 Hz, CH), 4.14 (s, 3H, OCH$_3$), 8.43 (s, 1H, Py-H), 8.52 (s, 1H, Py-H); HR-MS (ESL) m/z: 273.0146 [M–H]$^-$, C$_9$H$_{10}$N$_2$O$_6$S requires 274.0260.

Production of Compounds According to Formula I

A.9. (E)-2-methoxy-3-nitro-5-((2,4,6-trimethoxystyrylsulfonyl)methyl)pyridine

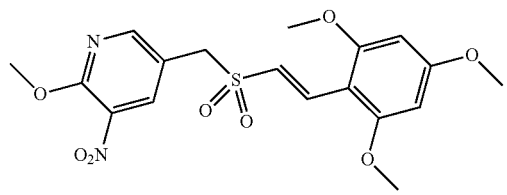

A solution of 2-((5-methoxy-6-nitropyridin-2-yl)methylsulfonyl)acetic acid (2.03 g, 7 mmol) and 2,4,6-trimethoxybenz-aldehyde (1.37 g, 7 mmol) in dry pyridine (20 mL) and piperidine (1 mL) was refluxed for 3 hours under N$_2$ atmosphere. After cooling, the mixture was evaporated, the residue was acidized by addition of 2M aq. HCl and extracted (2×50 mL CH$_2$Cl$_2$). The combined extracts were washed with sat. Na$_2$CO$_3$, brine, dried on MgSO$_4$, and filtered. The residue was further purified by silica gel chromatography, eluting with PE/CH$_2$Cl$_2$/EtOAc (8:2:1 v/v/v) to afford pure product as a white solid (297 mg, 10%). M.p. 183-186° C.; $^1$H-NMR (CDCl$_3$): δ 3.87 (s, 6H, 2×OCH$_3$), 3.88 (s, 3H, OCH$_3$), 4.12 (s, 3H, OCH$_3$), 4.26 (s, 2H, CH$_2$), 6.11 (s, 2H, Ph-H), 7.064 (d, 1H, J=15.6 Hz, CH), 7.80 (d, 1H, J=15.6 Hz, CH), 8.337 (d, 1H, J=2.4 Hz, Py-H), 8.40 (d, 1H, J=2.0 Hz, Py-H); $^{13}$C-NMR (DMSO-d$_6$): δ 55.33, 56.06, 56.46, 91.19, 91.37, 102.77, 120.02, 122.66, 133.34, 135.30, 137.04, 154.14, 155.96, 161.49, 164.46; HR-MS (ESI$^+$) m/z 425.1146 [M+H]$^+$ C$_{18}$H$_{20}$N$_2$O$_8$S requires 424.0940.

A.10. (E)-2-methoxy-5-((2,4,6-trimethoxystyrylsulfonyl)methyl)pyridin-3-amine

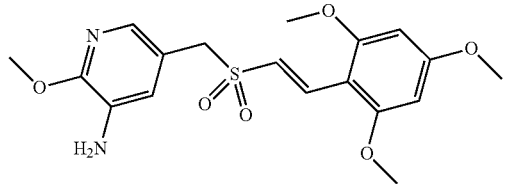

Under N$_2$ atmosphere, a solution of (E)-3-methoxy-2-nitro-6-((2,4,6-trimethoxystyrylsulfonyl)methyl)-pyridine (0.11 g, 0.25 mmol) and Iron powder (0.56 g, 1 mmol) in a mixture of methanol (10 mL) and acetic acid (5 mL) was stirred at 50° C. for 2 hours. After evaporated to dryness, the residue was basified by addition of ammonia (14% aq.) and extracted with EtOAc (5×20 mL). The combined extracts was washed with brine, dried on MgSO$_4$ and filtered. After evaporated to dryness the mixture was purified by silica gel chromatography eluting with PE/EtOAc (2:1 v/v) to yield (E)-2-methoxy-5-((2,4,6-trimethoxystyrylsulfonyl)methyl) pyridin-3-amine as a white solid (89 mg, 90%). $^1$H-NMR (CDCl$_3$): δ 3.85 (s, 6H, 2×OCH$_3$), 3.87 (s, 3H, OCH$_3$), 3.99 (s, 3H, OCH$_3$), 4.13 (s, 2H, CH$_2$), 6.10 (s, 2H, Ph-H), 7.04 (d, 1H, J=2.0 Hz, Py-H), 7.05 (d, 1H, J=15.6 Hz, CH), 7.48 (d, 1H, J=2.0 Hz, Py-H), 7.842 (d, 1H, J=15.6 Hz, CH); HR-MS (ESI$^+$) m/z: 395.1250 [M+H]$^+$; C$_{18}$H$_{22}$N$_2$O$_6$S requires 394.1199.

A.11, (E)-N-(2-methoxy-5-((2,4,6-trimethoxystyrylsulfonyl)methyl)pyridin-3-yl)acetamide

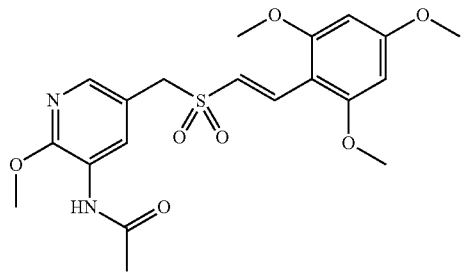 [SMILES: COc1cc(OC)c(/C=C/S(=O)(=O)Cc2cnc(OC)c(NC(C)=O)c2)c(OC)c1]

Acetyl chloride (0.054 mL, 0.76 mmol) was added dropwise into the solution of (E)-2-methoxy-5-((2,4,6-trimethoxystyrylsulfonyl)methyl)pyridin-3-amine (80 mg, 0.21 mmol) in dry pyridine (5 mL) on an ice bath. The mixture was warmed to room temperature and stirred overnight. After evaporated to dryness, the residue was purified by silica gel chromatography, eluting with PE/EtOAc (1:3 v/v) to afford pure product as a white solid (38 mg, 44%). $^1$H-NMR (CDCl$_3$-d$_6$): δ 2.21 (s, 3H, CH$_3$), 3.86 (s, 6H, 2×OCH$_3$), 3.87 (s, 3H, OCH$_3$), 4.03 (s, 3H, OCH$_3$), 4.21 (s, 2H, CH$_2$), 6.11 (s, 2H, Ph-H), 7.13 (d, 1H, J=15.6 Hz, CH), 7.61 (s, 1H, NH), 7.88 (d, 1H, J=15.6 Hz, CH), 7.89 (d, 1H, J=2.0 Hz, Py-H), 8.65 (d, 1H, J=2.0 Hz, Py-H); HR-MS (ESI+) m/z 437.1460 [M+H]+ $C_{20}H_{24}N_2O_7S$ requires 436.1304, A.12. (E)-N-(2-methoxy-5-((2,4,6-trimethoxystyrylsulfonyl)methyl)pyridin-3-yl)methanesulfonamide

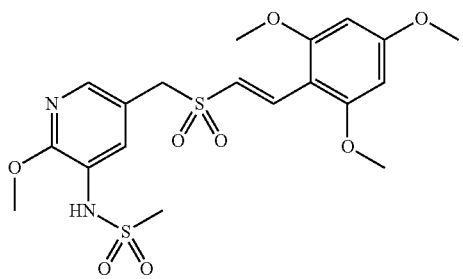 [SMILES: COc1cc(OC)c(/C=C/S(=O)(=O)Cc2cnc(OC)c(NS(C)(=O)=O)c2)c(OC)c1]

Methanesulfonyl chloride (0.048 mL, 0.31 mmol) was added dropwise into the solution of (E)-2-methoxy-5-((2,4,6-trimethoxystyrylsulfonyl)methyl)pyridin-3-amine (111 mg, 0.28 mmol) in dry pyridine (7 mL) on an ice bath. After warming up to room temperature the mixture was stirred overnight. After evaporated to dryness, the residue was purified by silica gel chromatography, eluting with PE/EtOAc (1:2 v/v) to afford pure product as a white solid (42 mg, 32%) $^1$H-NMR (Acetone-$d_6$): δ 2.98 (s, 3H, CH$_3$), 3.90 (s, 3H, OCH$_3$), 3.93 (s, 6H, 2×OCH$_3$), 3.97 (s, 3H, OCH$_3$), 4.38 (s, 2H, CH$_2$), 6.31 (s, 2H, Ph-H), 7.19 (d, 1H, J=15.6 Hz, CH), 7.71 (d, 1H, J=15.6 Hz, CH), 7.85 (d, 1H, J=2.0 Hz, Py-H), 7.97 (d, 1H, J=2.0 Hz, Py-H); $^{13}$C-NMR (Acetone-$d_6$): δ 38.78, 53.30, 55.08, 55.53, 57.36, 90.67, 103.24, 119.44, 121.70, 123.17, 130.21, 134.70, 143.67, 154.11, 161.54, 164.28; HR-MS (ESI+) m/z 473.1115 [M+H]+ $C_{19}H_{24}N_2O_{8}32$ requires 472.0974.

A.13. (E)-ethyl 2-(2-methoxy-5-((2,4,6-trimethoxystyrylsulfonyl)methyl)pyridin-3-ylamino)acetate

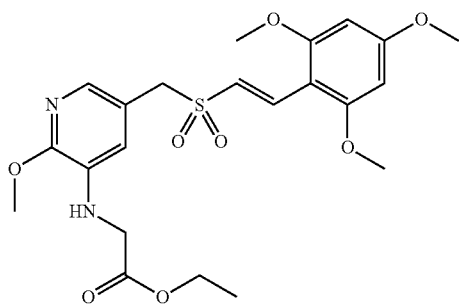 [SMILES: CCOC(=O)CNc1cc(CS(=O)(=O)/C=C/c2c(OC)cc(OC)cc2OC)cnc1OC]

To a solution of (E)-2-methoxy-5-((2,4,6-trimethoxystyrylsulfonyl)methyl)pyridin-3-amine (28 mg, 0.072 mmol) in DMF (5 mL), ethyl bromoacetate (0.110 mL, 1 mmol) and potassium carbonate (138 mg, 1 mmol) were added. The mixture was stirred at 60° C. overnight. The mixture was diluted with H$_2$O (20 mL) and extracted (2×20 mL ethyl acetate). The combined extracts were washed with brine, dried on MgSO$_4$, and filtered. The residue was further purified by silica gel chromatography, eluting with PE/EtOAc (2:3, v/v) to afford pure product as a white solid (24.2 mg, 70%). $^1$H-NMR (CDCl$_3$): δ 3.85 (s, 6H, 2×OCH$_3$), 3.87 (s, 3H, OCH$_3$), 3.90 (d, 2H, J=2.8 Hz, CH$_2$), 4.00 (s, 3H, OCH$_3$), 4.15 (s, 2H, CH$_2$), 4.27 (q, 2H, CH$_2$), 6.10 (s, 2H, Ph-H), 6.74 (d, 1H, J=2.0 Hz, Py-H), 7.04 (d, 1H, J=15.6 Hz, CH), 7.44 (d, 1H, J=2.0 Hz, Py-H), 7.811 (d, 1H, J=15.6 Hz, CH); HR-MS (ESI+) m/z: 481.1364 [M+H]+; $C_{22}H_{28}N_2O_8S$ requires 480.1566, A.14. (E)-2-(2-methoxy-5-((2,4,6-trimethoxystyrylsulfonyl)methyl)pyridin-3-ylamino)acetic acid

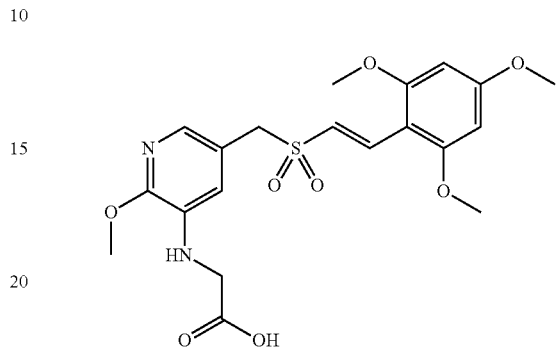

Sodium hydroxide (4 mg, ° Animal) was added to a solution of (E)-ethyl 2-(2-methoxy-5-((2,4,6-trim ethoxystyrylsulfonyl)methyl)pyridin-3-ylamino)acetate (19 mg, 0.04 mmol) in H$_2$O (10 mL). The mixture was stirred at room temperature for 1 h. The residue was acidified by addition of 2M aq HCl and extracted with EtOAc (3×10 mL). The combined extracts was washed with brine, dried on MgSO$_4$, and filtered. The residue was further purified by silica gel chromatography, eluting with PE/EtOAc (2:3, v/v) to afford pure product as a white solid (24.2 mg, 70%). $^1$H-NMR (CDCl$_3$): δ 3.82 (s, 6H, 2×OCH$_3$), 3.83 (s, 3H, OCH$_3$), 3.85 (d, 2H, J=1.6 Hz, CH$_2$), 3.90 (s, 2H, CH$_2$), 3.96 (s, 3H, OCH$_3$), 6.08 (s, 2H, Ph-H), 6.72 (s, 1H, Py-H), 7.02 (d, 1H, J=15.6 Hz, CH), 7.43 (s, 1H, Py-H), 7.78 (d, 1H, J=15.6 Hz, CH); HR-MS (ESI+) m/z: 451.1245 [M−H]−, $C_{20}H_{24}N_2O_8S$ requires 452.1253.

A.15. (E)-N-ethyl-N-(2-methoxy-5-((2,4,6-trimethoxystyrylsulfonyl)methyl)pyridin-3-yl)acetamide

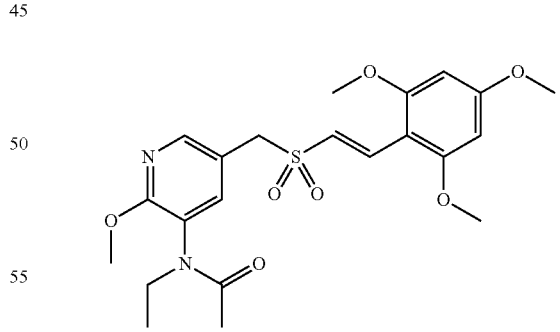

Sodium hydride (0.6 mg, 0.025 mmol) was added into the solution of (E)-N-(2-methoxy-5-((2,4,6-trimethoxystyrylsulfonyl)methyl)pyridin-3-yl)acetamide (10 mg, 0.023 mmol) in dry THF (5 mL). The mixture was stirred at room temperature for 45 min. Iodoethane (15 μL, 0.05 mmol) was added dropwise into the mixture and stirred at room temperature for another 2 h. After evaporated to dryness, the residue was diluted with H$_2$O (10 mL) and extracted (2×20 mL CH$_2$Cl$_2$). The combined extracts were extracted with sat.

Na$_2$CO$_3$, washed with brine, dried on MgSO$_4$, and filtered. The residue was purified by silica gel chromatography, eluting with PE/EtOAc (1:1, v/v) to afford pure product as a white powder (8 mg, 75%). $^1$H-NMR (CDCl$_3$): δ 1.02 (t, 3H, J=7.2 Hz, CH$_3$), 1.74 (s, 3H, CH$_3$), 3.42 (m, 2H, CH$_2$), 3.86 (s, 6H, 2×OCH$_3$), 3.87 (s, 3H, OCH$_3$), 3.99 (s, 3H, OCH$_3$), 4.23 (s, 2H, CH$_2$), 6.10 (s, 2H, Ph-H), 7.07 (d, 1H, J=15.6 Hz, CH), 7.05 (d, 1H, J=2.0 Hz, Py-H), 7.77 (d, 1H, J=15.6 Hz, CH), 8.15 (d, 1H, J=2.0 Hz, Py-H); HR-MS (ESI$^+$) m/z: 465.1762 [M+H]$^+$, C$_{22}$H$_{28}$N$_2$O$_7$S, requires 464.1617.

A.16. (E)-2-(2-methoxy-5-((2,4,6-trimethoxystyrylsulfonyl)methyl)pyridin-3-ylamino)acetic amide

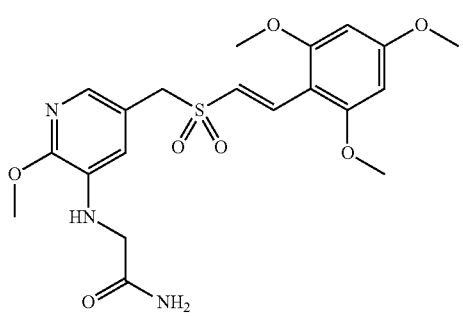 [SMILES: COc1cc(OC)c(/C=C/S(=O)(=O)Cc2cnc(OC)c(NCC(N)=O)c2)c(OC)c1]

(E)-ethyl 2-(2-methoxy-5-((2,4,6-trimethoxystyrylsulfonyl)methyl)pyridin-3-ylamino)acetate (20 mg, 0.04 mmol) was added to a solution of ammonia (5 mL 7N in methanol) and H$_2$O (5 mL). The mixture was stirred at 60° C. for 4 h. After evaporated to dryness, the residue was purified by silica gel chromatography, eluting with PE/EtOAc (1:1, v/v) to afford pure product as a brown powder (9.2 mg, 26%). $^1$H-NMR (CDCl$_3$): δ 3.80 (d, 2H, J=1.6 Hz, CH$_2$), 3.87 (s, 6H, 2×OCH$_3$), 3.87 (s, 3H, OCH$_3$), 4.01 (s, 3H, OCH$_3$), 4.16 (s, 2H, CH$_2$), 5.43 (s, 1H, NH), 6.12 (s, 2H, Ph-H), 6.75 (d, 1H, J=2.0 Hz, Py-H), 7.09 (d, 1H, J=15.6 Hz, CH), 7.56 (d, 1H, J=2.0 Hz, Py-H), 7.81 (d, 1H, J=15.6 Hz, CH); HR-MS (ESI$^+$) m/z 452.1560 [M+H]$^+$ C$_{20}$H$_{25}$N$_3$O$_7$S requires 451.1413.

A.17. (E)-5-((2,6-Dimethoxystyrylsulfonyl)methyl)-2-methoxy-3-nitropyridine

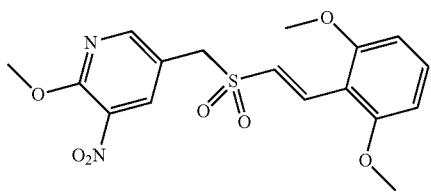 [SMILES: COc1cccc(OC)c1/C=C/S(=O)(=O)Cc1cnc(OC)c([N+](=O)[O-])c1]

A solution of 2-((6-methoxy-5-nitropyridin-3-yl)methylsulfonyl)acetic acid (0.29 g, 1 mmol) in dry pyridine (20 mL) was treated with piperidine (2 mL), followed by 2,6-dimethoxybenzaldehyde (0.17 g, 1 mmol). The mixture was refluxed for 6 h, and evaporated to dryness. The residue was purified by column chromatography using a mixture of EtOAc/PE (1:2, v/v) to yield the titled compound. HR-MS (ESI$^+$) m/z 394.8362; C$_{17}$H$_{18}$N$_2$O$_7$S requires 394.0835.

A.18. (E)-5-((2,6-Dimethoxystyrylsulfonyl)methyl)-2-methoxypyridin-3-amine

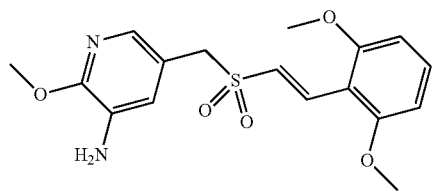

To a solution of (E)-2-methoxy-3-nitro-5-((2,6-trimethoxystyrylsulfonyl)methyl)pyridine (20 mg, 0.04 mmol) in 10 mL of Methanol and acetic acid (3 mL) was added iron powder (0.20 g). The mixture was refluxed for 6 h. Upon cooling the mixture was passes through a pad of celite 521. The filtrate was evaporated to dryness. The residue was purified by flash chromatography; yield 90%; HR-MS (ESI$^+$) m/z 364.8362, C$_{17}$H$_{20}$N$_2$O$_5$S requires 364.1093.

A.19. (E)-2-methoxy-3-nitro-5-((2,4,6-trimethoxystyrylsulfinyl)methyl)pyridine

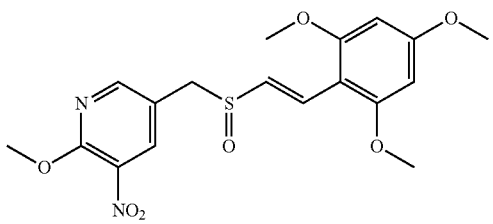

A solution of 2-((6-methoxy-5-nitropyridin-3-yl)methylsulfinyl)acetic acid (0.15 g, 0.5 mmol) in dry pyridine (20 mL) was treated with 2,4,6-trimethoxybenzaldehyde (0.20 g, 1 mmol) and piperidine (10 drops). The mixture was refluxed for 2-3 hrs. The mixture was evaporated and the residue was purified by flash chromatography; yield 10%; $^1$H-NMR (CDCl$_3$): δ 3.83 (s, 6H, OCH$_3$), 3.83 (s, 3H, OCH$_3$), 3.89 (1H, CH), 4.07 (1H, CH), 4.09 (s, 3H, OCH$_3$), 6.09 (s, 2H, Ph-H), 6.97 (d, 1H, J=15.2 Hz, CH), 7.28 (d, 1H, J=15.2 Hz, CH), 8.19 (d, 1H, J=2.3 Hz, Py-H), 8.29 (d, 1H, J=2.3 Hz, Py-H). HR-MS (ESI$^+$) m/z 408.8426 C$_{18}$H$_{20}$N$_2$O$_7$S requires 408.0991.

Preparation of Intermediates

A.20. 3-Methoxy-8-methyl-2-nitropyridine

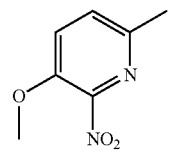

A mixture of 6-methyl-2-nitropyridin-3-ol (15.4 g, 0.1 mol), iodomethane (7.5 mL 0.15 mol), and potassium carbonate (20 g, 0.15 mol) in DMSO (160 mL), were stirred at room temperature for 24 hours. After the reaction was completed, the reaction mixture was added water (3×100 mL) and extracted using ethyl acetate (3×300 mL). The combined organic layer was dried over $Mg_2SO_4$ and filtered. The solvent was evaporated to yield the title product as white powder (15.45 g, 92%). $^1$H-NMR (CDCl$_3$) δ: 2.55 (S, 3H, CH$_3$), 3.96 (S, 3H, OCH$_3$), 7.39 (d, 1H, J=8.8 Hz, Py-H), 7.44 (d, 1H, J=8.8 Hz, Py-H); HR-MS (ESI$^+$) m/z 169.0572 [M+H]$^+$ $C_7H_8N_2O_3$ requires 168.0535.

A.21. 6-(Bromomethyl)-3-methoxy-2-nitropyridine

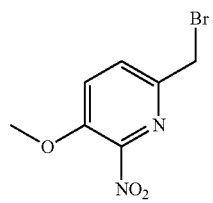

A mixture of 3-methoxy-6-methyl-2-nitropyridine (10.08 g, 60 mmol), NBS (9.79 g, 55 mmol), and benzoyl peroxide (2 g, 6 mmol) in CCl$_4$ (250 mL) was refluxed for 56 hours under nitrogen atmosphere. The reaction mixture was added 100 mL 1M NaOH aq. and extracted using ethyl acetate (3×300 mL). The combined organic layer was dried over Mg$_2$SO$_4$ and filtered. The solvent was evaporated to yield a brown oily. $^1$H-NMR (CDCl$_3$): δ 3.99 (s, 3H, OCH$_3$), 4.51 (s, 2H, CH$_2$), 7.55 (d, 1H, J=8.8 Hz, Py-H), 7.70 (d, 1H, J=8.4 Hz, Py-H). HR-MS (ESI$^+$) m/z 246.9600 [M+1]$^+$ $C_7H_7BrN_2O_3$ requires 245.9640.

A.22. Methyl 2-((5-methoxy-6-nitropyridin-2-yl)methylthio)acetate

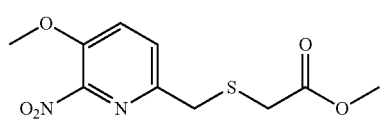

A mixture of 6-(bromomethyl)-3-methoxy-2-nitropyridine (30 mmol, 0.74 g), methythioglycolate (2.7 mL, 30 mmol), and potassium carbonate (5.5 g, 40 mmol) in methanol (200 mL) was stirred at room temperature for 10 hours. After concentrated the mixture was purified by column chromatography using PE/DCM (1:1, v/v) followed by DCM to the titled compound. $^1$H-NMR (CDCl$_3$): δ 3.27 (S, 2H, CH$_2$), 3.74 (S, 3H, OCH$_3$), 3.93 (S, 2H, CH$_2$), 3.99 (S, 3H, OCH$_3$), 7.51 (d, 1H, J=8.6 Hz, Py-H), 7.65 (d, 1H, J=8.6 Hz, Py-H); HR-MS (ESI$^+$) m/z 272.0467 [M+H]$^+$ $C_{10}H_{12}N_2O_5S$ requires 273.0547.

A.23. 2-((5-Methoxy-6-nitropyridin-2-yl)methylthio)acetic acid

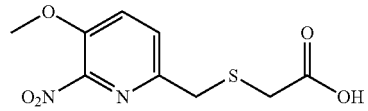

To 150 mL of sodium carbonate 1N solution, methyl 2-((5-methoxy-6-nitropyridin-2-yl)methylthio)acetate (10 mmol, 2.72 g) was added and the mixture was reacted at 50° C. for 16 hrs. The mixture was evaporated in vacuo to give 2-((5-methoxy-6-nitropyridin-2-yl)methylthio)acetic acid. Yield 97%; m.p. 239-230° C. (dec); $^1$H-NMR (D$_2$O) δ: 3.04 (s, 2H, CH$_2$), 3.65 (s, 2H, CH$_2$), 3.78 (s, 3H, OCH$_3$), 7.54 (d, 1H, J=8.4 Hz, Py-H), 8.429 (d, 1H, J=8.4 Hz, Py-H); $^{13}$C-NMR (O$_2$O) δ: 35.79, 36.48, 56.96, 125.75, 130.76, 145.07, 147.96, 148.14, 177.11; DEPT-135 (D$_2$O) δ: 35.79 (CH$_2$), 36.48 (CH$_2$), 56.96 (CH$_3$), 125.75 (CH), 130.76 (CH); HR-MS (ESI$^+$) m/z 257.0101 [M−H]$^-$, $C_9H_{10}N_2O_5S$ requires 258.0310.

A.24. Methyl 2-((5-methoxy-6-nitropyridin-2-yl)methylsulfonyl)acetate

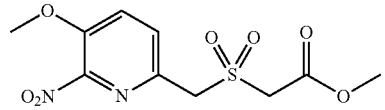

A mixture of methyl 2-((5-methoxy-6-nitropyridin-2-yl)methylthio)acetate (1.6 g, 5.9 mmol) and hydrogen peroxide 35% (2.6 mL, 40 mmol) in acetic acid (50 mL) were stirred at 50° C. for 7 hours. The solvent was evaporated to dryness and was added cold ethanol. The precipitate was filtered to yield the titled compound as white solid (1.17 g, 65%). $^1$H-NMR (CDCl$_3$): δ 3.88 (S, 3H, OCH$_3$), 4.03 (S, 3H, OCH$_3$), 4.16 (S, 2H, CH$_2$), 4.70 (S, 2H, CH$_2$), 7.59 (d, 1H, J=8.6 Hz, Py-H), 7.72 (d, 1H, J=8.5 Hz, Py-H); HR-MS (ESI$^+$) m/z: 305.0479 [M+H]$^+$ $C_{10}H_{12}N_2O_7S$, requires 304.0365.

A.25. Methyl 2-((5-methoxy-6-nitropyridin-2-yl)methylsulfinyl)acetate

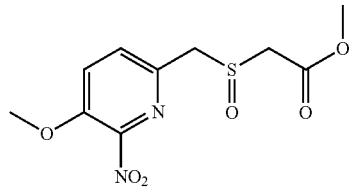

Methyl 2-((5-methoxy-6-nitropyridin-2-yl)methylthio)acetate (1.0 mmol, 0.27 g) and hydrogen peroxide 30% (1.0 mmol, 0.12 mL) were dissolved in acetic acid (10 mL). The mixture stirred at r.t. for 6 hrs and the solvent was evaporated in vacuo. The mixture was purified by column chromatography using 1:1 PE/EtOAc to give the titled compound. Yield 95%; $^1$H-NMR (DMSO-D$_6$) δ: 3.74 (s, 3H, OCH$_3$), 3.76 (d, 1H, J=14.2 Hz), 4.02 (d, 1H, J=14.2 Hz,), 4.07 (s, 3H, OCH$_3$), 4.27 (d, 1H J=12.9 Hz, CH), 4.42 (d, 1H J=12.9 Hz, CH), 7.76 (d, 1H, J=8.6 Hz, Py-H), 7.94 (d, 1H, J=8.6 Hz, Py-H); $^{13}$C-NMR (DMSO-D$_6$) δ: 51.90, 55.1756.52, 57.31, 124.13, 130.82, 141.18, 146.90, 166.11, 205.26. HR-MS (ESI$^+$) m/z 289.0428 [M+H]$^+$ C$_{10}$H$_{12}$N$_2$O$_6$S, requires 288.0416.

A.26. 2-((5-methoxy-6-nitropyridin-2-yl)methylsulfonyl)acetic acid

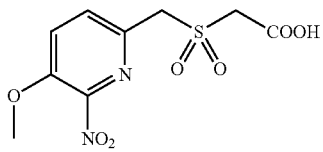

A mixture of methyl 2-((5-methoxy-6-methylpyridin-2-yl)methylsulfonyl)acetate (3.01 g, 10 mmol) and sodium carbonate (1.24 g, 12 mmol) in water (60 mL) and methanol (100 mL) was stirred at room temperature for 10 hours. The reaction mixture was evaporated to dryness. Hydrochloric acid (2N) was added dropwise until pH=2. The mixture was filtered and washed with water to yield the title product as white powder (2.82 g, 97%). $^1$H-NMR (DMSO-D$_6$) δ: 4.00 (s, 3H, OCH$_3$), 4.34 (s, 2H, CH$_2$), 4.84 (s, 2H, CH$_2$), 7.85 (d, 1H, J=8.8 Hz, Py-H), 8.04 (d, 1H, J=8.8 Hz, Py-H); HR-MS (ESI$^+$) m/z 291.0316 [M+1]$^+$, C$_9$H$_{10}$N$_2$O$_7$S requires 290.0209.

A.27. (E)-3-methoxy-2-nitro-6-((2,4,6-trimethoxystyrylsulfonyl)methyl)pyridine

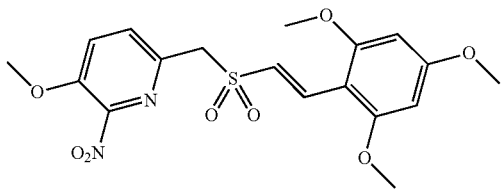

A mixture of 2-((5-methoxy-6-nitropyridin-2-yl)methylsulfonyl)acetic acid (0.29 g, 1.0 mmol) in dry toluene (2 mL) was added 2,4,6-trimethoxybenz-aldehyde (0.196 g, 1.0 mmol) and acetic anhydride (0.38 mL). After refluxing for 5 hrs, the reaction mixture was evaporated to dryness. The residue was precipitated by adding methanol (15 mL). The precipitate was filtered to give 150 mg (35%) the titled compound as grey coloured powder. $^1$H-NMR (Acetone-D$_6$): δ 3.92 (s, 9H, 3×OCH$_3$), 4.07 (s, 3H, OCH$_3$), 4.52 (s, 2H, CH$_2$), 6.32 (s, 2H, Ph-H), 7.20 (d, J=15.6 Hz, 1H, CH), 7.74 (d, 1H, J=15.6 Hz, CH), 7.87 (d, 1H, J=8.4 Hz, Py-H), 7.95 (d, 1H, J=8.8 Hz, Py-H); HR-MS (ESI$^+$) m/z 425.1053 [M+1]$^+$ C$_{18}$H$_{20}$N$_2$O$_8$S requires 424.0940.

A.28. (E)-3-methoxy-6-((2,4,6-trimethoxystyrylsulfonyl)methyl)pyridin-2-amine

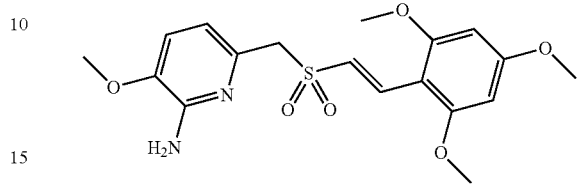

A mixture of 2-((5-methoxy-6-nitropyridin-2-yl)methylsulfonyl)acetic acid (0.88 g, 2 mmol) and iron powder (4.48 g, 8 mmol) in a mixture of methanol (80 mL) and acetic acid (40 mL) was stirred at 501 under nitrogen atmosphere for 3 hours. The reaction mixture was evaporated to dryness. The residue was basified by addition of ammonia (8N, 20 mL) and extracted with EtOAc (5×60 mL). The combined extracts was washed with brine, dried on Mg$_2$SO$_4$ and filtered. After evaporated to dryness the mixture was purified by silica gel chromatography eluting with PE/EtOAc (1:1 v/v) to yield the title compound as a white powder (0.55 g, 69.8%). $^1$H-NMR (DMSO-D$_6$): δ 3.77 (s, 3H, OCH$_3$), 3.86 (s, 9H, 3×OCH$_3$), 4.25 (s, 2H, CH$_2$), 5.736 (s, 2H, Ph-H), 6.30 (s, 2H, NH$_2$), 6.60 (d, 1H, J=8.0 Hz, Py-H), 7.00 (d, 1H, J=7.6 Hz, Py-H), 7.13 (d, 1H, J=15.6 Hz, Py-H), 7.60 (d, 1H, J=16.0 Hz, Py-H). HR-MS (ESI$^+$) m/z 394.1199 [M+H]$^+$ C$_{16}$H$_{22}$N$_2$O$_6$S requires 395.1153.

A.29. (E)-3-Methoxy-2-(piperidin-9-yl)-6-((2,4,6-trimethoxystyrylsulfonyl)methyl)pyridine

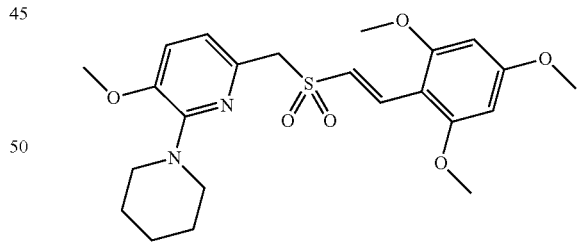

A mixture of 2-((5-methoxy-6-nitropyridin-2-yl)methylsulfonyl)acetic acid (4 mmol, 1.16 g), and 2,4,6-trimethoxybenzalehyde (0.78 g, 4 mmol) in a mixture of pyridine (20 mL) and piperidine (0.3 mL) was refluxed for 5 h. The mixture was extracted with DCM (40 mL). The organic layer was washed with sat. sodium bicarbonate. After concentrated the residue was purified by column chromatography using PE/DCM/EtOAc (8:2:1, v/v/v) to yield 35 mg the titled compound as light yellow powder. $^1$H-NMR (DMSO-d$_6$): 1.43 (m, 6H, 3×CH$_2$), 3.11 (m, 4H, 2×CH$_2$), 3.81 (s, 3H, OCH$_3$), 3.85 (s, 9H, 3×OCH$_3$), 4.36 (s, 2H, CH$_2$), 6.30 (s, 2H, Ph-H), 6.91 (d, 1H, J=7.2 Hz, Py-H), 7.09 (d, 1H, J=15.6 Hz, CH), 7.19 (d, 1H, J=8.0 Hz, Py-H), 7.48 (d, 1H, J=15.6 Hz, CH). HR-MS (ESI⁺) m/z 463.1974 [M+H]⁺, $C_{10}H_{12}N_2O_7S$ requires 462.1825.

A.30. (E)-6-((2,6-dimethoxystyrylsulfonyl)methyl-3-methoxypyridin-2-amine

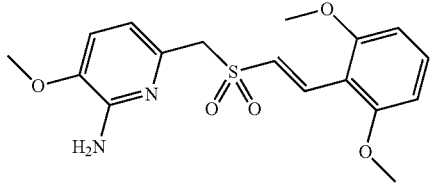 [SMILES: COc1ccc(CS(=O)(=O)/C=C/c2c(OC)cccc2OC)nc1N]

The titled compound was obtained by reduction of (E)-6-((2,6-dimethoxystyrylsulfonyl)methyl)-3-methoxy-2-nitropyridine according to the method described previously. yellow solid; ¹H NMR (Acetone-$D_6$) δ 3.75 (s, 2H, $CH_2$), 3.88 (s, 3H, $OCH_3$), 3.96 (s, 3H, $OCH_3$), 4.05 (s, 3H, $OCH_3$), 5.90 (d, 1H, J=10.0 Hz, CH), 5.99 (d, 1H, J=10.0 Hz, CH), 6.54 (d, 1H, J=8.4 Hz, Ph-H), 6.97 (d, 1H, J=8.0 Hz, Py-H), 7.11 (d, 1H, J=8.4 Hz, Ph-H), 7.31 (t, 1H, J=8.4 Hz, Ph-H), 7.46 (d, 1H, J=8.0 Hz, Py-H); HR-MS (ESI⁺) m/z 365.1147 [M+1]⁺, $C_{17}H_{18}N_2O_5S$ requires 364.1093.

A.31, (E)-6-((4-fluorostyrylsulfonyl)methyl)-3-methoxy-2-nitropyridine

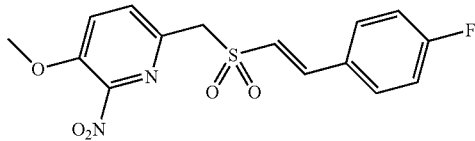 [SMILES: COc1ccc(CS(=O)(=O)/C=C/c2ccc(F)cc2)nc1[N+](=O)[O-]]

The title compound was obtained by reacting 2-((5-methoxy-6-nitropyridin-2-yl)methylsulfonyl)acetic acid (0.60 g, 2 mmol) and 4-fluorobenzaldehyde (0.31 g, 2.5 mmol) as pale purple solid (130 mg); ¹H-NMR (Acetone-$D_6$) δ 3.27-3.72 (m, 2H, $CH_2$), 4.08 (s, 3H, $OCH_3$), 4.68 (d, 1H, J=14.0 Hz, CH), 4.83 (d, 1H, J=14.0 Hz, CH), 7.12-7.17 (m, 2H, Ph-H), 7.53-7.56 (m, 2H, Ph-H), 7.91 (d, 1H, J=8.8 Hz, Py-H), 7.95 (d, 1H, J=8.8 Hz, Py-H); ¹³C-NMR (Acetone-$D_6$) δ 56.58, 59.97, 60.41, 68.23, 115.07, 124.48, 128.05, 131.38, 138.99, 139.00, 139.70, 147.50, 162.50; HR-MS (ESI⁺) m/z 353.0533 [M+1]⁺ $C_{18}H_{13}FN_2O_5S$ requires 352.0529

A.32. (E)-4-(2-((5-methoxy-6-nitropyridin-2-yl)methylsulfonyl)vinyl)benzonitrile

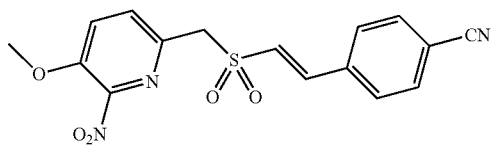 [SMILES: COc1ccc(CS(=O)(=O)/C=C/c2ccc(C#N)cc2)nc1[N+](=O)[O-]]

The title compound obtained by reaction between 2-((5-methoxy-6-nitropyridin-2-yl)methylsulfonyl)acetic acid (0.60 g, 2 mmol) and 4-formylbenzonitrile (0.33 g, 2.5 mmol) according to the method described previously. White crystalline solid (0.18 g, 25%); ¹H-NMR (Acetone-$D_6$) δ 3.34-3.77 (m, 2H, $CH_2$), 4.09 (s, 3H, $OCH_3$), 4.73 (d, 1H, J=13.6 Hz, CH), 4.83 (d, 1H, J=13.6 Hz, CH), 7.75 (d, 2H, J=8.4 Hz, Ph-H), 7.82 (d, 2H, J=8.4 Hz, Ph-H), 7.92 (d, 1H, J=8.8 Hz, Py-H), 8.01 (d, 1H, J=8.8 Hz, Py-H); ¹³C-NMR (Acetone-$D_6$) δ 56.59, 59.47, 60.53, 68.29, 111.50, 118.51, 118.52, 124.51, 127.04, 131.40, 132.31, 139.54, 146.89, 148.19; HR-MS (ESI⁺) m/z 360.0630 [M+1]⁺, $C_{16}H_{13}N_3O_5S$ requires 359.0576.

A.33, (E)-N-(3-methoxy-6-((2,4,6-trimethoxystyrylsulfonyl)methyl)pyridin-2-yl)methanesulfonamide

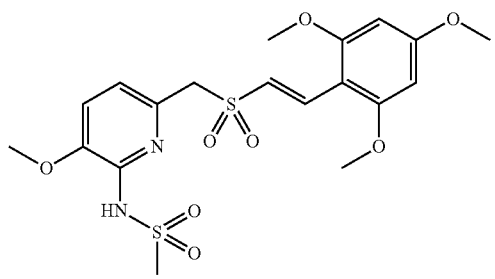

To a mixture of (E)-3-methoxy-6-((2,4,6-trimethoxystyrylsulfonyl)methyl)pyridin-2-amine (333 mg, 0.84 mmol) in dry pyridine (20 mL) cooling on an ice bath methanesulfonyl chloride (0.3 mL, 2 mmol) was added dropwise. The mixture was stirred at room temperature for 20 hours. After evaporated to dryness, the residue was purified by silica gel chromatography, eluting with PE/EtOAc (1:1 v/v) to afford 20 mg of the title compound as white powder. ¹H-NMR (DMSO-$d_6$): δ 3.26 (s, 3H, $OCH_3$), 3.82 (s, 3H, $CH_3$), 3.85 (s, 9H, 3×$OCH_3$), 4.45 (s, 2H, $CH_2$), 6.30 (s, 2H, Ph-H), 7.14 (d, 1H, J=15.6 Hz, CH), 7.15 (d, 1H, J=8.8 Hz, Py-H), 7.41 (d, 1H, J=8.4 Hz, Py-H), 7.56 (d, 1H, J=15.6 Hz, CH), 9.73 (s, 1H, NH).

B. Chemical Structure Determination

Figure 3:
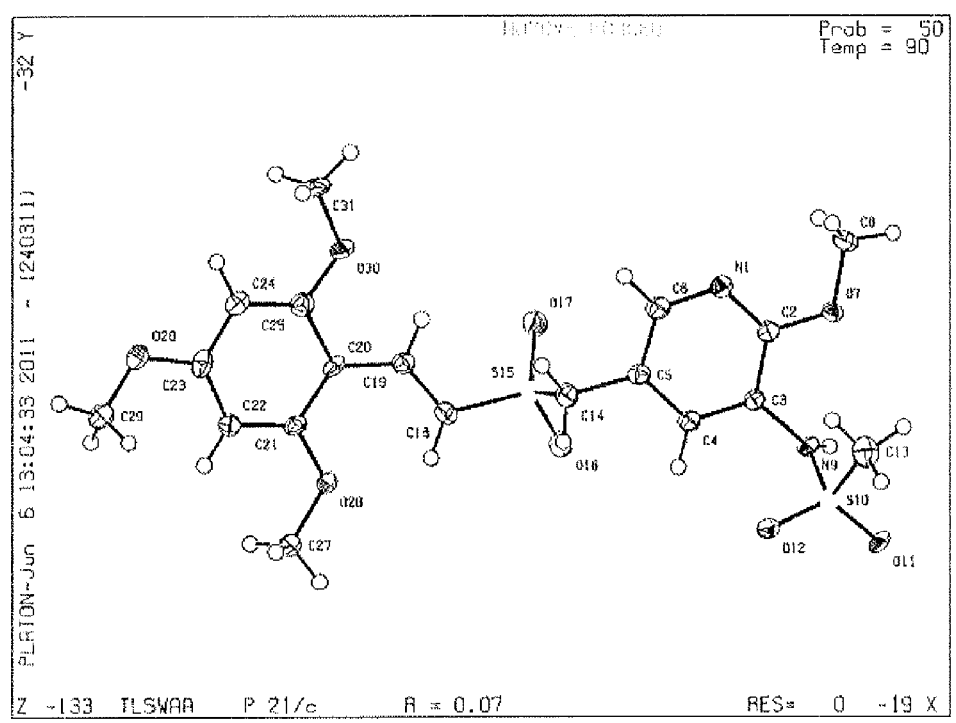
FIG. 3 is the crystal structure of (E)-N-(2-methoxy-5-((2,4,6-trimethoxystyrylsulfonyl)methyl)pyridin-3-yl)methanesulfonamide (compound A.12).

The crystal structure of (E)-N-(2-methoxy-5-((2,4,6-trimethoxystyrylsulfonyl)methyl)pyridin-3-yl)methanesulfonamide A.12 is shown in FIG. 3.

C. Biological Activity

C.1. MTT Proliferation Assay.

The compounds from the examples above were subjected to a standard cellular proliferation assay using the method described previously in S. Wang et al. J Med Chem. 2004, 47, 1662-1675. The data analysis used program Deltasoft 3™ and Microsoft Excel to determine $GI_{50}$ values (concentration of test compound which inhibits cell growth by 50%).

Results for the selected compounds A.10, A.12, A.13, A.17, and A.29 are shown in FIG. 4. These compounds acted to effectively inhibit cell growth.

C.2. Induction of Caspase3 Activity.

HCT-116 human colon cancer cells were treated with compound at the concentrations of $GI_{50}$ or $5×GI_{50}$ for a period of 48 hour. Activity of caspase3 was measured using Apo-ONE Homogeneous Caspase-3 kit (Promega G7790).

Figure 5:
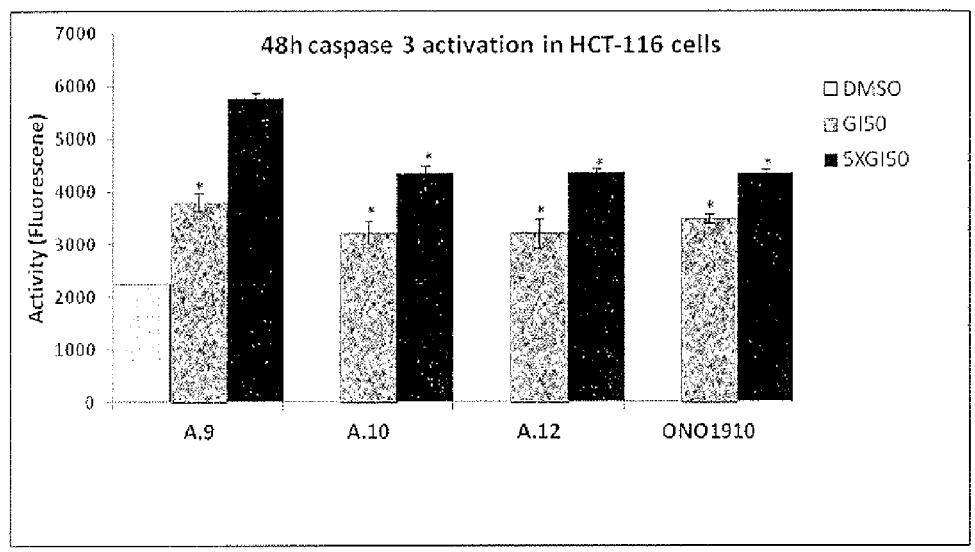
FIG. 5 illustrates the induction of caspase 3 activity. Vertical bars represent the mean±S.D. of three independent experiments. Values significantly (p<0.05) different from DMSO vehicle are marked with an asterisk (*).

The results for induction of caspase 3 activity are shown in FIG. 5. Vertical bars represent the mean±S.D. of three independent experiments. Values significantly (p<0.05) different from DMSO vehicle are marked with an asterisk (*).

As can be seen from this Figure, all compounds showed the ability to activate caspase3 activity at the $GI_{50}$ concentrations and in a dose-dependent manner. The efficacy of the compounds of the invention was comparable to the clinical compound ON01910.Na.

Therefore this indicates that the compounds of the invention can effectively induce apoptosis of cancer cells.

C.3. Cell-Cycle Effects.

HCT-116 human colon cancer cells were treated with DMSO and A.12 at $GI_{50}$ and $5 \times GI_5$ respectively for a period of 48 hrs. The cells were analysed for their DNA content by flow cytometry.

Figure 6:
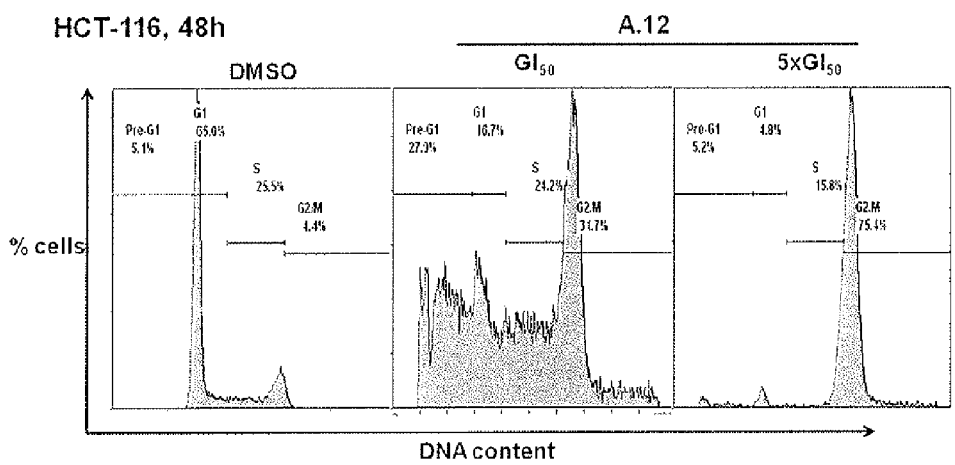
FIG. 6 illustrates the effect of the compound A.12 on the cell cycle.

The results for the cell cycle effect of A.12 are shown in FIG. 6. This shows that the cells treated with 0.62 μM A.12 resulted in a block of their cell cycle progression in G2/M phase and apoptosis indicated by increased sub-G1 cells. This further indicates the efficacy of the compounds of the invention.

D. Biopharmaceutical Profiling and PK Determination

Test compound partitioning between octanol and aqueous buffer was carried out using the shake-flask method. Compound $pK_a$ values were determined using a pH-metric titration method. Aqueous solubility was assessed by turbidimetric measurements. Apparent permeability coefficients were measured using a Caco-2 cell layer assay. In vitro phase-I liver metabolism was assessed by disappearance of parent compound (LC-MS quantitation) from a preparation of rat liver microsomes. Rat plasma protein binding was determined in an equilibrium dialysis assay as described in S. Wang, at al., J Med Chem, 2010, 53, 4367.

For PK measurements male adult CD1 mice weighing 25-30 g (Charles River) are split into weight matched groups of 3 per group. IV dosed mice were restrained in individual restraining tubes, the tail was warmed in warm water to vasodilate the tail vein, and the IV bolus was then administered via the tail vein. Orally dosed mice were held at the scruff of the neck and dosed via a metal gavage directly into the stomach. Immediately after dosing mice are returned to their cage, plastic box cage with sawdust bedding, and food and water available. Blood samples were collected from the mouse under anaesthesia by cardiac puncture using a 1 mL syringe and 25 gauge needle at time zero and at intervals up to 8 h. Harvested blood was centrifuged at 7000×G for 2 minutes, and the plasma aspirated and frozen at 20° C. until analysis. Quantitative compound level analysis was carried out using LC-MS/MS methods. Pharmacokinetic data derived using PK Solutions 2.0, non-compartmental analysis. Oral bioavailability (% F) was calculated by taking the ratio of dose-normalised AUC values from oral versus parenteral dosing.

FIG. 7 shows the results for the mice pharmacokinetics, with a comparison of intravenous (IV) and orally (PO) administered compound A.12 and ON01910.Na.

As shown in FIG. 7, compound A.12 has significantly improved pharmacokinetic properties compared with clinical compound ON01910.Na, and demonstrated excellent oral bioavailability (F=56% at 10 mg/kg).

It can therefore be seen that the compounds of the invention are effective at inhibiting growth of cancer cells and inducing apoptosis of cancer cells and can act as cell-cycle inhibitors. Surprisingly, the compounds of the invention may be of comparable or greater effectiveness than the clinical compound ON01910.Na, whilst exhibiting improved oral bioavailability as compared to that compound. In particular, the compounds appear to show excellent oral bioavailability, indicating that they could be used as orally administered medicaments for therapy.

Therefore a key benefit of the invention is the provision of compounds that can be used as anti-tumor agents or as agents against other proliferative disorders, in a similar manner to the known clinical compound ON01910.Na, but which have properties that make them suitable for oral administration. It would not have been predicted that the compounds of the invention would have both excellent effects in terms of inhibiting growth of cancer cells, inducing apoptosis of cancer cells and inhibiting cell-cycles whilst also having excellent oral bioavailability.

The invention claimed is:
1. A compound of formula I:

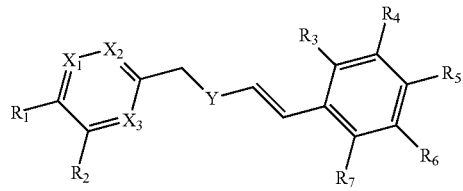

or a pharmaceutically acceptable salt or solvate or physiologically hydrolysable, solubilising or immobilisable derivative thereof;
wherein:
any one of $X_1$, $X_2$ and $X_3$ is a N atom and the remaining two of $X_1$, $X_2$ and $X_3$ are independently $CR^{13}$;
Y is selected from $SO_2$ and SO;
$R^1$, $R^2$, $R^3$, and $R^7$ and the one or two $R^{13}$ groups are each independently selected from $R^{10}$,
$R^{10}$ is selected from $R^8$, alkyl, aryl, heteroaryl and combinations of two or more thereof and combinations with one or more $R^9$, or $R^{10}$ is one or more moieties $R^{11}$ linking one or more alkyl, alkoxy, aryl, heteroaryl or $R^8$ or $R^9$ groups or combinations thereof, directly or via a moiety selected from alkylene, arylene, heteroarylene or combinations thereof, wherein alkyl, aryl, heteroaryl groups or moieties thereof may be substituted with one or more groups $R^{12}$, or $R^{10}$ is selected from a group $R^{12}$;
$R^{11}$ is selected from O—, N—, NH—, N═C, CO—, COO—, CON—, CONH—, $SO_2$—, $SO_2N$—, $SO_2NH$—;
$R^{12}$ is selected from halogeno, $NH_2$, $NO_2$, CN, OH, COOH, $CONH_2$, C(═NH)$NH_2$, $SO_3H$, $SO_2NH_2$, $SO_2CH_3$, $OCH_3$, $OCH_2CH_3$, $CF_3$;
$R^8$ and $R^9$ are selected from one or more solubilising moieties independently chosen from i) ionisable organic acids, ii) ionisable organic bases, iii) chemical functions or moieties providing covalent or non-covalent attachment or binding to a solid phase or an immobile receptor and combinations thereof;
$R^4$, $R^5$ and $R^6$ are each independently selected from H and $R^{10}$, or two of $R^4$ to $R^6$ are linked to form a cyclic ether or amine containing one or more additional oxygen or nitrogen atoms, and
wherein at least one of $R^3$, $R^5$ or $R^7$ is $R^{10}$.
2. A method for treating cancer or a proliferative disorder mediated by one or more enzymes selected from AKT, Aurora kinase, BCR-ABL, CDK, FLT, GSK3, IKK, JAK, MAPK, PDGF, PI3K, PKA, PKB, PKC, PLK, Src and VEGF family enzymes, in a human or animal subject, the method comprising administering to a human or animal in need thereof a therapeutically effective amount of the compound of formula I or a pharmaceutically acceptable salt, solvate, or physiologically hydrolysable, solubilising or immobilising derivative thereof, as defined in claim 1.

3. A pharmaceutical composition comprising the compound of formula I or a pharmaceutically acceptable salt or solvate, or physiologically hydrolysable, solubilising or immobilising derivative thereof, as defined in claim 1, in association with one or more diluents, carriers or excipients.

4. The compound of formula I or a pharmaceutically acceptable salt, solvate or physiologically hydrolysable, solubilising or immobilising derivative thereof, of claim 1, wherein $X_1$ is N and $X_2$ and $X_3$ are $CR^{13}$, or $X_2$ is N and $X_1$ and $X_3$ are $CR^{13}$, or $X_3$ is N and $X_1$ and $X_2$ are $CR^{13}$, such that the heteroaryl ring is an optionally substituted-pyridine.

5. The compound of formula I or a pharmaceutically acceptable salt, solvate or physiologically hydrolysable, solubilising or immobilising derivative thereof, of claim 4 wherein $X_2$ is CH, one of $X_1$ and $X_3$ is a N atom and the remaining one of $X_1$ and $X_3$ is $CR^{13}$.

6. The compound of formula I or a pharmaceutically acceptable salt, solvate or physiologically hydrolysable, solubilising or immobilising derivative thereof, of claim 1, wherein $R^{10}$ is selected from $R^8$, alkyl, alkyl-$R^8$, alkyl-cycloalkyl which may be part unsaturated, cycloheteroalkyl, alkyl-cycloheteroalkyl, aryl, aryl-$R^8$, aralkyl, aralkyl-$R^8$, heteroaryl, alkyl-heteroaryl, halogeno, $NO_2$, CN, OH, O-alkyl, O-cycloalkyl which may be part unsaturated, O-aryl, O-heteroaryl, O—$R^8$, S-alkyl, $NH_2$, NH-alkyl, part unsaturated NH-cycloalkyl, NH-cycloheteroalkyl, NH-aryl, NH-heteroaryl, N-(alkyl)$_2$, N-(aryl)$_2$, N-(alkyl)(cycloalkyl), N-(alkyl)(cycloheteroalkyl), N-(alkyl)(aryl), N-(alkyl)(heteroaryl), NH—$R^8$, N—($R^8$)($R^9$), N-(alkyl)($R^8$), N-(aryl)($R^8$), NCHalkyl, NC(alkyl)$_2$, NC(alkyl)($R^8$), NC($R^8$)($R^9$), COOH, COO—$R^8$, COO-alkyl, $CONH_2$, CONH-alkyl, CONH-aryl, CONH-heteroaryl, CON-(alkyl)($R^8$), CON(aryl)($R^8$), CON(heteroaryl)($R^8$), CONH—$R^8$, CON—($R^8$)($R^9$), NHC(=O)-alkyl, NHC(=O)-aryl, NHC(=O)-heteroaryl, NHC(=O)—$R^8$, $SO_3H$, $SO_2$-alkyl, $SO_2$-alkyl-$R^8$, $SO_2$-aryl, $SO_2$-aryl-$R^8$, $SO_2$-heteroaryl, $SO_2$-heteroaryl-$R^8$, $SO_2NH_2$, $SO_2NH$—$R^8$, $SO_2N$—($R^8$)($R^9$), $NHSO_2R^8$, $CF_3$, CO—$R^8$, CO-alkyl, CO-alkyl-$R^8$, CO-cycloheteroalkyl, CO-aryl, CO-aryl-$R^8$, CO-heteroaryl, CO-heteroarylalkyl or CO-heteroaryl$R^8$, wherein alkyl, aryl, aralkyl, heteroaryl groups may be further substituted with one or more groups selected from halogeno, $NO_2$, CN, OH, O-methyl, $NH_2$, COOH, $CONH_2$ and $CF_3$.

7. The compound of formula I or a pharmaceutically acceptable salt, solvate or physiologically hydrolysable, solubilising or immobilising derivative thereof, of claim 1, wherein $R^1$, $R^2$ and $R^{13}$ are independently selected from: H, CN, $CF_3$, halogeno, OH, O-alkyl, O-cycloalkyl which may be part unsaturated, O-heteroaryl, S-alkyl, $C_{1-6}$ alkyl, alkyl-cycloalkyl which may be part unsaturated, aryl, cycloheteroalkyl, alkylcycloheteroalkyl such as $CH_2$-cycloheteroalkyl, heteroaryl, alkyl-heteroaryl such as $CH_2$-heteroaryl, $NO_2$, $NH_2$, NH-alkyl, N(alkyl)$_2$, N-(alkyl)($R^8$), part unsaturated NH-cycloalkyl, NH-cycloheteroalkyl, NH-heteroaryl, —NHC(=O)alkyl, NHalkylCOOH, $NHSO_2$alkyl, $NHSO_2R^8$, NCHalkyl, NC(alkyl)$_2$, NC(alkyl)($R^8$), NC($R^8$)($R^9$), $CONH_2$, CONH-(alkyl), CONH-(heteroaryl), CON-(alkyl)($R^8$), $R^8$, $CO_2$alkyl, CO-alkyl, CO-cycloheteroalkyl, CO-heteroaryl, CONH-heteroaryl; wherein alkyl, cycloheteroalkyl, aryl, aralkyl, heteroaryl groups may be further substituted with one or more groups selected from halogeno, $NO_2$, CN OH, O-methyl, $NH_2$, COOH, $CONH_2$ and $CF_3$.

8. The compound of formula I or a pharmaceutically acceptable salt, solvate or physiologically hydrolysable, solubilising or immobilising derivative thereof, of claim 1, wherein $R^1$ is selected from $CH_3$, $OCH_3$, $OCH_2CH_3$, O-propyl, O-butyl, halogeno, $NH_2$, NH-alkyl, N(alkyl)$_2$, $CO_2$alkyl, CO-alkyl, $CONH_2$, CONH-alkyl and heteroaryl.

9. The compound of formula I or a pharmaceutically acceptable salt, solvate or physiologically hydrolysable, solubilising or immobilising derivative thereof, of claim 1, wherein $R^2$ is selected from $CH_3$, $OCH_3$, $OCH_2CH_3$, $OCH_2CH_2Oalkyl$, $OCH_2CH_3N(alkyl)_2$, OH, halogeno, $NO_2$, $NH_2$, NH-alkyl, NHC(=O)alkyl, NHalkylCOOH, NHalkylC(=O)$NH_2$, NHalkylC(=O)alkyl, NHalkyl, N(alkyl)$_2$, cycloheteroalkyl, part unsaturated NH-cycloalkyl, NH-heteroaryl, $NHSO_2$alkyl, $NHSO_2$haloalkyl, NH-cycloheteroalkyl, and NH-cycloheteroalkyl substituted with $SO_2$ alkyl or heteroalkyl.

10. The compound of formula I or a pharmaceutically acceptable salt, solvate or physiologically hydrolysable, solubilising or immobilising derivative thereof, of claim 9, wherein $R^2$ is selected from $NO_2$, $NH_2$, NHMe, NHC(=O)Me, NHEt, $NMe_2$, $NEt_2$, NMeC(=O)Me, NEtC(=O)Me, $NEtCO_2Me$, $NHCH_2C$(=O)Et, $NHCH_2CO_2Et$, $NHCH_2C$(=O)Me, N—$NHCH_2CO_2H$, $NHCH_2C$(=O)$NH_2$, $NHSO_2Me$, $NHSO_2CF_3$, $NHCH_2CH_2NEt_2$,

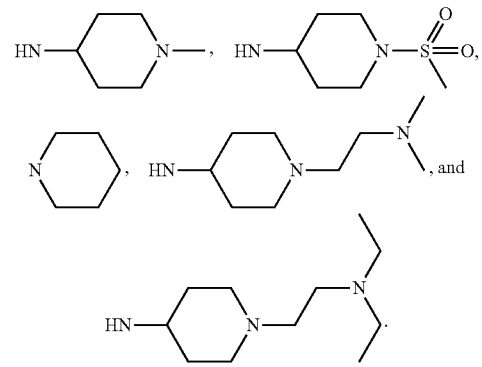

11. The compound of formula I or a pharmaceutically acceptable salt, solvate or physiologically hydrolysable, solubilising or immobilising derivative thereof, of claim 1, wherein $R^{13}$ is selected from H and $C_{1-3}$ alkyl.

12. The compound of formula I or a pharmaceutically acceptable salt, solvate or physiologically hydrolysable, solubilising or immobilising derivative thereof, of claim 1, wherein each $R^3$ or $R^7$ is independently selected from H, $C_{1-4}$ alkyl, CN, $CF_3$, halogeno, $NO_2$, O-methyl, O-ethyl, O-propyl, O-butyl, S-alkyl, $NH_2$, NH-alkyl, N(alkyl)$_2$, $CO_2$alkyl, CO-alkyl, $CONH_2$, CONH-alkyl and heteroaryl.

13. The compound of formula I or a pharmaceutically acceptable salt, solvate or physiologically hydrolysable, solubilising or immobilising derivative thereof, of claim 1, wherein $R^4$, $R^5$ and $R^6$ are independently selected from H, halogeno, $NO_2$, CN, OH, $NH_2$, O-alkyl, O-cycloalkyl which may be part unsaturated, O-aryl, O-heteroaryl, S-alkyl, N-linked N-(alkyl)(cycloheteroalkyl), $SO_2$-cycloheteroalkyl and CO-cycloheteroalkyl.

14. The compound of formula I or a pharmaceutically acceptable salt, solvate or physiologically hydrolysable, solubilising or immobilising derivative thereof, of claim 13, wherein $R^4$ and $R^6$ are both H.

15. The compound of formula I or a pharmaceutically acceptable salt, solvate or physiologically hydrolysable, solubilising or immobilising derivative thereof, of claim 1, wherein two or more of $R^3$ to $R^7$ are independently selected from $OC_{1-6}$ alkyl.

16. The compound of formula I or a pharmaceutically acceptable salt, solvate or physiologically hydrolysable, solubilising or immobilising derivative thereof, of claim 15 wherein $R^3$, $R^5$ and $R^7$ are independently selected from $OC_{1-6}$ alkyl, such as O-methyl, O-ethyl, O-propyl and O-butyl.

17. The compound of formula I of claim 1, wherein the compound is provided in the form of a pharmaceutically acceptable salt or solvate or physiologically hydrolysable, solubilising or immobilisable derivative.

18. The compound of formula I or a pharmaceutically acceptable salt, solvate or physiologically hydrolysable, solubilising or immobilising derivative thereof, of claim 17, wherein the compound is provided in the form of a pharmaceutically acceptable salt or ester.

19. The compound of formula I or a pharmaceutically acceptable salt, solvate or physiologically hydrolysable, solubilising or immobilising derivative thereof, of claim 1, wherein the compound is provided in a form suitable for oral administration, or is administered orally to the human or animal in need.

20. The compound of formula I or a pharmaceutically acceptable salt, solvate or physiologically hydrolysable, solubilising or immobilising derivative thereof, of claim 1, wherein the compound is used to treat leukaemia or cancer.

21. The compound of formula I or a pharmaceutically acceptable salt, solvate or physiologically hydrolysable, solubilising or immobilising derivative thereof, of claim 1, wherein the compound is used to treat a disorder selected from the group consisting of chronic lymphocytic leukaemia, lymphoma, leukaemia, breast cancer, lung cancer, prostate cancer, colon cancer, melanoma, pancreatic cancer, ovarian cancer, squamous carcinoma, carcinoma of head and neck, endometrial cancer, and aesophageal carcinoma.

\* \* \* \* \*